(12) United States Patent
Hartley et al.

(10) Patent No.: US 12,171,601 B2
(45) Date of Patent: *Dec. 24, 2024

(54) MEDICAL IMAGING SYSTEMS AND ASSOCIATED DEVICES AND METHODS

(71) Applicant: Pulmera, Inc., Redwood City, CA (US)

(72) Inventors: Bryan I. Hartley, Nashville, TN (US); Rene Vargas-Voracek, Sunnyvale, CA (US); Ke Li, Middleton, WI (US)

(73) Assignee: Pulmera, Inc., Redwood City, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 18/424,006

(22) Filed: Jan. 26, 2024

(65) Prior Publication Data

US 2024/0206835 A1 Jun. 27, 2024

Related U.S. Application Data

(63) Continuation of application No. 18/459,869, filed on Sep. 1, 2023, now Pat. No. 11,918,395, which is a
(Continued)

(51) Int. Cl.
*A61B 6/00* (2024.01)
*A61B 6/46* (2024.01)
(Continued)

(52) U.S. Cl.
CPC .......... *A61B 6/4441* (2013.01); *A61B 6/4405* (2013.01); *A61B 6/466* (2013.01); *A61B 6/584* (2013.01); *G06T 11/005* (2013.01)

(58) Field of Classification Search
CPC .. A61B 1/00; A61B 5/706; A61B 6/44; A61B 6/4411; A61B 6/4476; A61B 6/46;
(Continued)

(56) References Cited

U.S. PATENT DOCUMENTS

| 3,803,417 A | 4/1974 | Kok |
| 4,358,856 A | 11/1982 | Stivender et al. |

(Continued)

FOREIGN PATENT DOCUMENTS

| WO | 2021059165 A1 | 4/2021 |
| WO | 2022217291 A1 | 10/2022 |
| WO | 2023004303 A1 | 1/2023 |

OTHER PUBLICATIONS

Abella, Monica, Enabling tomography with low-cost C-arm systems, PLoS ONE, 13(9) 2018, 18 pages.
(Continued)

*Primary Examiner* — Don K Wong
(74) *Attorney, Agent, or Firm* — FORTEM IP LLP

(57) ABSTRACT

Systems, methods, and devices for medical imaging are disclosed herein. In some embodiments, a method for imaging an anatomic region includes receiving, from a detector carried by an imaging arm of an x-ray imaging apparatus, a plurality of images of the anatomic region. The images can be obtained during manual rotation of the imaging arm. The imaging arm can be stabilized by a shim structure during the manual rotation. The method can also include receiving, from at least one sensor coupled to the imaging arm, pose data of the imaging arm during the manual rotation. The method can further include generating, based on the images and the pose data, a 3D representation of the anatomic region.

20 Claims, 42 Drawing Sheets

Related U.S. Application Data continuation of application No. 18/175,275, filed on Feb. 27, 2023, now Pat. No. 11,786,198, which is a continuation of application No. 17/819,811, filed on Aug. 15, 2022, now Pat. No. 11,617,552, which is a continuation of application No. 17/658,642, filed on Apr. 8, 2022, now Pat. No. 11,457,883.

(60) Provisional application No. 63/260,241, filed on Aug. 13, 2021, provisional application No. 63/203,270, filed on Jul. 15, 2021, provisional application No. 63/172,886, filed on Apr. 9, 2021.

(51) Int. Cl.
*A61B 6/58* (2024.01)
*G06T 11/00* (2006.01)

(58) Field of Classification Search
CPC ......... A61B 6/461; A61B 6/467; A61B 6/547; A61B 6/545; A61B 6/466; A61B 6/463; A61B 6/488; G06T 3/00; G06T 3/0068; G06T 3/40; G06T 11/00; G06T 11/005; G06T 11/006; G06T 11/40; G06T 5/10; G06T 17/05; G06T 17/10
See application file for complete search history.

(56) References Cited

U.S. PATENT DOCUMENTS

| | | | |
|---|---|---|---|
| RE34,943 E | 5/1995 | Van et al. | |
| 6,659,642 B2 | 12/2003 | Hanover | |
| 6,666,579 B2 | 12/2003 | Jensen | |
| 6,814,489 B2 | 11/2004 | Jensen et al. | |
| 7,048,440 B2 | 5/2006 | Graumann et al. | |
| 7,160,027 B2 | 1/2007 | Bauer et al. | |
| 7,170,972 B2 | 1/2007 | Altman | |
| 7,278,785 B2 | 10/2007 | Fadler et al. | |
| 7,331,711 B2 | 2/2008 | Sandkamp et al. | |
| 7,837,385 B2 | 11/2010 | Klingenbeck-Regn | |
| 8,315,355 B2 | 11/2012 | Mohamed | |
| 8,636,410 B2 | 1/2014 | Yao et al. | |
| 8,961,010 B2 | 2/2015 | Meyer et al. | |
| 9,044,190 B2 | 6/2015 | Rubner et al. | |
| 9,144,145 B2 | 9/2015 | Fürst et al. | |
| 9,427,204 B2 | 8/2016 | Graumann | |
| 9,492,131 B2 | 11/2016 | Meek et al. | |
| 9,693,437 B2 | 6/2017 | Simmons et al. | |
| 10,076,295 B2 | 9/2018 | Gemmel et al. | |
| 10,092,265 B2 | 10/2018 | Lavallee et al. | |
| 11,006,913 B2 | 5/2021 | Shirota et al. | |
| 11,295,864 B2 | 4/2022 | Benishti et al. | |
| 11,457,883 B1 | 10/2022 | Hartley et al. | |
| 11,617,552 B2 | 4/2023 | Hartley et al. | |
| 11,786,198 B2 * | 10/2023 | Hartley | A61B 6/4441 |
| | | | 378/197 |
| 11,918,395 B2 * | 3/2024 | Hartley | A61B 6/032 |
| 2010/0331857 A1 | 12/2010 | Doyle et al. | |
| 2013/0195338 A1 | 8/2013 | Xu et al. | |
| 2017/0049411 A1 | 2/2017 | Papaioannou | |
| 2017/0296841 A1 | 10/2017 | Pekar et al. | |
| 2019/0000564 A1 | 1/2019 | Navab et al. | |
| 2019/0038365 A1 | 2/2019 | Soper et al. | |
| 2019/0107596 A1 | 4/2019 | Holdsworth et al. | |
| 2019/0170596 A1 | 6/2019 | Motieian Najar et al. | |
| 2019/0355278 A1 | 11/2019 | Sainsbury et al. | |
| 2020/0046436 A1 | 2/2020 | Tzeisler et al. | |
| 2020/0121267 A1 | 4/2020 | Deutschmann | |
| 2020/0268460 A1 | 8/2020 | Tse et al. | |
| 2020/0268473 A1 | 8/2020 | Gregerson et al. | |
| 2021/0093268 A1 | 4/2021 | Eguchi | |
| 2022/0323029 A1 | 10/2022 | Hartley et al. | |
| 2022/0386974 A1 | 12/2022 | Hartley et al. | |
| 2023/0200763 A1 | 6/2023 | Hartley et al. | |
| 2023/0404501 A1 | 12/2023 | Hartley et al. | |
| 2024/0148445 A1 | 5/2024 | Hartley et al. | |

OTHER PUBLICATIONS

Fahrig, R. et al., Three-dimensional computed tomographic reconstruction using a C-arm mounted XRII: Correction of image intensifier distortion, Med. Phys., 24 (7), Jul. 1997, 1097-1106.

International Search Report and Written Opinion dated Jun. 27, 2022; International Application No. PCT/US2022/071649; 19 pages.

International Search Report and Written Opinion mailed Nov. 16, 2022, International Application No. PCT/US2022/073876, 17 pages.

Lemammer, Imane et al., Online mobile C-arm calibration using inertial sensors: a preliminary study in order to achieve CBCT, International Journal of Computer Assisted Radiology and Surgery, 2020, 15: 213-224.

Paraíso Labora, Martin et al., Calibration of a C-arm X-ray system for its use in tomography, Universidad Carlos III de Madrid, 2013, 94 pages.

Rottman, Caleb et al., Mobile C-arm 3D Reconstruction in the Presence of Uncertain Geometry, Lecture Notes in Computer Science, Oct. 2015, 8 pages.

Sethi, Sonali et al., Real-time Visualization of Fluoro-Invisible Pulmonary Nodules and Their Relative Position to the Biopsy Tool Tip During Bronchoscopy Can Potentially Increase Diagnostic Yield Using C-Arm Based Tomography, bodyvisionmedical.com/clinical, 2019, 3 pages.

Illumisite Platform Technology Brochure, Medtronic, Inc., www.medtronic.com, 2019, 8 pages.

Pritchett, Michael A. et al., Electromagnetic Navigation Bronchoscopy With Tomosynthesis-based Visualization and Positional Correction, Journal of Bronchology & Interventional Pulmonology, vol. 28, No. 1, Jan. 2021, 11 pages.

Pritchett, Michael A., et al., Virtual or reality: divergence between preprocedural computed tomography scans and lung anatomy during guided bronchoscopy, Journal of Thoracic Disease, 2020, 12(4): 1595-1611.

* cited by examiner

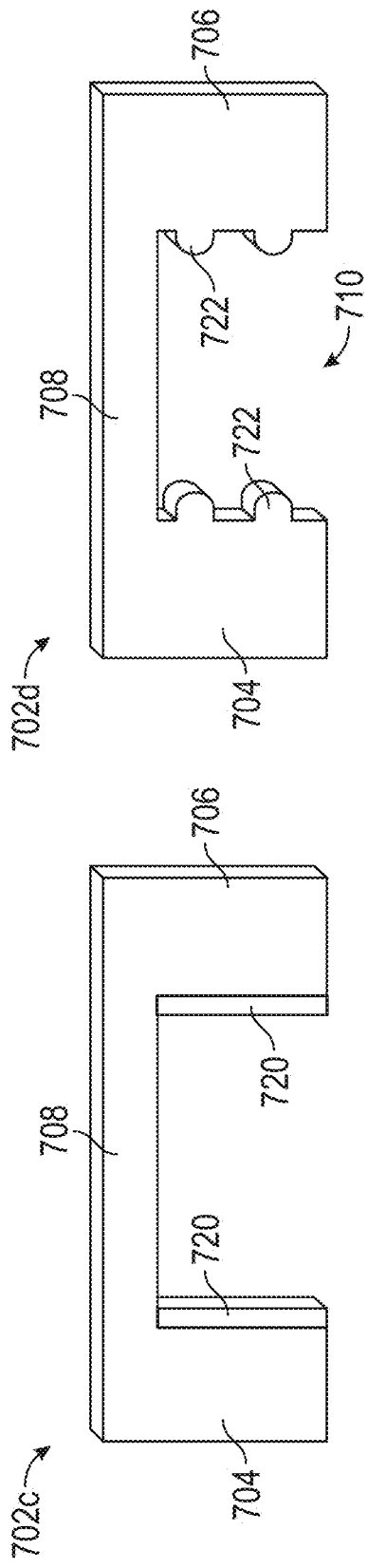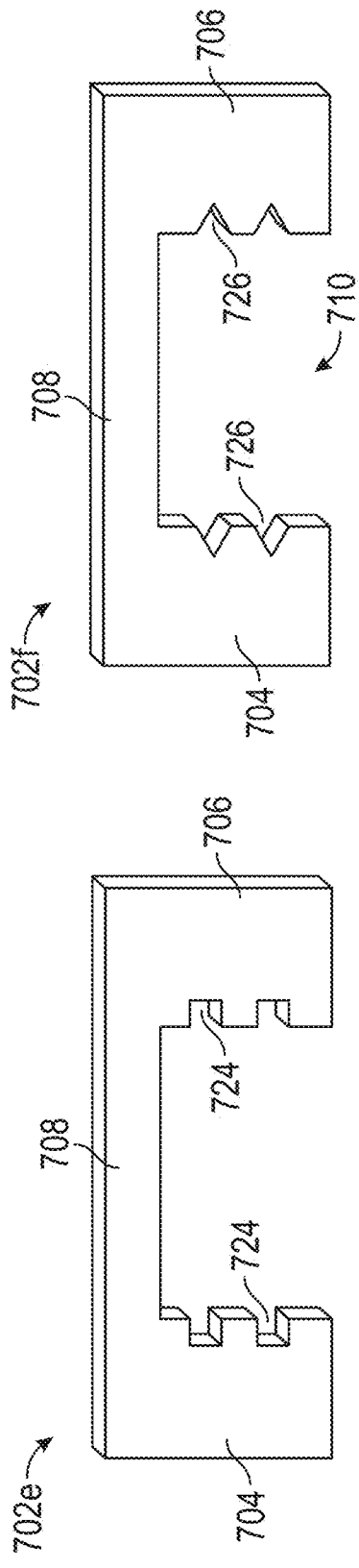
FIG. 7E
FIG. 7F
FIG. 7G
FIG. 7H

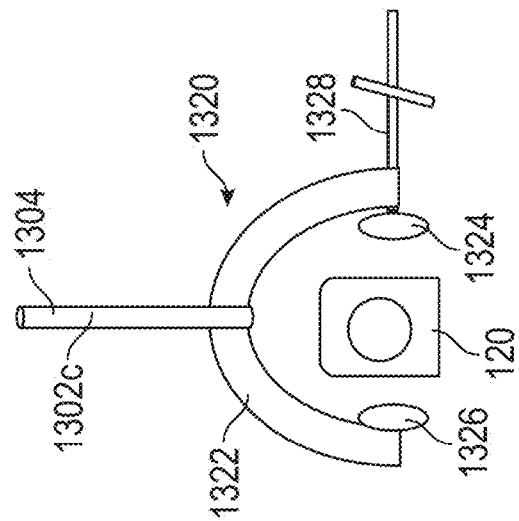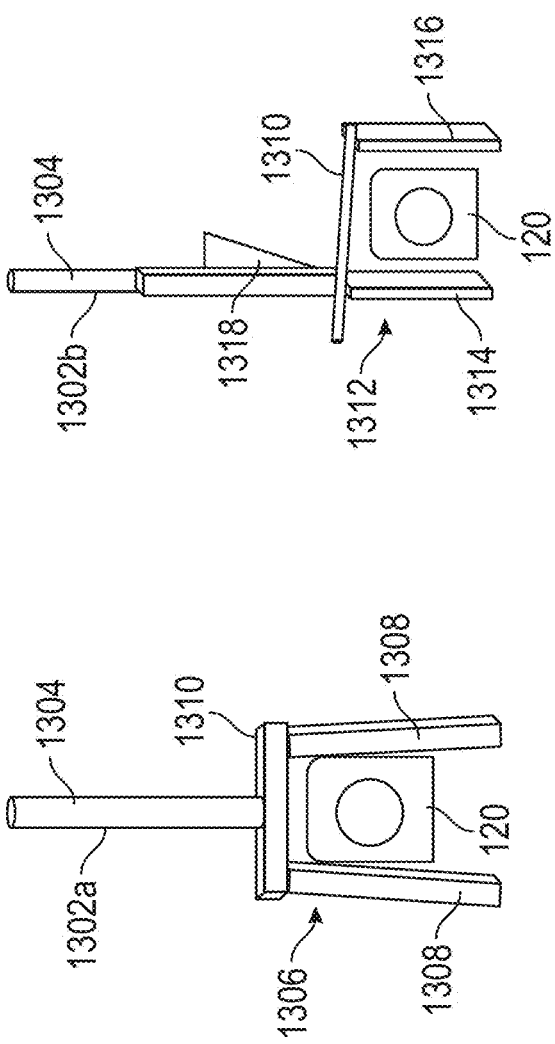
FIG. 13B
FIG. 13C
FIG. 13D

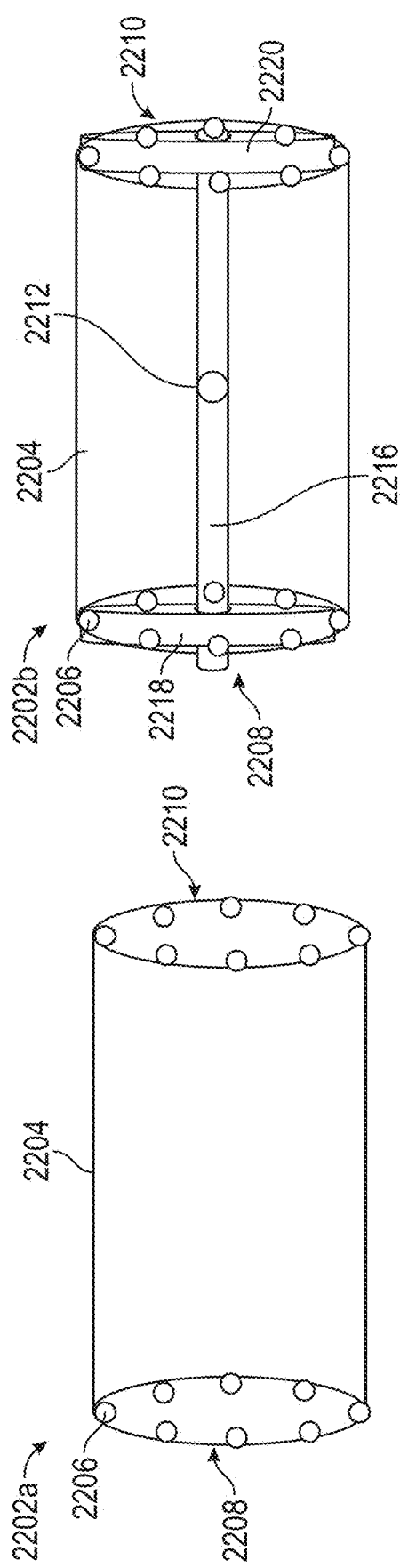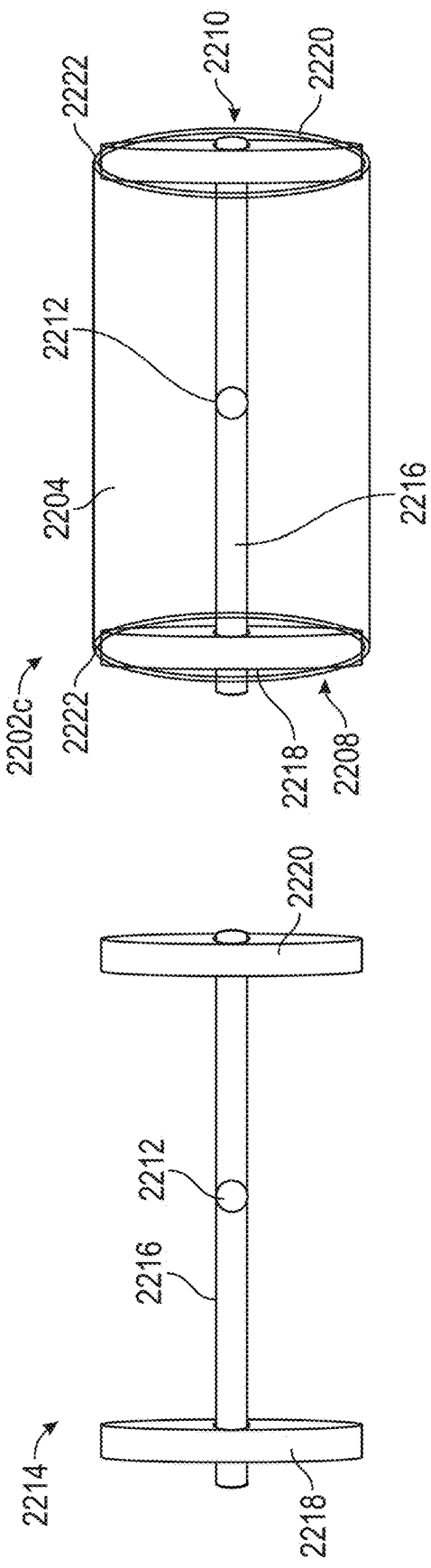
FIG. 22A  FIG. 22B  FIG. 22C  FIG. 22D

2500'

2502' Position a calibration phantom near the imaging apparatus

2504' Obtain first images of the phantom

2506' Obtain first pose data based on the first images

2508' Remove the phantom and position a fiducial marker board near the patient

2510' Obtain second images of the fiducial marker board and the patient

2512' Obtain second pose data based on the second images

2514' Generate a 3D reconstruction based on the first and second pose data

FIG. 25B

MEDICAL IMAGING SYSTEMS AND ASSOCIATED DEVICES AND METHODS

CROSS-REFERENCE TO RELATED APPLICATIONS

The present application is a continuation of U.S. patent application Ser. No. 18/459,869, filed Sep. 1, 2023, now U.S. Pat. No. 11,918,395, issued Mar. 5, 2024, which is a continuation of U.S. patent application Ser. No. 18/175,275, filed Feb. 27, 2023, now U.S. Pat. No. 11,786,198, issued Oct. 17, 2023, which is a continuation of U.S. patent application Ser. No. 17/819,811, filed Aug. 15, 2022, now U.S. Pat. No. 11,617,552, issued Apr. 4, 2023, which is a continuation of U.S. patent application Ser. No. 17/658,642, filed Apr. 8, 2022, now U.S. Pat. No. 11,457,883, issued Oct. 4, 2022, which claims the benefit of priority to U.S. Provisional Application No. 63/172,886, filed Apr. 9, 2021; U.S. Provisional Application No. 63/203,270, filed Jul. 15, 2021; and U.S. Provisional Application No. 63/260,241, filed Aug. 13, 2021; each of which is incorporated by reference herein in its entirety.

TECHNICAL FIELD

The present technology relates generally to medical imaging, and in particular, to systems for generating a three-dimensional (3D) representation of a patient's anatomy and associated methods and devices.

BACKGROUND 3D anatomic models, such as computed tomography (CT) volumetric reconstructions, are frequently used in image-guided medical procedures to allow the physician to visualize the patient anatomy in three dimensions and accurately position surgical tools at the appropriate locations. However, 3D models generated from preprocedural image data may not accurately reflect the actual anatomy at the time of the procedure. Moreover, if the model is not correctly registered to the anatomy, it may be difficult or impossible for the physician to navigate the tool to the right location, thus compromising the accuracy and efficacy of the procedure.

Cone-beam computed tomography (CBCT) has been used to generate high resolution, 3D volumetric reconstructions of a patient's anatomy for image guidance during a medical procedure. However, many physicians do not have ready access to conventional CBCT imaging systems because these systems are extremely expensive and often reserved for use by specialty departments. While tomosynthesis (also known as limited-angle tomography) has also been used for intraprocedural imaging, this technique is unable to produce 3D reconstructions with sufficiently high resolution for many procedures. Accordingly, improved medical imaging systems and methods are needed.

BRIEF DESCRIPTION OF THE DRAWINGS

Many aspects of the present disclosure can be better understood with reference to the following drawings. The components in the drawings are not necessarily to scale. Instead, emphasis is placed on clearly illustrating the principles of the present disclosure.

FIG. 7E illustrates a shim structure including a set of ridges configured in accordance with embodiments of the present technology.

FIG. 7F illustrates a shim structure including a plurality of protrusions configured in accordance with embodiments of the present technology.

FIG. 7G illustrates a shim structure including a plurality of square or rectangular notches configured in accordance with embodiments of the present technology.

FIG. 7H illustrates a shim structure including a plurality of triangular notches configured in accordance with embodiments of the present technology.

FIGS. 13A and 13B illustrate a lever structure configured in accordance with embodiments of the present technology.

FIG. 13C illustrates an adjustable lever structure configured in accordance with embodiments of the present technology.

FIG. 13D illustrates another adjustable lever structure configured in accordance with embodiments of the present technology.

FIG. 22A illustrates a fiducial marker phantom for geometric calibration in accordance with embodiments of the present technology.

FIG. 22B illustrates another fiducial marker phantom configured in accordance with embodiments of the present technology.

FIG. 22C illustrates an assembly that can form part of the fiducial marker phantom of FIG. 22B, in accordance with embodiments of the present technology.

FIG. 22D illustrates another fiducial marker phantom configured in accordance with embodiments of the present technology.

FIG. 25B is a flow diagram illustrating a method for operating an imaging apparatus, in accordance with embodiments of the present technology.

DETAILED DESCRIPTION

Figure 1A:
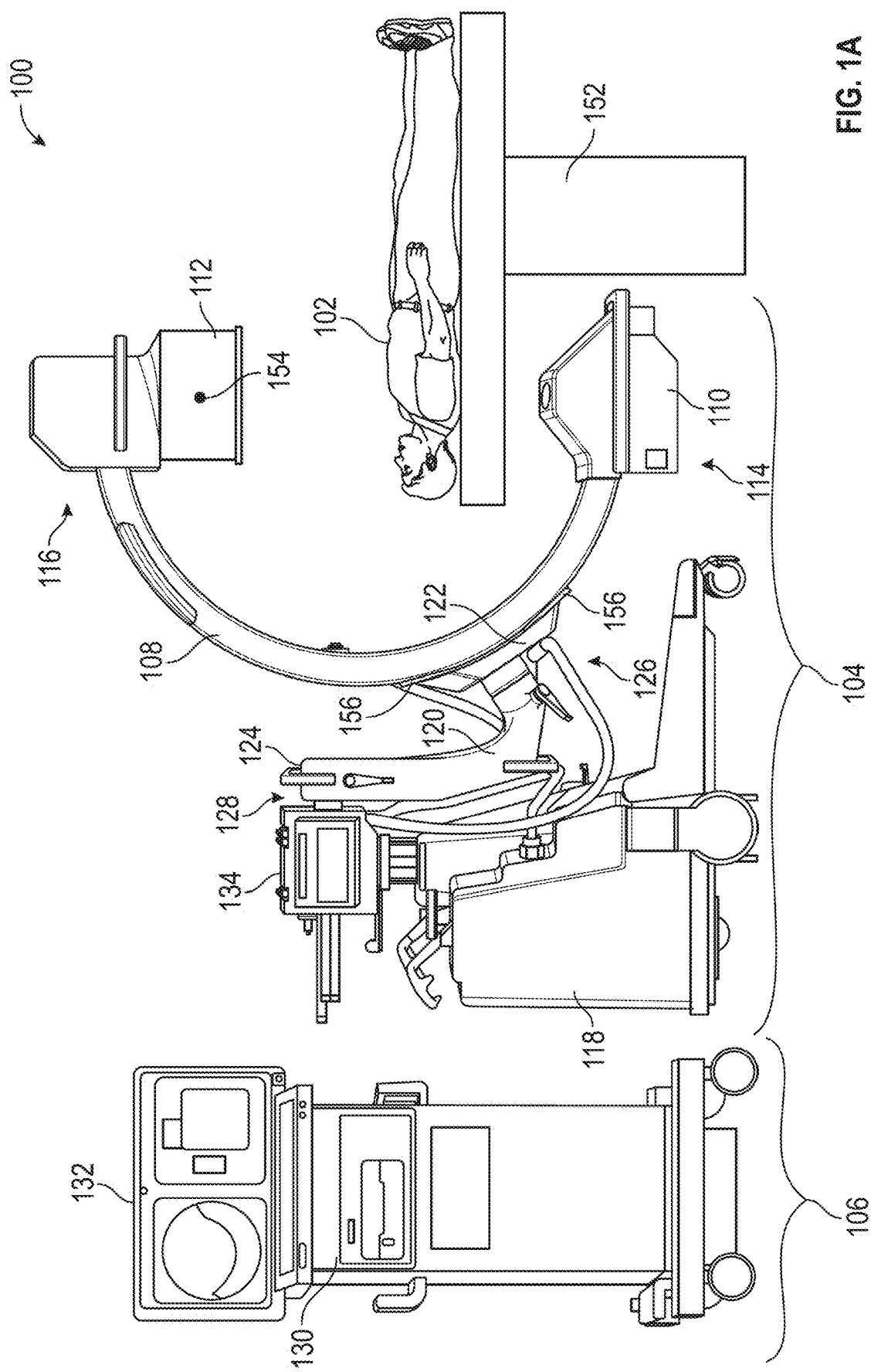
FIGS. 1A-1E illustrate a system for imaging a patient in accordance with embodiments of the present technology.

The present technology generally relates to systems, methods, and devices for medical imaging. For example, in some embodiments, the systems and methods described herein use a mobile C-arm x-ray imaging apparatus (also referred to herein as a "mobile C-arm apparatus") to generate a 3D reconstruction of a patient's anatomy using CBCT imaging techniques. Unlike conventional systems and devices that are specialized for CBCT imaging, the mobile C-arm apparatus may lack a motor and/or other automated mechanisms for rotating the imaging arm that carries the x-ray source and detector. Instead, the imaging arm is manually rotated through a series of different angles to obtain a sequence of two-dimensional (2D) projection images of the anatomy. In some situations, the manual rotation may produce undesirable movements of the imaging arm (e.g., oscillations, vibrations, shifting, flexing) that can interfere with the quality of the 3D reconstruction generated from the 2D images. Additionally, the mobile C-arm apparatus may lack sensors for obtaining pose data of the imaging arm during image acquisition, which may be needed for an accurate 3D reconstruction.

Accordingly, in some embodiments, a method for imaging an anatomic region includes receiving a plurality of 2D images of the anatomic region from a detector carried by an imaging arm of an x-ray imaging apparatus (e.g., a mobile C-arm apparatus). The 2D images can be obtained during manual rotation of the imaging arm. The imaging arm can be stabilized by a shim structure during the manual rotation to reduce or inhibit unwanted movements. The method can also include receiving sensor data indicative of a plurality of poses of the imaging arm during the manual rotation from at least one sensor coupled to the imaging arm (e.g., an inertial measurement unit (IMU)). The method can further include generating a 3D reconstruction of the anatomic region based on the 2D images and the sensor data. The 3D reconstruction can be displayed to a physician or other operator to provide image-based guidance during a medical procedure performed in the anatomic region (e.g., a biopsy or ablation procedure).

The embodiments described herein can provide many advantages over conventional imaging technologies. For example, the systems and methods herein can use a manually-rotated mobile C-arm apparatus to generate high quality CBCT images of a patient's anatomy, rather than a specialized CBCT imaging system. This approach can reduce costs and increase the availability of CBCT imaging, thus allowing CBCT imaging techniques to be used in many different types of medical procedures. For example, CBCT imaging can be used to generate intraprocedural 3D models of an anatomic region for guiding a physician in accurately positioning a tool at a target location in the anatomy, e.g., for biopsy, ablation, or other diagnostic or treatment procedures.

Embodiments of the present disclosure will be described more fully hereinafter with reference to the accompanying drawings in which like numerals represent like elements throughout the several figures, and in which example embodiments are shown. Embodiments of the claims may, however, be embodied in many different forms and should not be construed as limited to the embodiments set forth herein. The examples set forth herein are non-limiting examples and are merely examples among other possible examples.

As used herein, the terms "vertical," "lateral," "upper," and "lower" can refer to relative directions or positions of features of the embodiments disclosed herein in view of the orientation shown in the Figures. For example, "upper" or "uppermost" can refer to a feature positioned closer to the top of a page than another feature. These terms, however, should be construed broadly to include embodiments having other orientations, such as inverted or inclined orientations where top/bottom, over/under, above/below, up/down, and left/right can be interchanged depending on the orientation.

Although certain embodiments of the present technology are described in the context of medical procedures performed in the lungs, this is not intended to be limiting. Any of the embodiments disclosed herein can be used in other types of medical procedures, such as procedures performed on or in the musculoskeletal system, vasculature, abdominal cavity, gastrointestinal tract, genitourinary tract, brain, and so on. Additionally, any of the embodiments herein can be used for applications such as surgical tool guidance, biopsy, ablation, chemotherapy administration, surgery, or any other procedure for diagnosing or treating a patient.

The headings provided herein are for convenience only and do not interpret the scope or meaning of the claimed present technology.

I. Overview of Technology

Lung cancer kills more people each year than breast, prostate, and colon cancers combined. Most lung cancers are diagnosed at a late stage, which contributes to the high mortality rate. Earlier diagnosis of lung cancer (e.g., at stages 1-2) can greatly improve survival. The first step in diagnosing an early-stage lung cancer is to perform a lung biopsy on the suspicious nodule or lesion. Bronchoscopic lung biopsy is the conventional biopsy route, but typically suffers from poor success rates (e.g., only 50% to 70% of nodules are correctly diagnosed), meaning that the cancer status of many patients remains uncertain even after the biopsy procedure. One common reason for non-diagnostic biopsy is that the physician fails to place the biopsy needle into the correct location in the nodule before collecting the biopsy sample. This situation can occur due to shortcomings of conventional technologies for guiding the physician in navigating the needle to the target nodule. For example, conventional technologies typically use a static chest CT scan of the patient obtained before the biopsy procedure (e.g., days to weeks beforehand) that is registered to the patient's anatomy during the procedure (e.g., via electromagnetic (EM) navigation or shape sensing technologies). Registration errors can cause the physician to completely miss the nodule during needle placement. These errors, also known as CT-to-body divergence, occur when the preprocedural scan data does not match the patient anatomy data obtained during the actual procedure. These differences can occur because the lungs are dynamic and often change in volume from day-to-day and/or when patients are under anesthesia. Research has shown that the average error between the preprocedural CT scan and the patient's anatomy during the procedure is 1.8 cm, which is larger than many of the pulmonary nodules being biopsied.

CBCT is an imaging technique capable of producing high resolution 3D volumetric reconstructions of a patient's anatomy. For bronchoscopic lung biopsy, intraprocedural CBCT imaging can be used to confirm that the biopsy needle is positioned appropriately relative to the target nodule and has been shown to increase diagnostic accuracy by almost 20%. A typical CBCT procedure involves scanning the patient's body with a cone-shaped x-ray beam that is rotated over a wide, circular arc (e.g., 180° to 360°) to obtain a sequence of 2D projection images. A 3D volumetric reconstruction of the anatomy can be generated from the 2D images using image reconstruction techniques such as filtered backprojection or iterative reconstruction. Conventional CBCT imaging systems include a motorized imaging arm for automated, highly-controlled rotation of the x-ray source and detector over a smooth, circular arc during image acquisition. These systems are also capable of accurately tracking the pose of the imaging arm across different rotation angles. However, CBCT imaging systems are typically large, extremely expensive, and may not be available to many physicians, such as pulmonologists performing lung biopsy procedures.

Manually-operated mobile C-arm apparatuses are less expensive and more readily available than specialized CBCT imaging systems, but are generally unsuitable for CBCT imaging for some or all of the following reasons. First, mobile C-arm apparatuses typically lack a motorized imaging arm and thus must be manually rotated during imaging acquisition. However, with manual rotation, it is extremely difficult to produce a smooth, isocentric, circular motion of the imaging arm over sufficiently large angles (e.g., greater than 90°) for CBCT imaging. Due to mechanical instabilities present in many mobile C-arm apparatuses, the imaging arm may exhibit unwanted movements (e.g., oscillations, vibrations, shifts, flexing) during manual rotation, which may cause the imaging arm to move along a non-circular trajectory or otherwise detrimentally affect the quality of the resulting 3D reconstruction. Second, mobile C-arm apparatuses generally lack the capability to accurately determine the pose of the imaging arm as the imaging arm rotates around the patient. In a typical CBCT imaging procedure, hundreds of images are acquired at a rate of 10-50 images per second, and the pose of the imaging arm needs to be determined for each image. Third, mobile C-arm apparatuses often use an image intensifier as the x-ray detector, which can create significant distortion artifacts that prevent accurate image reconstruction. Image intensifiers are also relatively heavy (e.g., hundreds of pounds) and thus may further destabilize the imaging arm during manual rotation.

Tomosynthesis is a technique that may be used to generate intraprocedural images of patient anatomy. However, because tomosynthesis uses a much smaller rotation angle during image acquisition (e.g., 15° to 70°), the resulting images are typically low resolution, lack sufficient depth information, and/or may include significant distortion.

Tomosynthesis is therefore typically not suitable for applications requiring highly accurate 3D spatial information.

Accordingly, there is a need for imaging techniques that are capable of producing intraprocedural, high resolution 3D representations of a patient's anatomy using low-cost, accessible imaging systems such as mobile C-arm apparatuses. The present technology can address these and other challenges by providing systems, methods, and devices for performing CBCT imaging using a manually-rotated imaging apparatus, also referred to herein as "manually-rotated CBCT" or "mrCBCT." For example, in some embodiments, the systems described herein mechanically stabilize the imaging arm and/or other components of the mobile C-arm apparatus using one or more shim structures (e.g., wedges, blocks, dampers, etc.) that reduce or prevent unwanted movements during manual rotation. The system can also include one or more lever structure (e.g., a detachable or permanently affixed handle) to assist the operator in rotating the imaging arm from locations that are less likely to produce unwanted movements. The system can further include at least one sensor (e.g., a motion sensor such as an IMU) that automatically tracks the pose of the imaging arm during rotation. The sensor data can be temporally synchronized to the obtained 2D projection images to accurately determine the pose of the imaging arm for each image. In some embodiments, the system is calibrated before and/or during use to correct image distortion (e.g., from the image intensifier), determine calibration parameters to compensate for mechanical differences between individual mobile C-arm apparatuses, and/or adjust for variations in how the operator manually rotates the imaging arm. The approaches described herein can be used to adapt a manually-operated mobile C-arm apparatus for CBCT imaging, thus allowing high quality CBCT reconstructions to be produced using relatively inexpensive and accessible imaging equipment.

II. Medical Imaging Systems and Associated Devices and Methods

FIG. 1A is a partially schematic illustration of a system 100 for imaging a patient 102 in accordance with embodiments of the present technology. The system 100 includes an imaging apparatus 104 operably coupled to a console 106. The imaging apparatus 104 can be any suitable device configured to generate images of a target anatomic region of the patient 102, such as an x-ray imaging apparatus. In the illustrated embodiment, for example, the imaging apparatus 104 is a mobile C-arm apparatus configured for fluoroscopic imaging. A mobile C-arm apparatus typically includes a manually-movable imaging arm 108 configured as a curved, C-shaped gantry (also known as a "C-arm"). Examples of mobile C-arm apparatuses include, but are not limited to, the OEC 9900 Elite (GE Healthcare) and the BV Pulsera (Philips). In other embodiments, however, the techniques described herein can be adapted to other types of imaging apparatuses 104 having a manually-movable imaging arm 108, such as a G-arm imaging apparatus.

The imaging arm 108 can carry a radiation source 110 (e.g., an x-ray source) and a detector 112 (e.g., an x-ray detector such as an image intensifier or flat panel detector). The radiation source 110 can be mounted at a first end portion 114 of the imaging arm 108, and the detector 112 can be mounted at a second end portion 116 of the imaging arm 108 opposite the first end portion 114. During a medical procedure, the imaging arm 108 can be positioned near the patient 102 such that the target anatomic region is located between the radiation source 110 and the detector 112. The imaging arm 108 can be rotated to a desired pose (e.g., angle) relative to the target anatomic region. The radiation source 110 can output radiation (e.g., x-rays) that travels through the patient's body to the detector 112 to generate 2D images of the anatomic region (also referred to herein as "projection images"). The image data can be output as still or video images. In some embodiments, the imaging arm 108 is rotated through a sequence of different poses to obtain a plurality of 2D projection images. The images can be used to generate a 3D representation of the anatomic region (also referred to herein as a "3D reconstruction," "volumetric reconstruction," "image reconstruction," or "CBCT reconstruction"). The 3D representation can be displayed as a 3D model or rendering, and/or as one or more 2D image slices (also referred to herein as "CBCT images" or "reconstructed images").

In some embodiments, the imaging arm 108 is coupled to a base 118 by a support arm 120. The base 118 can act as a counterbalance for the imaging arm 108, the radiation source 110, and the detector 112. As shown in FIG. 1A, the base 118 can be a mobile structure including wheels for positioning the imaging apparatus 104 at various locations relative to the patient 102. In other embodiments, however, the base 118 can be a stationary structure. The base 118 can also carry various functional components for receiving, storing, and/or processing the image data from the detector 112, as discussed further below.

The support arm 120 (also referred to as an "attachment arm" or "pivot arm") can connect the imaging arm 108 to the base 118. The support arm 120 can be an elongate structure having a distal portion 122 coupled to the imaging arm 108, and a proximal portion 124 coupled to the base 118. Although the support arm 120 is depicted in FIG. 1A as being an L-shaped structure ("L-arm") having a vertical section and a horizontal section, in other embodiments the support arm 120 can have a different shape (e.g., a curved shape).

Figure 1B:
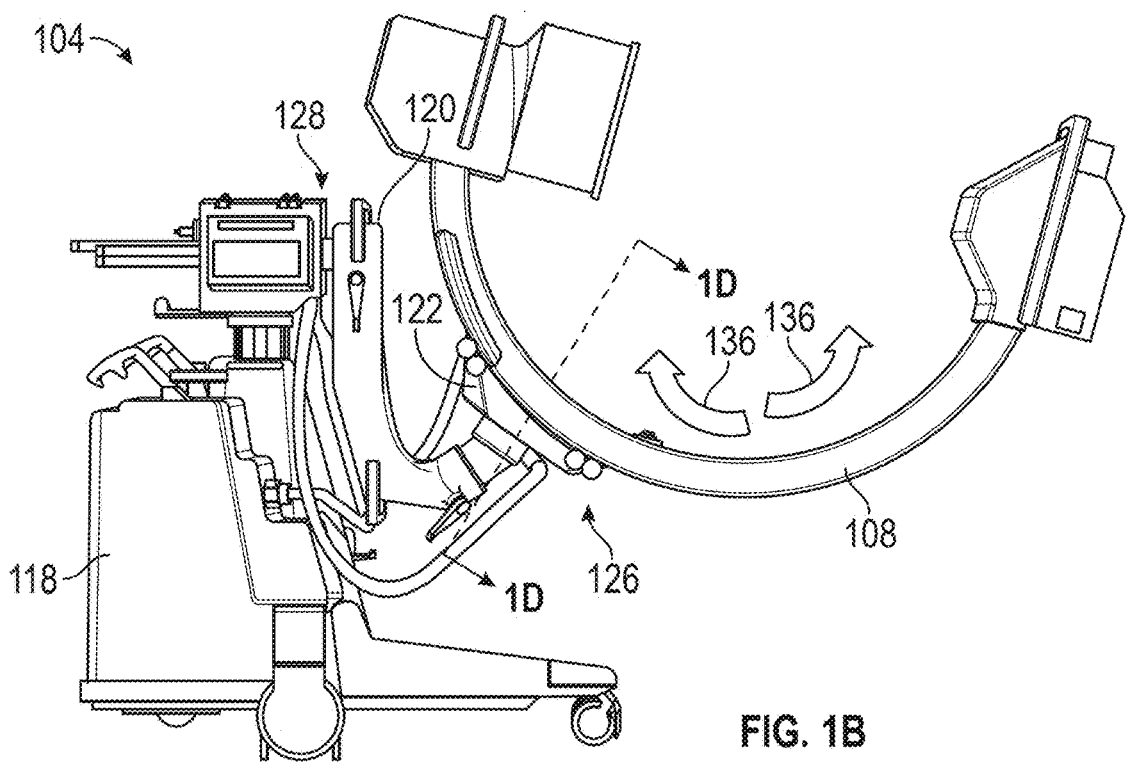

The imaging arm 108 can be configured to rotate in multiple directions relative to the base 118. For example, FIG. 1B is a partially schematic illustration of the imaging apparatus 104 during an orbital rotation. As shown in FIG. 1B, during an orbital rotation, the imaging arm 108 rotates relative to the support arm 120 and base 118 along a lengthwise direction as indicated by arrows 136. Thus, during an orbital rotation, the motion trajectory can be located primarily or entirely within the plane of the imaging arm 108. The imaging arm 108 can be slidably coupled to the support arm 120 to allow for orbital rotation of the imaging arm 108. For example, the imaging arm 108 can be connected to the support arm 120 via a first interface 126 that allows the imaging arm 108 to slide along the support arm 120.

Figure 1C:
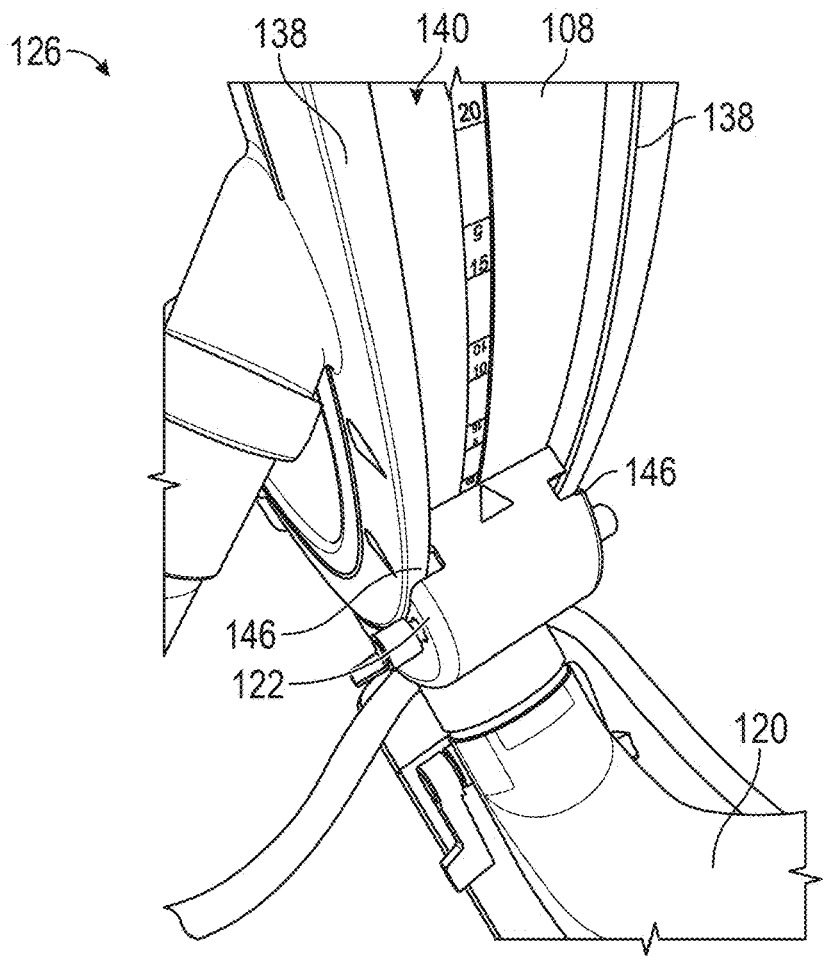
Figure 1D:
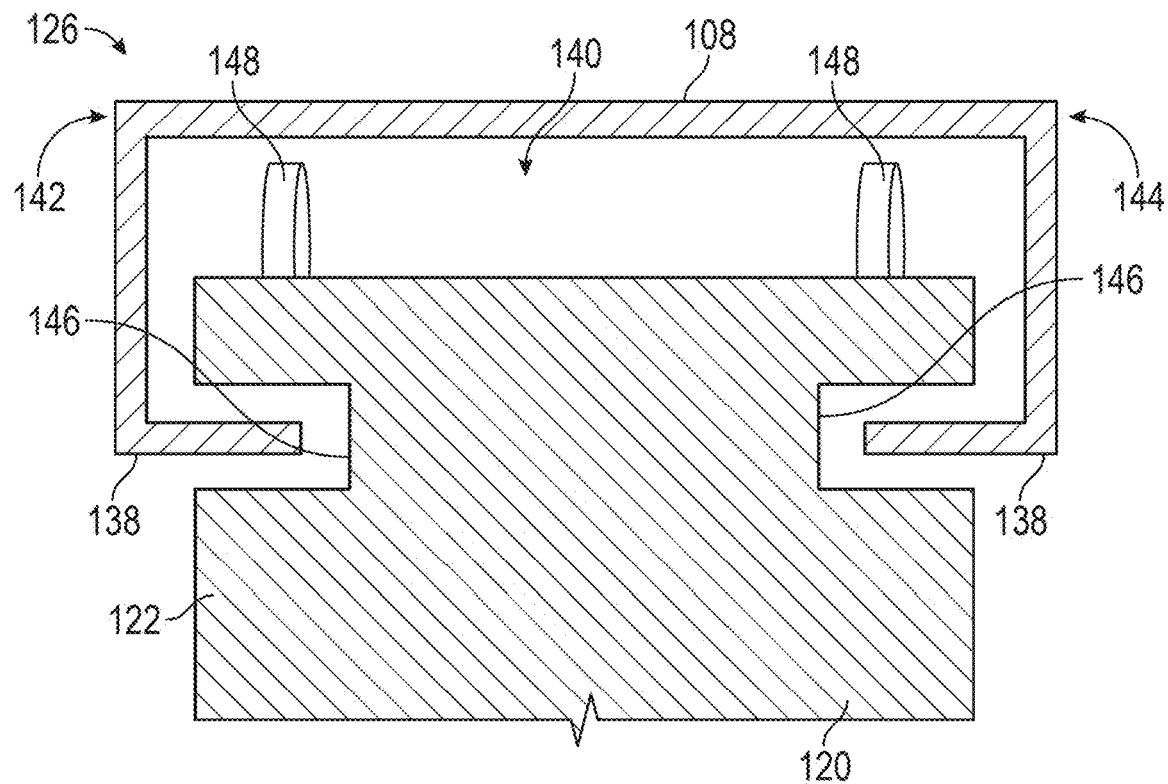

FIG. 1C is a perspective view of the first interface 126, and FIG. 1D is a partially schematic cross-sectional view of the first interface 126 along axis A-A in FIG. 1B. Referring to FIGS. 1C and 1D together, the imaging arm 108 can include a pair of rails 138 and a recessed track 140 between the rails 138. The rails 138 can be located at opposite sides (e.g., a first side 142 and a second side 144) of the first interface 126. The distal portion 122 of the support arm 120 can fit between the rails 138 and at least partially into the track 140. The rails 138, track 140, and distal portion 122 can collectively form the first interface 126. As best seen in FIG. 1D, the distal portion 122 can include a pair of grooves or notches 146 that engage the rails 138 to secure the distal portion 122 to the track 140. The distal portion 122 can also include one or more wheels or rollers 148 that contact the inner surface of the track 140 so that the imaging arm 108 can slide smoothly relative to the support arm 120 during orbital rotation.

Figure 1E:
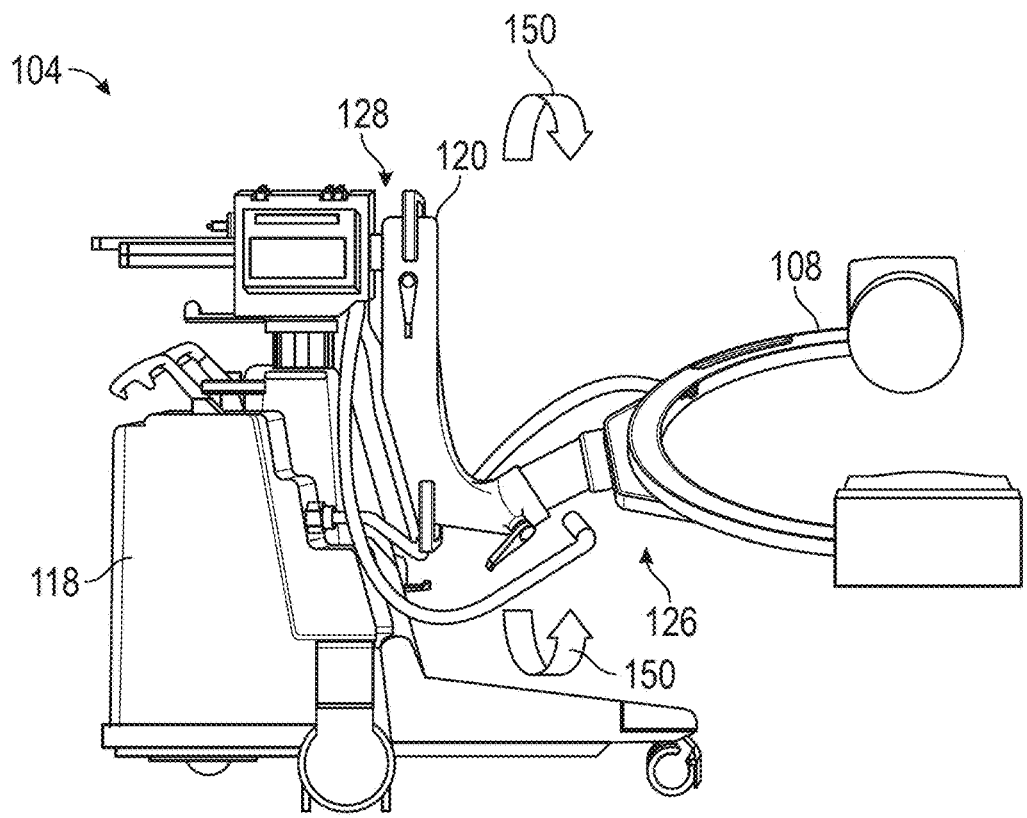

FIG. 1E is a partially schematic illustration of the imaging apparatus 104 during a propeller rotation (also known as "angular rotation" or "angulation"). As shown in FIG. 1E, during a propeller rotation, the imaging arm 108 and support arm 120 rotate relative to the base 118 in a lateral direction as indicated by arrows 150. The support arm 120 can be rotatably coupled to the base 118 via a second interface 128 (e.g., a pivoting joint or other rotatable connection) that allows the imaging arm 108 and support arm 120 to turn relative to the base 118. Optionally, the imaging apparatus 104 can include a locking mechanism to prevent orbital rotation while the imaging arm 108 is performing a propeller rotation, and/or to prevent propeller rotation while the imaging arm 108 is performing an orbital rotation.

Referring again to FIG. 1A, the imaging apparatus 104 can optionally be configured to rotate in other directions, alternatively or in addition to orbital rotation and/or propeller rotation. For example, in some embodiments, the imaging arm 108 and the distal portion 122 of the support arm 120 are rotatable relative to the rest of the support arm 120 and the base 118 (also known as "flip-flop" rotation). A flip-flop rotation may be advantageous in some situations for reducing interference with other components located near the operating table 152 (e.g., a surgical robotic assembly).

The imaging apparatus 104 can be operably coupled to a console 106 for controlling the operation of the imaging apparatus 104. As shown in FIG. 1A, the console 106 can be a mobile structure with wheels, thus allowing the console 106 to be moved independently of the imaging apparatus 104. In other embodiments, however, the console 106 can be a stationary structure. The console 106 can be attached to the imaging apparatus 104 by wires, cables, etc., or can be a separate structure that communicates with the imaging apparatus 104 via wireless communication techniques. The console 106 can include a computing device 130 (e.g., a workstation, personal computer, laptop computer, etc.) including one or more processors and memory configured to perform various operations related to image acquisition and/or processing. For example, the computing device 130 can perform some or all of the following operations: receive, organize, store, and/or process data (e.g., image data, sensor data, calibration data) relevant to generating a 3D reconstruction; execute image reconstruction algorithms; execute calibration algorithms; and post-process, render, and/or display the 3D reconstruction. Additional examples of operations that may be performed by the computing device 130 are described in greater detail elsewhere herein.

The computing device 130 can receive data from various components of the system 100. For example, the computing device 130 can be operably coupled to the imaging apparatus 104 (e.g., to radiation source 110, detector 112, and/or base 118) via wires and/or wireless communication modalities (e.g., Bluetooth, WiFi) so that the computing device 130 can transmit commands to the imaging apparatus 104 and/or receive data from the imaging apparatus 104. In some embodiments, the computing device 130 transmits commands to the imaging apparatus 104 to cause the imaging apparatus 104 to start acquiring images, stop acquiring images, adjust the image acquisition parameters, and so on. The imaging apparatus 104 can transmit image data (e.g., the projection images acquired by the detector 112) to the computing device 130. The imaging apparatus 104 can also transmit status information to the computing device 130, such as whether the components of the imaging apparatus 104 are functioning properly, whether the imaging apparatus 104 is ready for image acquisition, whether the imaging apparatus 104 is currently acquiring images, etc.

Optionally, the computing device 130 can also receive other types of data from the imaging apparatus 104. In the embodiment of FIG. 1A, for example, the imaging apparatus 104 includes at least one sensor 154 configured to generate sensor data indicative of a pose of the imaging arm 108. The sensor data can be transmitted to the computing device 130 via wired or wireless communication for use in the image processing techniques described herein. Additional details of the configuration and operation of the sensor 154 are provided below.

The console 106 can include various user interface components allowing an operator (e.g., a physician, nurse, technician, or other healthcare professional) to interact with the computing device 130. For example, the operator can input commands to the computing device 130 via a suitable input device (e.g., a keyboard, mouse, joystick, touchscreen, microphone). The console 106 can also include a display 132 (e.g., a monitor or touchscreen) for outputting image data, sensor data, reconstruction data, status information, control information, and/or any other suitable information to the operator. Optionally, the base 118 can also include a secondary display 134 for outputting information to the operator.

Although FIG. 1A shows the console 106 as being separate from the imaging apparatus 104, in other embodiments the console 106 can be physically connected to the imaging apparatus 104 (e.g., to the base 118), such as by wires, cables, etc. Additionally, in other embodiments, the base 118 can include a respective computing device and/or input device, such that the imaging apparatus 104 can also be controlled from the base 118. In such embodiments, the computing device located in the base 118 can be configured to perform any of the image acquisition and/or processing operations described herein. Optionally, the console 106 can be integrated with the base 118 (e.g., the computing device 130 is located in the base 118) or omitted altogether such that the imaging apparatus 104 is controlled entirely from the base 118. In some embodiments, the system 100 includes multiple consoles 106 (e.g., at least two consoles 106), each with a respective computing device 130. Any of the processes described herein can be performed on a single console 106 or across any suitable combination of multiple consoles 106.

A. Stabilization Devices and Methods

Referring again to FIG. 1A, the system 100 can be used to perform an imaging procedure in which an operator manually rotates the imaging arm 108 during imaging acquisition, such as an mrCBCT procedure. In such embodiments, the imaging apparatus 104 can be a manually-operated device that lacks any motors or other actuators for automatically rotating the imaging arm 108. For example, one or both of the first interface 126 and second interface 128 can lack any automated mechanism for actuating orbital rotation and propeller rotation of the imaging arm 108, respectively. Instead, the user manually applies the rotational force to the imaging arm 108 and/or support arm 120 during the mrCBCT procedure.

In some embodiments, the imaging procedure involves performing a propeller rotation of the imaging arm 108. Propeller rotation may be advantageous for mrCBCT or other imaging techniques that involve rotating the imaging arm 108 over a relatively large rotation angle. For example, a mrCBCT or similar imaging procedure can involve rotating the imaging arm 108 over a range of at least 90°, 100°, 110°, 120°, 130°, 140°, 150°, 160°, 170°, 180°, 190°, 200°, 210°, 220°, 230°, 240°, 250°, 260°, 270°, 280°, 290°, 300°, 310°, 320°, 330°, 340°, 350°, or 360°. The total rotation can be within a range from 90° to 360°, 90° to 270°, 90° to 180°, 120° to 360°, 120° to 270°, 120° to 180°, 180° to 360°, or 180° to 270°. As previously discussed, the large rotation angle may be required for capturing a sufficient number of images from different angular or rotational positions to generate an accurate, high resolution 3D reconstruction of the anatomy. In many situations, it is not possible to achieve such large rotation angles using orbital rotation. For example, as shown in FIG. 1A, if the imaging apparatus 104 is positioned at one end of the patient's body (e.g., near the head and/or torso of the patient 102), the orbital rotation of the imaging arm 108 may be constrained by the location of the patient 102 and/or the operating table 152 to a relatively limited rotation angle (e.g., less than 90°).

Larger rotation angles can be achieved with propeller rotation, even in the configuration shown in FIG. 1A. However, propeller rotation can be less mechanically stable than orbital rotation, particularly when the rotational force is applied manually. Accordingly, in the absence of stabilization mechanisms (e.g., when shim structures 156 are omitted), the imaging arm 108 may exhibit unwanted movements during a manual propeller rotation that can detrimentally affect the quality of the resulting CBCT reconstruction. Examples of unwanted movements that can occur include, but are not limited to, oscillations, vibrations, sudden shifts, flexing, and/or other non-uniform motions that cause the imaging arm 108 to deviate from the desired trajectory (e.g., a smooth, single plane, isocentric, and/or circular trajectory). Unwanted movements can occur, for example, due to mechanical instability of the imaging apparatus 104 such as a weight imbalance between the radiation source 110 and detector 112, as well as mechanical laxity in the first interface 126 and/or second interface 128. In some embodiments, the detector 112 is much heavier than the radiation source 110 (e.g., an image intensifier can weigh hundreds of pounds). As a result, during propeller rotation, the imaging arm 108 can shift with respect to the support arm 120, and/or the support arm 120 can shift with respect to the base 118. Such movements can cause the center of rotation of the imaging arm 108 to move during image acquisition, which can cause the projection images obtained by the detector 112 to be misaligned. The 3D reconstruction produced from such misaligned projection images may include significant image artifacts and/or may lack sufficient spatial resolution for use in many medical procedures.

Figure 2A:
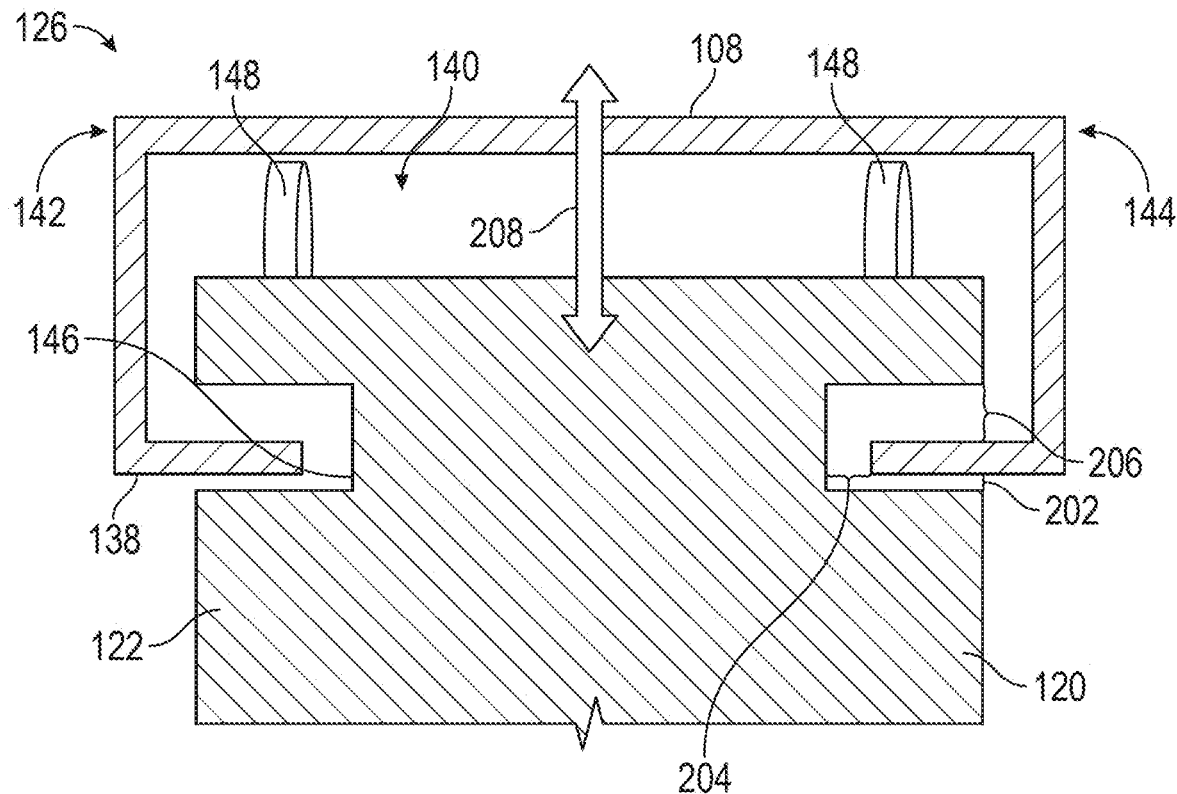
FIGS. 2A and 2B illustrate examples of unwanted movements that may occur with a manually-operated imaging apparatus.
Figure 2B:
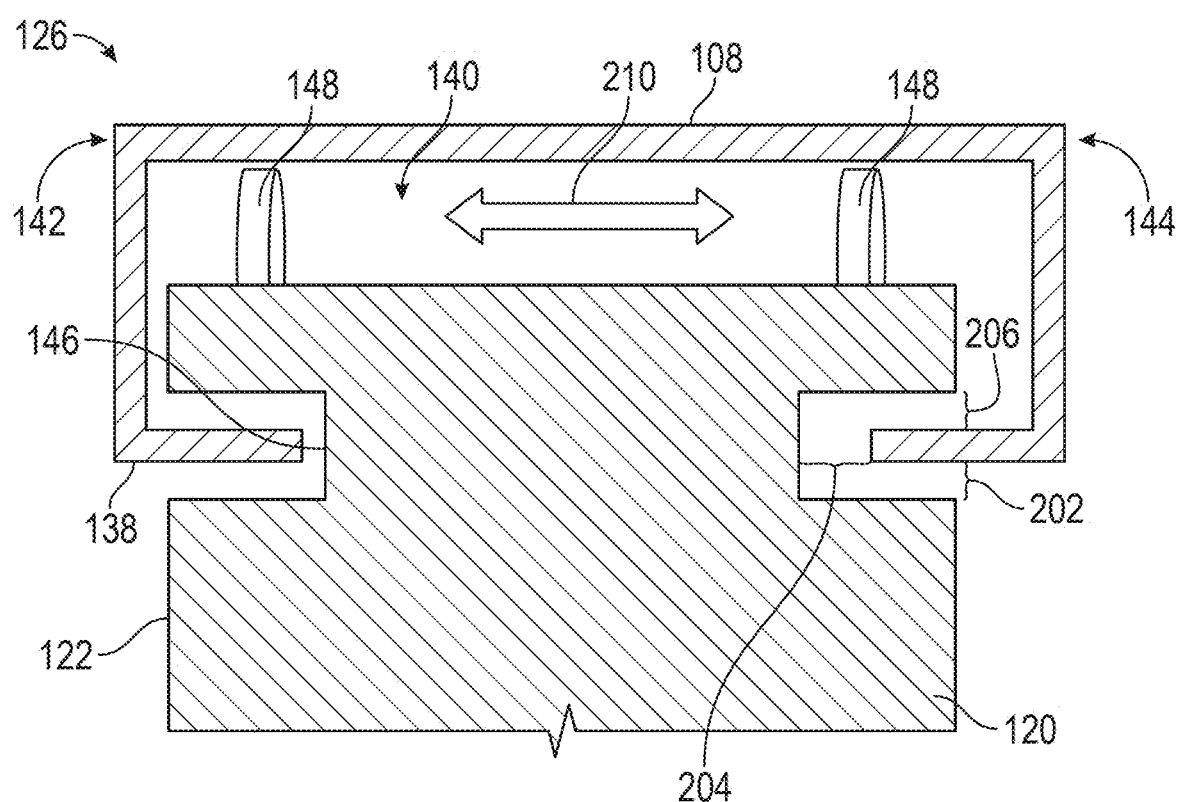

FIGS. 2A and 2B illustrate examples of unwanted movements that may occur at the first interface 126 during a manual propeller rotation of the imaging arm 108, in the absence of stabilization mechanisms. Referring to FIGS. 2A and 2B together, the first interface 126 can include spaces, gaps, etc., between the various components of the imaging arm 108 and support arm 120 (e.g., between the rails 138, track 140, distal portion 122, grooves 146, and/or wheels 148). This mechanical laxity can allow the imaging arm 108 and support arm 120 to shift relative to each other, even when the imaging arm 108 is locked to prevent orbital rotation. For example, the first and second sides 142, 144 of the first interface 126 can each include a first gap 202, second gap 204, and/or third gap 206. The gaps 202-204 can be located between the rail 138 of the imaging arm 108 and the groove 146 in the distal portion 122 of the support arm 120 (in FIGS. 2A and 2B, the gaps 202-204 are labeled only on the second side 144 merely for purposes of simplicity). In the illustrated embodiment, the first gap 202 is between a lower surface of the rail 138 and an upper surface of the groove 146 and, the second gap 204 is between a lateral surface of the rail 138 and a lateral surface of the groove 146, and the third gap 206 is between a lower surface of the rail 138 and an upper surface of the groove 146. Due to the presence of the gaps 202-206, the imaging arm 108 can shift in a vertical direction 208 (FIG. 2A) and/or a lateral direction 210 (FIG. 2B) relative to the support arm 120.

Referring again to FIG. 1A, in some embodiments, the system 100 includes features for reducing or preventing unwanted movements that may occur during a mrCBCT procedure. For example, the system 100 can include one or more shim structures 156 for mechanically stabilizing certain portions of the imaging apparatus 104 (the shim structures 156 are omitted in FIGS. 1B-1E merely for purposes of simplicity). The shim structures 156 can be removable or permanent components that are coupled to the imaging apparatus 104 at one or more locations to reduce or prevent unwanted movements during a manual rotation. In the illustrated embodiment, the system 100 includes two shim structures 156 positioned at opposite ends of the first interface 126 between the imaging arm 108 and the support arm 120. Optionally, the system 100 can include four shim structures 156, one at each end of the first interface 126 and on both sides 142, 144 of the first interface 126. Alternatively or in combination, the system 100 can include one or more shim structures 156 at other locations of the imaging apparatus 104 (e.g., at the second interface 128). Any suitable number of shim structures 156 can be used, such as one, two, three, four, five, six, seven, eight, nine, ten, 11, 12, or more shim structures.

The shim structures 156 disclosed herein can make it easier for a user to produce a smooth, uniform movement of the imaging arm 108 over a wide rotation angle without using motors or other automated actuation mechanisms. Accordingly, the projection images generated by the detector 112 can exhibit significantly reduced misalignment compared to projection images generated without the shim structures 156, thus improving the accuracy and resolution of the resulting 3D reconstruction. The shim structures 156 can also produce a more consistent rotation path of the imaging arm 108, which can significantly improve the accuracy of the calibration processes disclosed herein. Additional examples and features of shim structures 156 that can be used with the imaging apparatus 104 are described in greater detail below in connection with FIGS. 3A-10D.

FIGS. 3A-10D illustrate representative examples of shim structures that can be used to stabilize an imaging apparatus, in accordance with embodiments of the present technology. Although the shim structures of FIGS. 3A-10D are described and illustrated with reference to components of the imaging apparatus 104 of FIG. 1A, it will be appreciated that the shim structures can also be used with other imaging apparatuses and systems. Additionally, any of the features of the shim structures of FIGS. 3A-10D can be combined with each other.

Figure 3A:
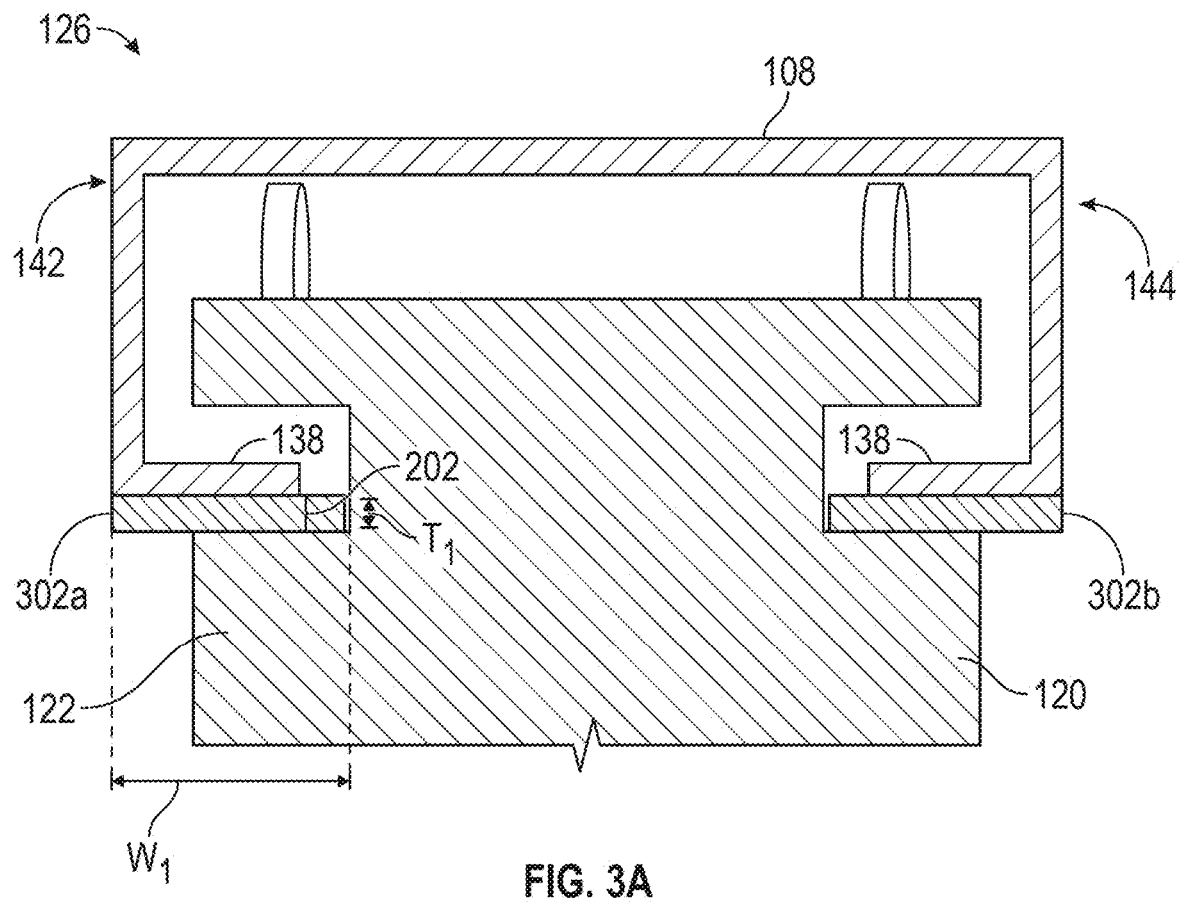
FIGS. 3A and 3B illustrate a set of shim structures configured in accordance with embodiments of the present technology.

FIG. 3A is a partially schematic cross-sectional view of the first interface 126 with a set of shim structures 302a, 302b configured in accordance with embodiments of the present technology. Referring first to FIG. 3A, the shim structures 302a, 302b can be used to stabilize the first interface 126 between the imaging arm 108 and support arm 120 of the imaging apparatus 104. In the illustrated embodiment, the shim structures 302a, 302b are positioned at the first and second sides 142, 144, respectively, of the first interface 126. The shim structures 302a, 302b can fit within the first gaps 202 between the imaging arm 108 and the support arm 120. The shim structures 302a, 302b can partially or completely fill the first gaps 202, thus inhibiting or reducing unwanted movement of the imaging arm 108 relative to the support arm 120 when the imaging arm 108 is manually rotated. In some embodiments, the shim structures 302a, 302b are removable components that are temporarily inserted into the first interface 126 to stabilize the imaging arm 108 and support arm 120 during manual operation. The shim structures 302a, 302b can be held in place by friction and/or mechanical interference, or by other mechanisms. In other embodiments, however, the shim structures 302a, 302b can be permanently affixed within the first interface 126.

Figure 3B:
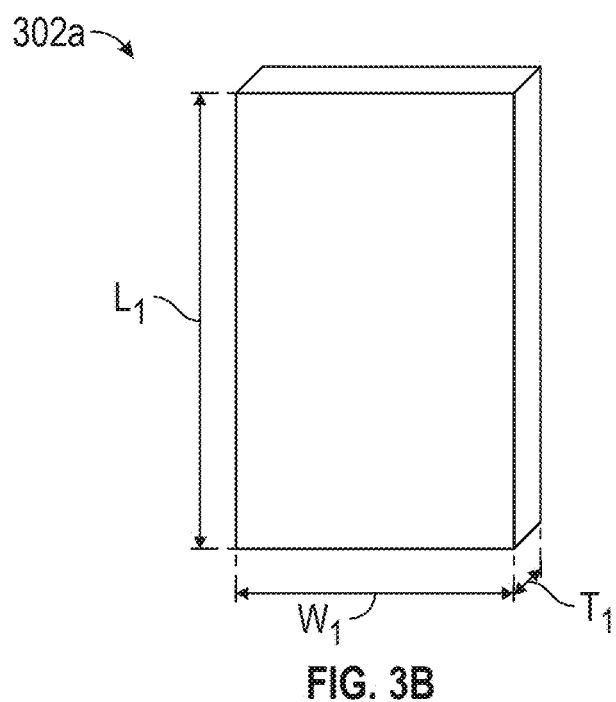

FIG. 3B is a perspective view of an individual shim structure 302a. The shim structure 302a can be an elongate member (e.g., a block, wedge, panel) configured to fill a space between the imaging arm 108 and the support arm 120. The shim structure 302a can be made of any material suitable for dampening, obstructing, or otherwise preventing movement of the imaging arm 108 relative to the support arm 120, including rigid or compliant materials. The geometry of the shim structure 302a can also be varied as desired. In the illustrated embodiment, for example, the shim structure 302a has a rectangular shape. In other embodiments, the shim structure 302a can have any other suitable shape, such as square, trapezoidal, triangular, circular, oval, etc. The dimensions of the shim structure 302a can be configured to provide a desired fit between the imaging arm 108 and the support arm 120. For example, the shim structure 302a can have a length $L_1$ within a range from 1 cm to 20 cm, a width $W_1$ within a range from 0.3 cm to 5 cm, and a thickness $T_1$ within a range from 1 mm to 15 mm. The thickness $T_1$ can be equal or approximately equal to the height of the first gap 202 (FIG. 3A), and the length $L_1$ and width $W_1$ can be greater than or equal to the lateral dimensions of the first gap 202.

The shim structure 302b can be identical or generally similar to the shim structure 302a. For example, the shim structures 302a, 302b can both have the same geometry (e.g., size, shape). In other embodiments, however, the shim structure 302b can have a different geometry than the shim structure 302a, e.g., the shim structure 302b can be larger or smaller than the shim structure 302a, can have a different shape than the shim structure 302a, etc. Optionally, either the shim structure 302a or shim structure 302b can be omitted, such that only one of the sides of the first interface 126 includes a shim structure.

Figure 3C:
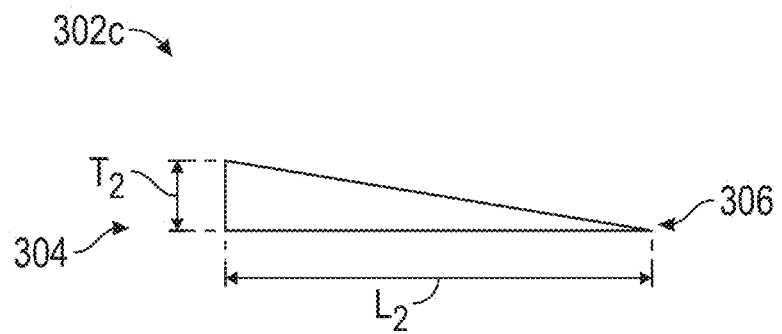
FIGS. 3C and 3D illustrate shim structures having variable thicknesses in accordance with embodiments of the present technology.

FIG. 3C is a side view of a shim structure 302c having a variable thickness $T_2$, in accordance with embodiments of the present technology. The shim structure 302c can be generally similar to the shim structure 302a and/or shim structure 302b, except that the thickness $T_2$ of the shim structure 302c decreases along the length $L_2$ of the shim structure 302c, such that the shim structure 302c is thicker at a first end region 304 and thinner at a second end region 306. In the illustrated embodiment, for example, the shim structure 302c has a triangular cross-sectional shape, with the angle of the shim structure 302c at the second end region 306 being less than or equal to 80°, 70°, 60°, 50°, 45°, 40°, 35°, 30°, 25°, 20°, 15°, 10°, or 5°.

Figure 3D:
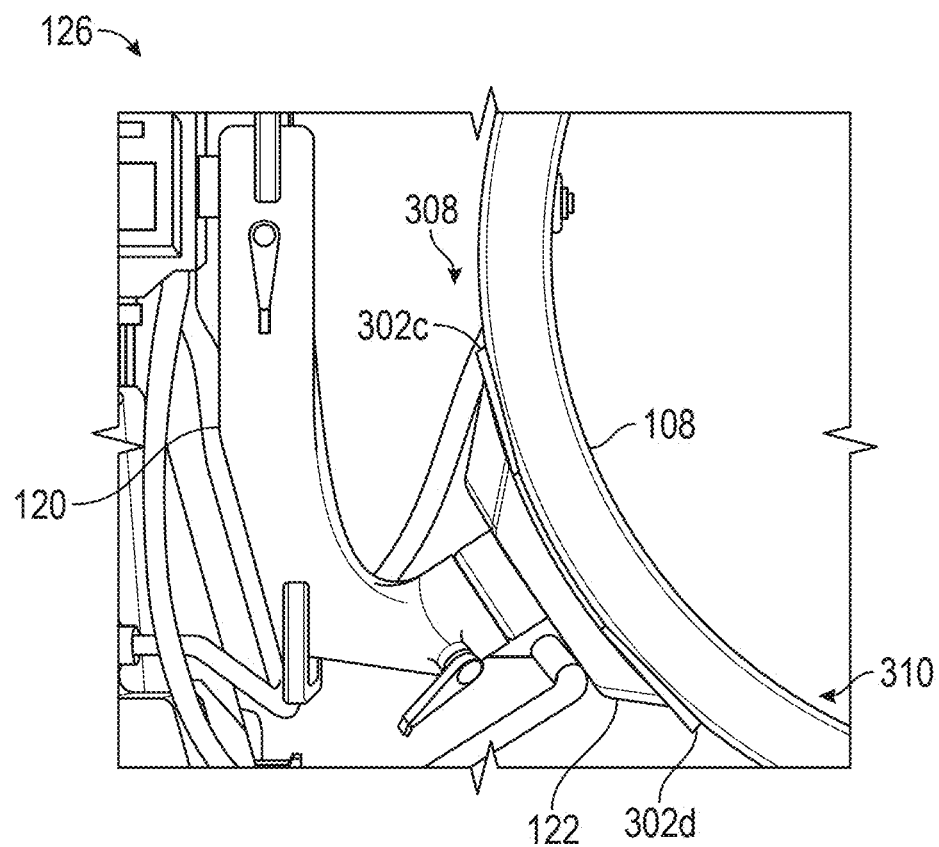

FIG. 3D is a partially schematic side view of a set of shim structures 302c, 302c positioned at the first interface 126 in accordance with embodiments of the present technology. In the illustrated embodiment, the shim structure 302d has tapered, wedge-like shape identical or similar to the shim structure 302c. In other embodiments, however, either or both of the shim structures 302c, 302d can be replaced with a shim structure having a different shape, such as the rectangular shape of the shim structure 302a of FIG. 3B. As shown in FIG. 3D, the shim structures 302c, 302d can be inserted into the spaces at the first and second ends 308, 310, respectively, of the first interface 126 between the distal portion 122 of the support arm 120 and the imaging arm 108. Although FIG. 3D shows two shim structures 302c, 302d, in some embodiments, the first interface 126 can include a total of four shim structures: two shim structures at both sides 142, 144 of the first end 308, and two shim structures at both sides 142, 144 of the second end 310.

Figure 4A:
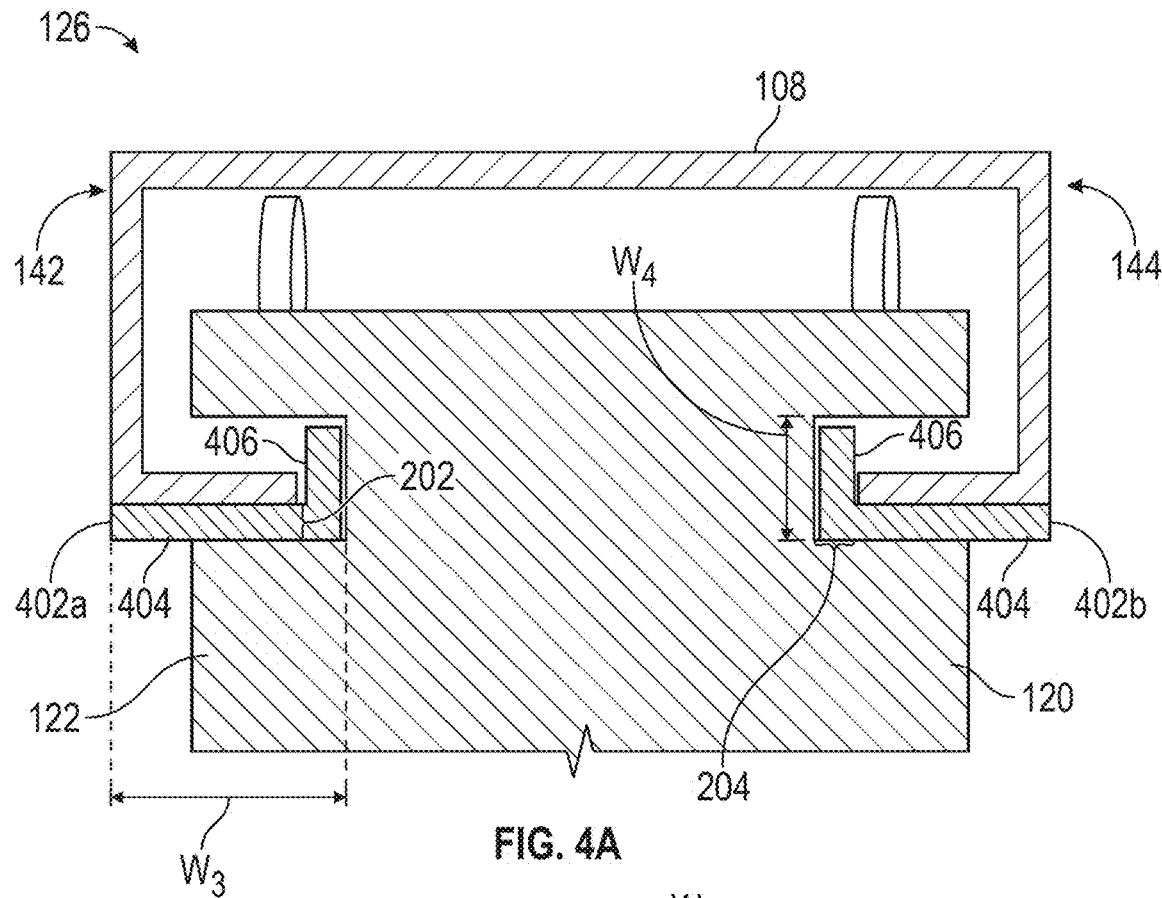
FIGS. 4A and 4B illustrate a set of L-shaped shim structures configured in accordance with embodiments of the present technology.
Figure 4B:
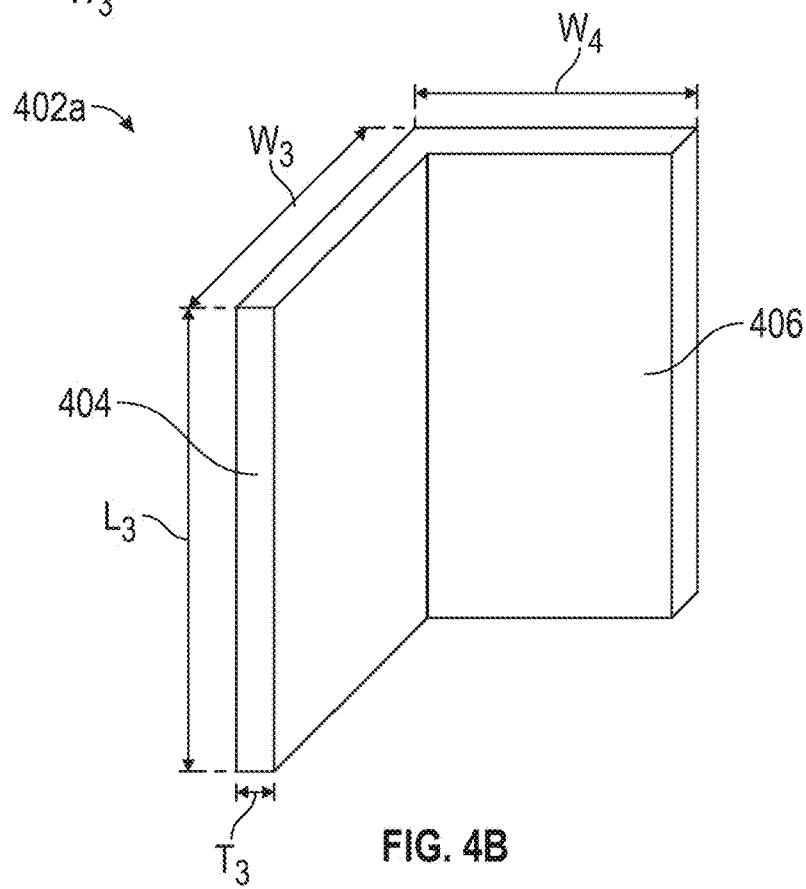

FIG. 4A is a partially schematic cross-sectional view of the first interface 126 with a set of L-shaped shim structures 402a, 402b, and FIG. 4B is a perspective view of an individual shim structure 402a, in accordance with embodiments of the present technology. Referring to FIGS. 4A and 4B together, the shim structures 402a, 402b can be inserted between the imaging arm 108 and the support arm 120 at the first and second sides 142, 144 of the first interface 126, respectively. The shim structures 402a, 402b can each include a first panel 404 connected to a second panel 406 to form an L-shaped structure. The first panel 404 and second panel 406 can fit in the first gap 202 and second gap 204, respectively, between the imaging arm 108 and the support arm 120. The first and second panels 404, 406 can be integrally formed with each other as a single unitary component, or can be separate components that are coupled to each other via adhesives, bonding, fasteners, etc. In the illustrated embodiment, the first and second panels 404, 406 are connected in a fixed geometry and are not movable relative to each other. In other embodiments, however, the first and second panels 404, 406 can be movably coupled to each other, as described further below.

The first and second panels 404, 406 can each be flattened, elongate members having a geometry (e.g., size, shape) selected to conform to the shape of the first and second gaps 202, 204. For example, the angle between the first and second panels 404, 406 can be greater than or equal to 10°, 20°, 30°, 40°, 45°, 50°, 60°, 70°, 80°, 90°, 100°, 110°, 120°, 130°, 140°, 150°, 160°, or 170°. The first and second panels 404, 406 can each have any suitable shape, such as rectangular, square, etc. The dimensions of the first and second panels 404, 406 can also be varied as desired. In the illustrated embodiment, for example, the first and second panels 404, 406 have the same length $L_3$ (e.g., within a range from 1 cm to 20 cm) and thickness $T_3$ (e.g., within a range from 1 mm to 15 mm), but have different widths $W_3$ and $W_4$, respectively. The width $W_3$ of the first panel 404 can be greater than the width $W_4$ of the second panel 406. For example, the width $W_3$ can be within a range from 0.3 cm to 5 cm, and the width $W_4$ can be within a range from 0.1 cm to 3 cm. In other embodiments, however, the width $W_3$ of the first panel 404 can be less than or equal to the width $W_4$ of the second panel 406. The first and second panels 404, 406 can also have different lengths and/or thicknesses. Additionally, although the first and second panels 404, 406 are both depicted as having a uniform thickness $T_3$, in other embodiments, the first and/or second panels 404, 406 can instead have a variable thickness (e.g., a tapered thickness similar to the shim structure 302c of FIG. 3C).

Figure 4C:
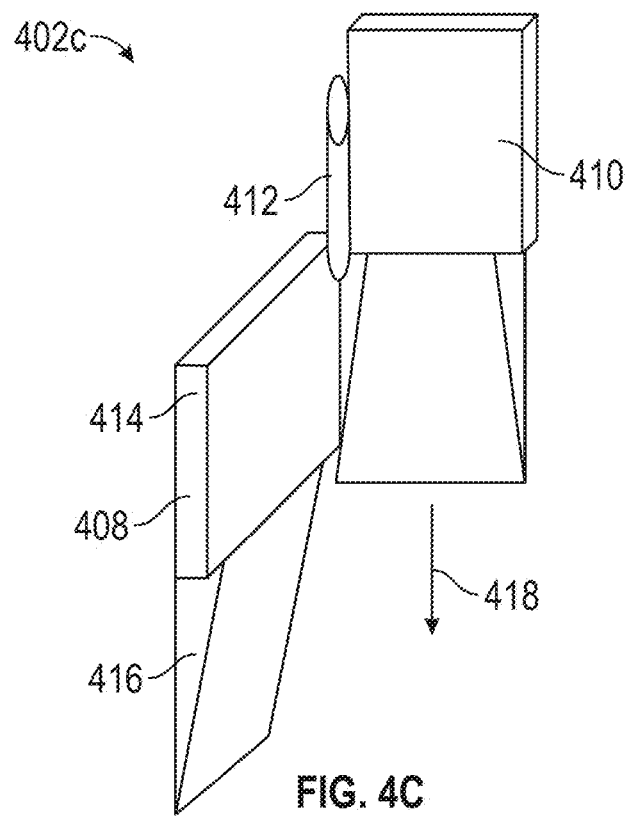
FIGS. 4C and 4D illustrate an adjustable L-shaped shim structure configured in accordance with embodiments of the present technology.
Figure 4D:
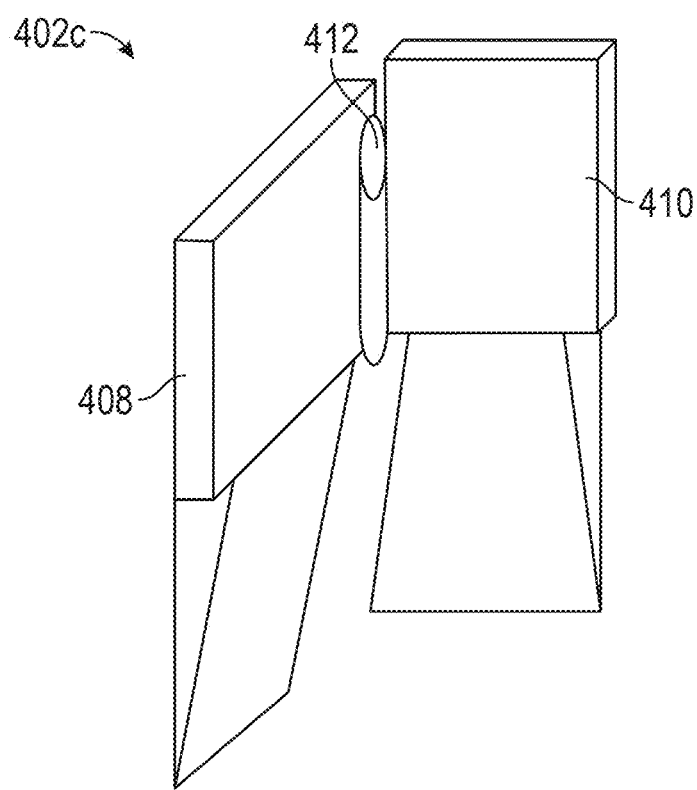

FIGS. 4C and 4D are perspective views of an adjustable L-shaped shim structure 402c configured in accordance with embodiments of the present technology. The shim structure 402c includes a first panel 408 and a second panel 410 connected to each other via an adjustable connection 412. In the illustrated embodiment, the first and second panels 408, 410 each have a rectangular or square flattened section 414 connected to a tapered section 416. In other embodiments, the first and/or second panels 408, 410 can have a different shape, as discussed elsewhere herein. For example, the first panel 408 and second panel 410 can be identical or similar to the first panel 404 and second panel 406 of FIGS. 4A and 4B, respectively.

The adjustable connection 412 can be any attachment mechanism (e.g., joint, hinge, pivot, etc.) that allows the first and second panels 408, 410 to move (e.g., translate and/or rotate) independently relative to each other. For example, as shown in FIGS. 4C and 4D, the adjustable connection 412 can be a slidable connection that allows the first and second panels 408, 410 to slide relative to each other along a lengthwise direction 418. In some embodiments, the adjustable connection 412 is configured similarly to a sliding dovetail connection and includes a rod or bolt on the edge of one panel (e.g., the first panel 408) that slides within a receptacle or groove on the edge of the other panel (e.g., the second panel 410). The adjustable connection 412 can allow the first and second panels 408, 410 to slide relative to each other for a predetermined distance (e.g., a distance within a range from 3 cm to 5 cm). The adjustable connection 412 can include a hard stop to prevent the first and second panels 408, 410 from moving beyond the predetermined distance and/or completely separating from each other.

During use, the adjustable connection 412 allows the first and second panels 408, 410 to be moved independently to provide an improved fit with the first interface 126 (FIG. 4A). For example, the first and second panels 408, 410 can be sequentially inserted into the first gap 202 and second gap 204, respectively, of the first interface 126. In some embodiments, the shim structure 402c is initially placed in a partially separated configuration as shown in FIG. 4C, with the second panel 410 displaced vertically relative to the first panel 408. The first panel 408 can be inserted into the first gap 202 between the imaging arm 108 and the support arm 120. Next, the second panel 410 can be moved downward and into alignment with the first panel 408 as shown in FIG. 4D, until the second panel 410 fits into the second gap 204 between the imaging arm 108 and support arm 120. Alternatively, the order can be reversed, with the second panel 410 being inserted before the first panel 408. The adjustable connection 412 can allow each panel to be advanced independently to the appropriate insertion depth for stabilization, which can be advantageous in situations where different spaces within the first interface 126 have different dimensions.

Figure 5A:
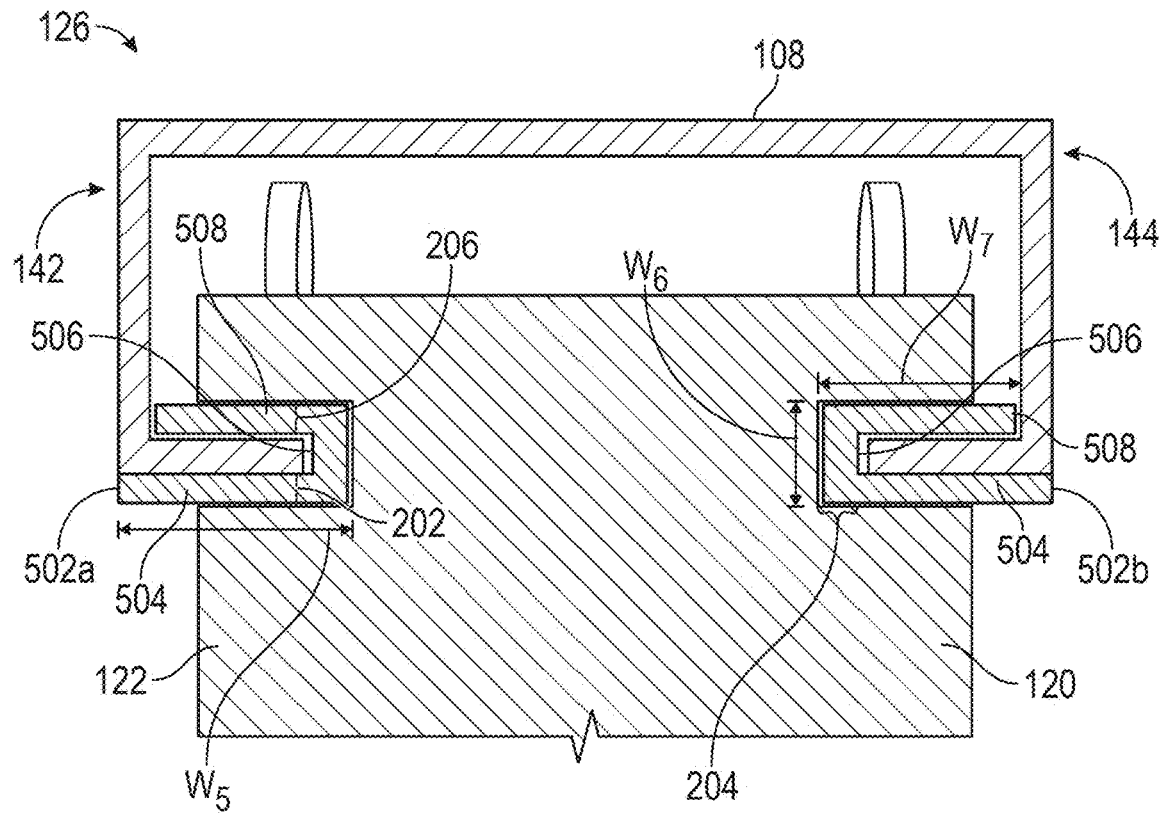
FIGS. 5A and 5B illustrate a set of U-shaped shim structures configured in accordance with embodiments of the present technology.
Figure 5B:
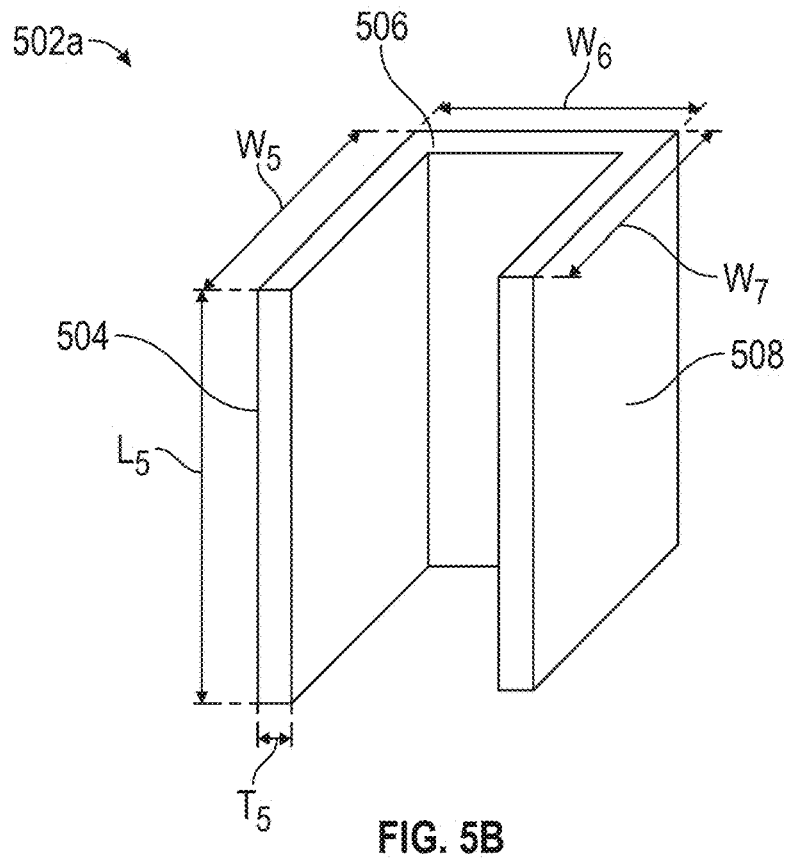

FIG. 5A is a partially schematic cross-sectional view of the first interface 126 with a set of U-shaped shim structures 502a, 502b configured in accordance with embodiments of the present technology, and FIG. 5B is a perspective view of an individual shim structure 502a. Referring to FIGS. 5A and 5B together, the shim structures 502a, 502b can be inserted between the imaging arm 108 and the support arm 120 at the first and second sides 142, 144 of the first interface 126, respectively. The shim structures 502a, 502b can each include a first panel 504, second panel 506, and third panel 508 that are connected to each other to form a U-shaped structure. The shim structures 502a, 502b can each be positioned so that the first panel 504 fills the first gap 202, the second panel 506 fills the second gap 204, and the third panel 508 fills the third gap 206. The first and third panels 504, 508 can engage the upper and lower surfaces of the rails 138 to secure the shim structures 502a, 502b to the imaging arm 108. The panels 504-508 can be integrally formed with each other as a single unitary component, or can be separate components that are coupled to each other via adhesives, bonding, fasteners, etc. In the illustrated embodiment, the panels 504-508 are connected in a fixed geometry and are not movable relative to each other. In other embodiments, however, some or all of the panels 504-508 can be movably coupled to each other, as described further below.

The panels 504-508 can each be flattened, elongate members having a geometry (e.g., size, shape) selected to conform to the shape of the gaps 202-206, respectively. For example, the angle between a pair of connected panels (e.g., the first and second panels 504, 506; the second and third panels 506, 508) can each independently be greater than or equal to 10°, 20°, 30°, 40°, 45°, 50°, 60°, 70°, 80°, 90°, 100°, 110°, 120°, 130°, 140°, 150°, 160°, or 170°. The panels 504-508 can each have any suitable shape, such as rectangular, square, etc. The dimensions of the panels 504-508 can also be varied as desired. In the illustrated embodiment, for example, the panels 504-508 have the same length Ls (e.g., within a range from 1 cm to 20 cm) and thickness $T_5$ (e.g., within a range from 1 mm to 15 mm), but different widths $W_5$, $W_6$, and $W_7$, respectively. For example, the width $W_5$ of the first panel 504 can be greater than or equal to the width $W_7$ of the third panel 508, which can be greater than the width $W_6$ of the second panel 506. For example, the width $W_5$ can be within a range from 0.3 cm to 5 cm, the width $W_6$ can be within a range from 0.1 cm to 3 cm, and the width $W_7$ can be within a range from 0.3 cm to 5 cm. In other embodiments, however, the panels 504-508 can have different dimensions, e.g., the width $W_6$ can be greater than or equal to the width $W_5$ and/or the width $W_7$, some or all of the panels 504-508 can have different lengths, etc. Additionally, although the panels 504-508 are each depicted as having a uniform thickness $T_5$, in other embodiments, some or all of the panels 504-508 can instead have a variable thickness (e.g., a tapered thickness similar to the shim structure 302c of FIG. 3C).

Figure 5C:
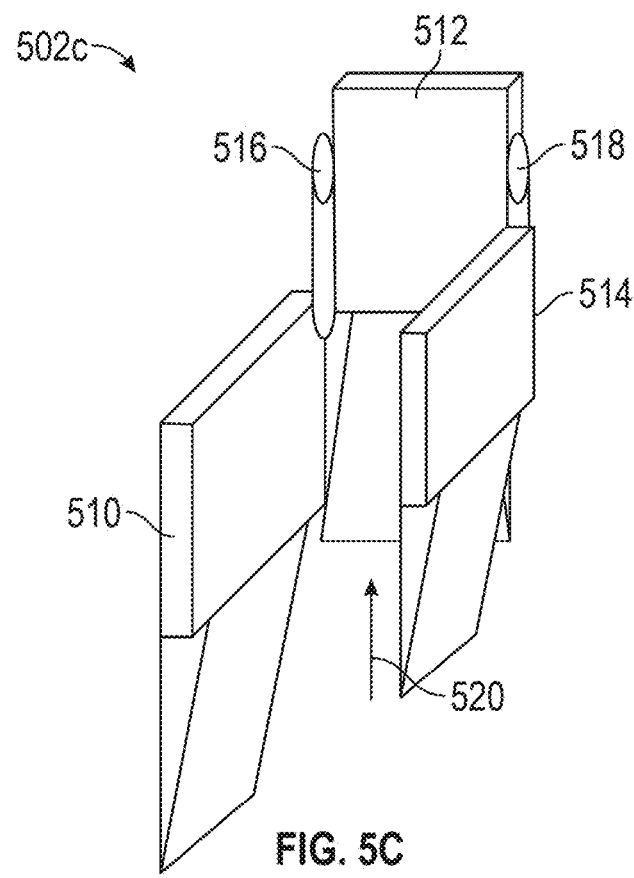
FIGS. 5C and 5D illustrate an adjustable U-shaped shim structure configured in accordance with embodiments of the present technology.
Figure 5D:
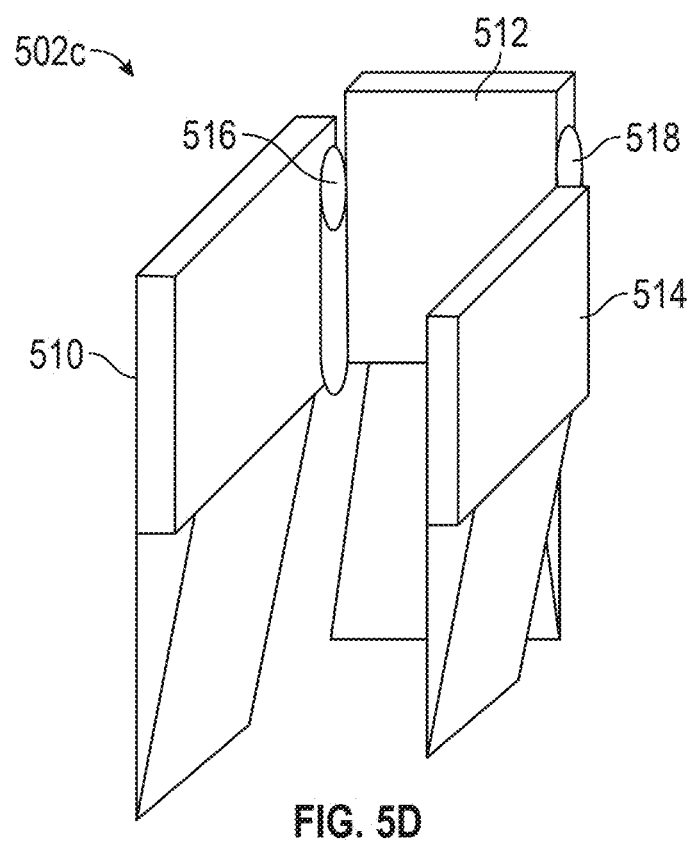

FIGS. 5C and 5D are perspective views of a U-shaped shim structure 502c with slidable connections configured in accordance with embodiments of the present technology. The shim structure 502c includes a first panel 510, second panel 512, and third panel 514 connected to each other via a first adjustable connection 516 and a second adjustable connection 518. The first and second panels 510, 512 can be coupled along their lateral edges by the first adjustable connection 516, and the second and third panels 512, 514 can be coupled their lateral edges by the second adjustable connection 518. In the illustrated embodiment, the panels 510-514 each have a rectangular or square flattened section connected to a tapered section. In other embodiments, some or all of the panels 510-514 can have a different shape, as discussed elsewhere herein. Optionally, the panels 510-514 can be identical or similar to the panels 504-508 of FIGS. 5A and 5B, respectively.

The first and second adjustable connections 516, 518 can each include any suitable attachment mechanism (e.g., joint, hinge, pivot, etc.) that allows the corresponding panels to move (e.g., translate and/or rotate) independently relative to each other. For example, as shown in FIGS. 5C and 5D, the first and second adjustable connections 516, 518 can both be slidable connections (e.g., slidable dovetail connections) that allow the panels 510-514 to translate relative to each other, e.g., along a lengthwise direction 520. The first and second adjustable connections 516, 518 can include any of the features described above with respect to the adjustable connection 412 of FIGS. 4C and 4D.

The first and second adjustable connections 516, 518 can allow the panels 510-512 to be moved independently to provide an improved fit with the first interface 126. For example, the panels 510-514 can be sequentially inserted into the gaps 202-206, respectively, of the first interface 126 (FIG. 5A). In some embodiments, the shim structure 502c is initially placed in a partially separated configuration, such as the configuration shown in FIG. 5C with the first panel 510 and third panel 514 displaced vertically relative to the second panel 512. The panels 510-514 can then be sequentially inserted into the corresponding gaps 202-206 in any suitable order. For example, the second panel 512 can be inserted before the first and third panels 510, 514; and then the first panel 510 can be inserted before the third panel 514, or vice-versa. As another example, the first panel 510 can be inserted first, followed by the second panel 512, and then the third panel 514. When the shim structure 502c is fully inserted, the panels 510-514 can be generally aligned with each other, e.g., as shown in the configuration of FIG. 5D.

Figure 6A:
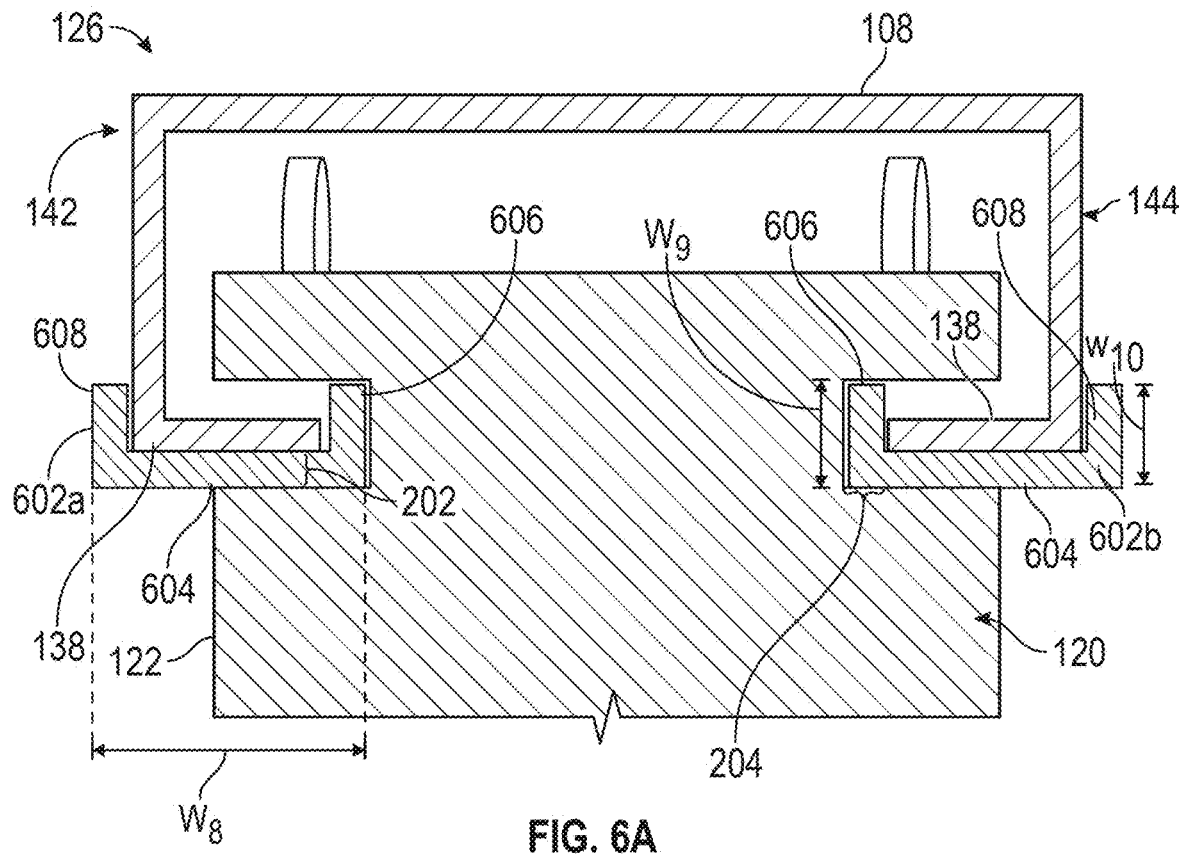
FIGS. 6A and 6B illustrate another set of U-shaped shim structures configured in accordance with embodiments of the present technology.
Figure 6B:
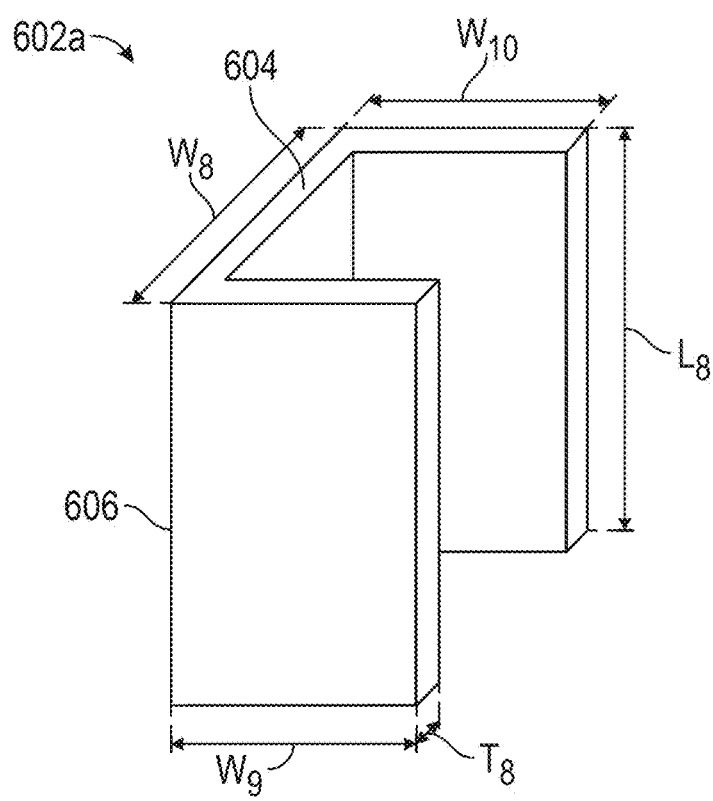

FIG. 6A is a partially schematic cross-sectional view of the first interface 126 with a set of U-shaped shim structures 602a, 602b configured in accordance with embodiments of the present technology, and FIG. 6B is a perspective view of an individual shim structure 602a. Referring to FIGS. 6A and 6B together, the shim structures 602a, 602b can be inserted between the imaging arm 108 and the support arm 120 at the first and second sides 142, 144 of the first interface 126, respectively. The shim structures 602a, 602b can each include a first panel 604, second panel 606, and third panel 608 that are connected to each other to form a U-shaped structure. The shim structures 602a, 602b can each be positioned so that the first panel 604 fills the first gap 202, the second panel 606 fills the second gap 204, and the third panel 608 extends along an outer surface of the imaging arm 108 near the rail 138. In some embodiments, the first and second panels 604, 606 can inhibit movement of the imaging arm 108 relative to the support arm 120, while the third panel 608 can engage the outer surface of the rail 138 to secure the shim structures 602a, 602b in place.

The panels 604-608 can be integrally formed with each other as a single unitary component, or can be separate components that are coupled to each other via adhesives, bonding, fasteners, etc. In some embodiments, the panels 604-608 are connected in a fixed geometry and are not movable relative to each other. In other embodiments, some or all of the panels 604-608 can be movably coupled to each other via adjustable connections, as previously described with reference to FIGS. 5C and 5D.

The panels 604-608 can each be flattened, elongate members having a geometry (e.g., size, shape) selected to conform to the shape of the gaps 202, 204 and the outer surface of the imaging arm 108. For example, the angle between any pair of connected panels (e.g., the first and second panels 604, 606; the first and third panels 604, 608) can each independently be greater than or equal to 10°, 20°, 30°, 40°, 45°, 50°, 60°, 70°, 80°, 90°, 100°, 110°, 120°, 130°, 140°, 150°, 160°, or 170°. The panels 604-608 can each have any suitable shape, such as rectangular, square, etc. The dimensions of the panels 604-608 can also be varied as desired. In the illustrated embodiment, for example, the panels 604-608 have the same length La (e.g., within a range from 1 cm to 20 cm) and thickness $T_5$ (e.g., within a range from 1 mm to 15 mm), but different widths $W_8$, $W_9$, and $W_{10}$, respectively. The width $W_8$ of the first panel 604 can be greater than the width $W_9$ of the second panel 606 and/or the width $W_{10}$ of the third panel 608. The width $W_9$ of the second panel 606 can be equal to or greater than the width $W_{10}$ of the third panel 608. In some embodiments, the width $W_8$ is within a range from 0.3 cm to 5 cm, the width $W_9$ is within a range from 0.1 cm to 3 cm, and the width $W_{10}$ is within a range from 0.1 cm to 3 cm. In other embodiments, however the panels 604-608 can have different dimensions, e.g., the width $W_5$ can be less than or equal to the width $W_9$ and/or the width $W_{10}$, some or all of the panels 604-608 can have different lengths, etc. Additionally, although the panels 604-608 are each depicted as having a uniform thickness $T_8$, in other embodiments, some or all of the panels 604-608 can instead have a variable thickness (e.g., a tapered thickness similar to the shim structure 302c of FIG. 3C).

Figure 7A:
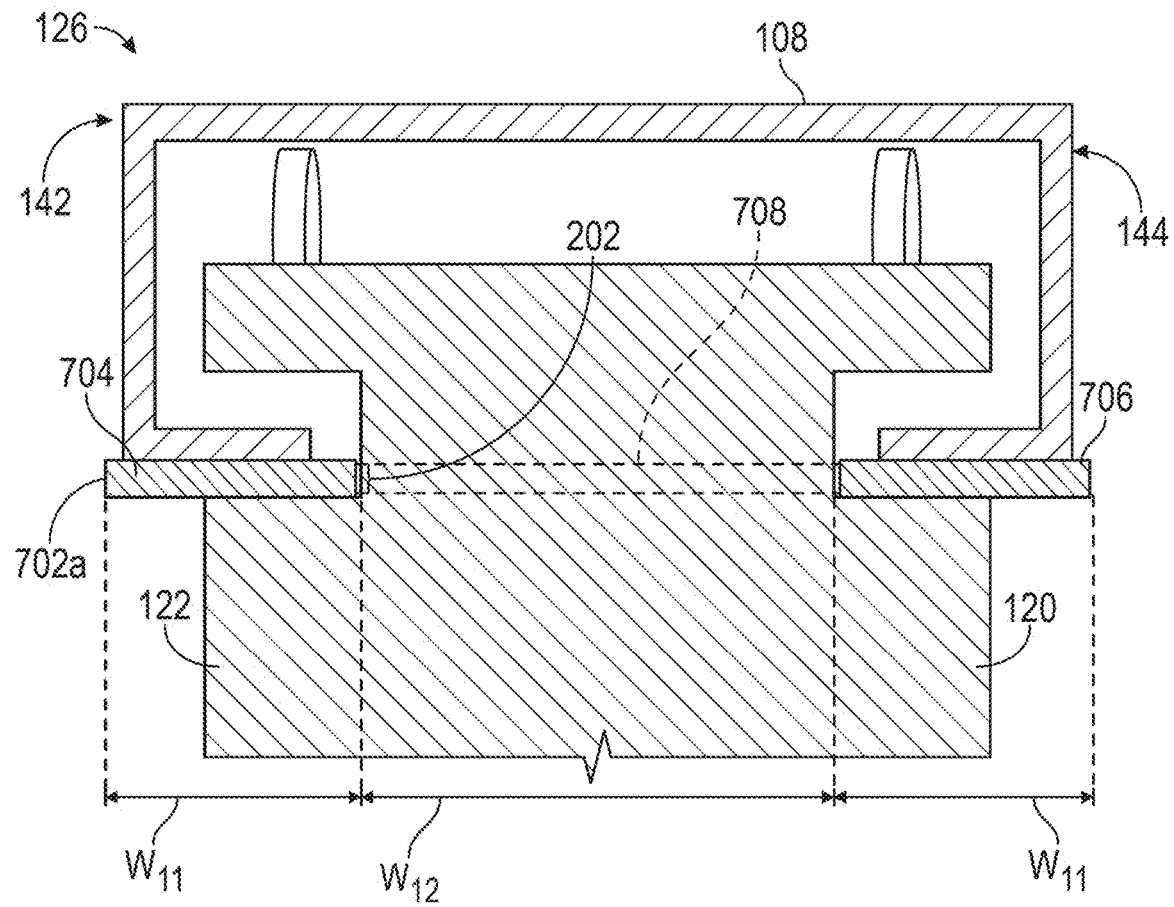
FIGS. 7A and 7B illustrate a shim structure with two arm regions configured in accordance with embodiments of the present technology.
Figure 7B:
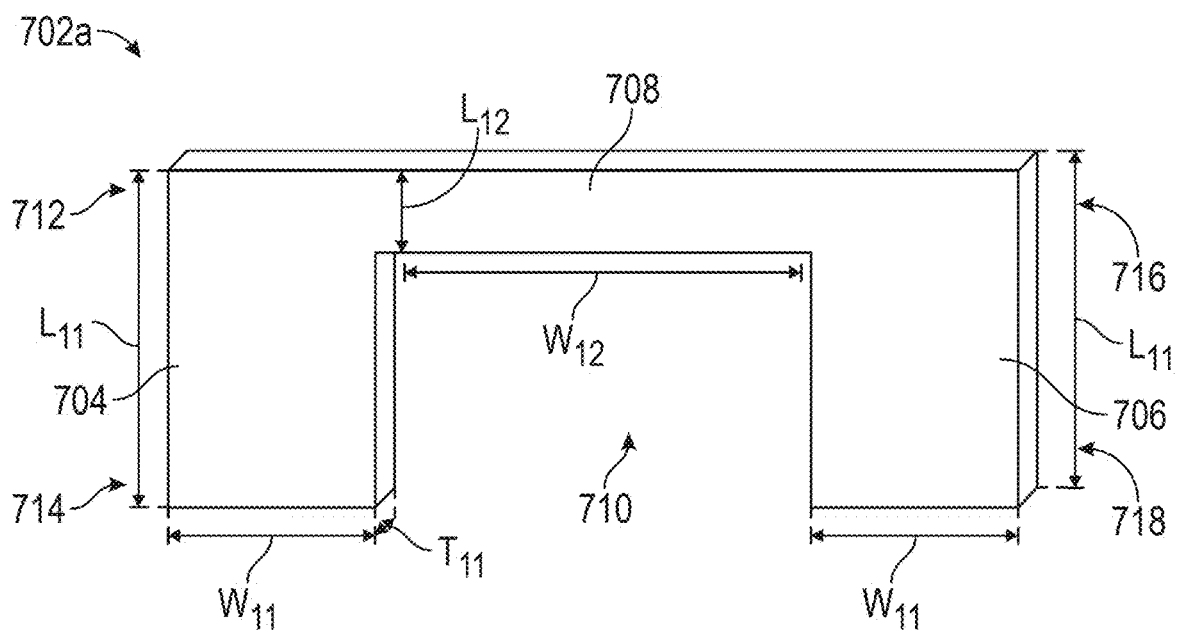

FIG. 7A is a partially schematic cross-sectional view of the first interface 126 with a shim structure 702a and FIG. 7B is a perspective view of the shim structure 702a, in accordance with embodiments of the present technology. Referring to FIGS. 7A and 7B together, the shim structure 702a includes a first arm region 704 and a second arm region 706 connected to each other by a bridge region 708 to form a flattened, horseshoe-shape or U-shaped structure. The first arm region 704 can be a flattened, elongate member (e.g., a panel, block, wedge) including a first end portion 712 coupled to one side of the bridge region 708, and a second end portion 714 spaced apart from the bridge region 708. Similarly, the second arm region 706 can be a flattened, elongate member (e.g., a panel, block, wedge) including a first end portion 716 coupled to the other side of the bridge region 708, and a second end portion 718 spaced apart from the bridge region 708. As best seen in FIG. 7A, the first and second arm regions 704, 706 can fit into the first gaps 202 at the first and second sides 142, 144 of the first interface 126, respectively to stabilize the imaging arm 108 and support arm 120. The first and second arm regions 704, 706 can be generally similar to the shim structures 302a, 302b of FIG. 3A, except that the first and second arm regions 704, 706 are connected to each other by the bridge region 708, rather than being separate, discrete structures.

The bridge region 708 can be a flattened, elongate member (e.g., panel, block, strip, connector, etc.) that extends laterally from the first side 142 of the first interface 126 to the second side 144 of the first interface 126 to join the first and second arm regions 704, 706 to each other. The regions 704-708 can be integrally formed with each other as a single unitary component, or can be separate components that are coupled to each other via adhesives, bonding, fasteners, etc. The regions 704-708 can be connected to each other in a fixed geometry, or can be movably coupled to each other via adjustable (e.g., slidable) connections as discussed elsewhere herein.

In some embodiments, the first and second arm regions 704, 706 inhibit movement of the imaging arm 108 relative to the support arm 120, while the bridge region 708 secures the first and second arm regions 704, 706 in place, e.g., by applying an inward force on the first and second arm regions 704, 706 during rotation of the imaging arm 108. The bridge region 708 can also be beneficial for ensuring that the first and second arm regions 704, 706 are positioned at substantially the same insertion depth into the first gaps 202 at both sides 142, 144 of the first interface 126. Optionally, the shim structure 702a can also include a handle connected to the bridge region 708 (not shown) to facilitate insertion and/or removal of the shim structure 702a from the first interface 126.

The geometry (e.g., size, shape) of the first and second arm regions 704, 706 can be selected to conform to the shape of the first gaps 202. Additionally, the geometry and configuration of the regions 704-708 can define a recess or cavity 710 in the shim structure 702a that accommodates the outer surface of the distal portion 122 of the support arm 120 and/or the imaging arm 108. In the illustrated embodiment, the first and second arm regions 704, 706 and the bridge region 708 each have a rectangular shape. In other embodiments, however, any of the regions 704-708 can have a different shape (e.g., square, triangular, etc.). The dimensions of the regions 704-708 can also be varied as desired. In the illustrated embodiment, for example, the first and second arm regions 704, 706 have the same length Lu (e.g., within a range from 1 cm to 20 cm), width $W_{11}$ (e.g., within a range from 0.3 cm to 5 cm), and thickness $T_{11}$ (e.g., within a range from 1 mm to 15 mm). Alternatively, the first and second arm regions 704, 706 can have different lengths, widths, and/or thicknesses.

The bridge region 708 can have a length $L_{12}$ that is less than the length Lu of the first and second arm regions 704, 706. For example, the length $L_{12}$ can be less than or equal to 10 cm, or within a range from 5 cm to 0.3 cm. The bridge region 708 can have a width $W_{12}$ that is greater than or equal to the width $W_{11}$ of the first and second arm regions 704, 706. For example, the width $W_{12}$ can be within a range from 5 cm to 10 cm, or from 3 cm to 10 cm. In other embodiments, however, the width $W_{12}$ can be less than the width $W_{11}$ of the first and second arm regions 704, 706. The bridge region 708 can have the same thickness $T_{11}$ as the first and second arm regions 704, 706 or can have a different (e.g., larger or smaller) thickness.

Figure 7C:
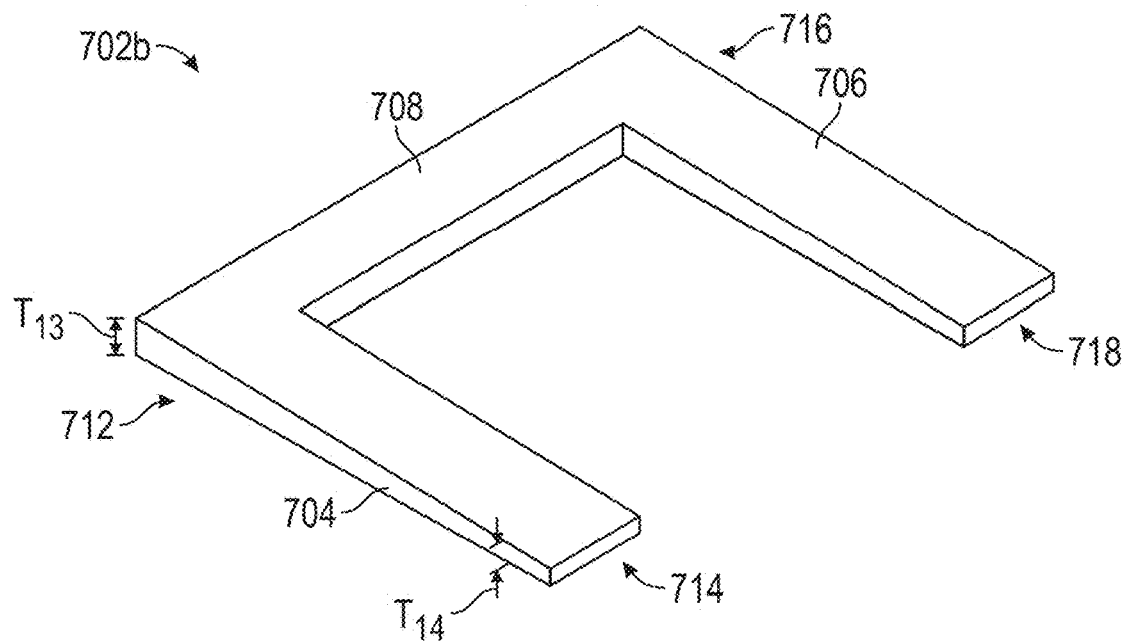
FIGS. 7C and 7D illustrate a shim structure with tapered arm regions configured in accordance with embodiments of the present technology.

FIG. 7C is a perspective view of a shim structure 702b configured in accordance with embodiments of the present technology. The shim structure 702b can be identical or generally similar to the shim structure 702a of FIGS. 7A and 7B, except that the first arm region 704 and second arm region 706 each have a tapered and/or wedge-like shape. As shown in FIG. 7C, the first and second arm regions 704, 706 each have a first thickness $T_{13}$ at their first end portions 712, 716, and a second thickness $T_{14}$ at their second end portions 714, 718. The first thickness $T_{13}$ can be greater than the second thickness $T_{14}$. For example, the first thickness $T_{13}$ can be at least 3 mm, 4 mm, 5 mm, 6 mm, 7 mm, 8 mm, 9 mm, 10 mm, or 15 mm, or within a range from 4 mm to 8 mm. The second thickness $T_{14}$ can be less than 5 mm, 4 mm, 3 mm, 2 mm, 1 mm, 0.5 mm, or 0.1 mm, or within a range from 4 mm to 0.1 mm. Optionally, the first and second arm regions 704, 706 can each be tapered to have a triangular cross-sectional shape (e.g., similar to the shim structure 302c of FIG. 3C), with the angle at the respective second end portion 714, 718 being less than or equal to 80°, 70°, 60°, 50°, 45°, 40°, 35°, 30°, 25°, 20°, 15°, 10°, or 5°.

Figure 7D:
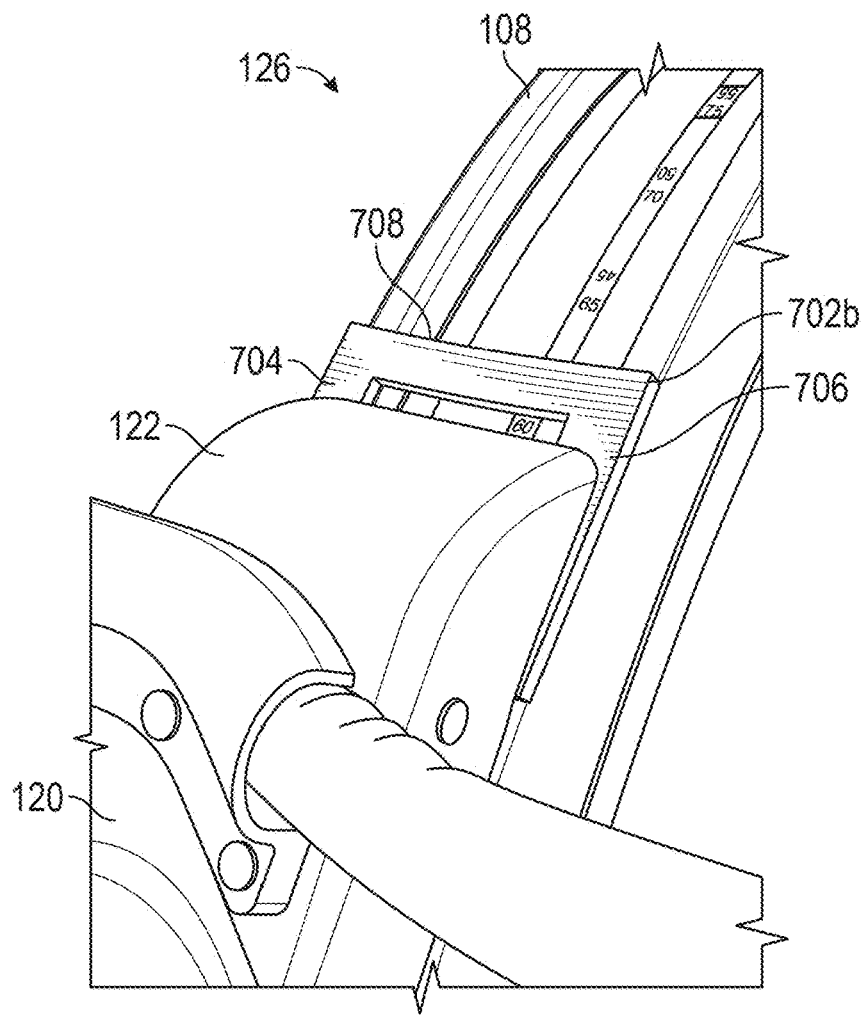

FIG. 7D is a perspective view of the shim structure 702b positioned at the first interface 126 in accordance with embodiments of the present technology. As shown in FIG. 7D, the shim structure 702b is positioned at one end of the first interface 126, with the first and second arm regions 704, 706 inserted into the spaces between the imaging arm 108 and the distal portion 122 of the support arm 120, and the bridge region 708 extending laterally across the imaging arm 108. The presence of the bridge region 708 can help the user visually confirm whether the first and second arm regions 704, 706 are positioned at the substantially the same insertion depth within the first interface 126, which can be beneficial for improving mechanical stability during manual rotation. Optionally, another shim structure identical or similar to the shim structure 702b can be positioned at the other end of the first interface 126 (not shown in FIG. 7D).

FIGS. 7E-7H illustrate additional shim structures 702c-702f configured in accordance with embodiments of the present technology. The shim structures 702c-702f can be generally similar to the shim structures 702a, 702b of FIGS. 7A-7D. Accordingly, the discussion of the shim structures 702c-702f will be limited to those features that differ from the embodiments of FIGS. 7A-7D. Additionally, any of the features of the shim structures 702c-702f can be combined with the embodiment of FIGS. 7A-7D and/or with each other.

FIG. 7E is a perspective view of a shim structure 702c including a set of ridges 720 configured in accordance with embodiments of the present technology. The ridges 720 can be elongated, raised structures located at or near the inner edges of the first and second arm regions 704, 706. In the illustrated embodiment, each ridge 720 extends only partially along the length of the respective first or second arm region 704, 706, and terminates before the location where the arm region connects to the bridge region 708. In other embodiments, however, each ridge 720 can extend along the entire length of the respective first or second arm region 704, 706. When the shim structure 702c is inserted into the first interface 126, the ridges 720 can extend above the surfaces of the first and second arm regions 704, 706 to further secure the shim structure 702c in place.

FIG. 7F is a perspective view of a shim structure 702d including a plurality of protrusions 722 configured in accordance with embodiments of the present technology. As shown in FIG. 7F, the protrusions 722 are located along the inner surfaces of the first and second arm regions 704, 706 and extend inward into the recess 710. When the shim structure 702d is positioned at the first interface 126, the protrusions 722 can engage the distal portion 122 of the support arm 120 to secure the shim structure 702d in place. The shim structure 702d can include any suitable number of protrusions 722, such as one, two, three, four, five, ten, fifteen, twenty, or more protrusions 722. Although the protrusions 722 are depicted as being rounded, semi-circular bumps, in other embodiments the protrusions 722 can have a different shape, such as square, rectangular, triangular, etc. Optionally, the protrusions 722 can be angled toward the bridge region 708 to further lock the shim structure 702d into place. The dimensions and spacing of the protrusions 722 can also be varied as desired. For example, the protrusions 722 can each have a width and/or height within a range from 1 mm to 10 mm, and can be spaced apart from each other by a distance within a range from 1 mm to 10 mm.

FIG. 7G is a perspective view of a shim structure 702e including a plurality of square or rectangular notches 724. As shown in FIG. 7G, the notches 724 are located along the inner surfaces of the first and second arm regions 704, 706. The notches 724 can create a tooth-like texture along the inner surfaces of the first and second arm regions 704, 706 to improve engagement between the shim structure 702e and the support arm 120. The shim structure 702c can include any suitable number of notches 724, such as one, two, three, four, five, ten, fifteen, twenty, or more notches 724. The dimensions and spacing of the notches 724 can be varied as desired, e.g., the notches 724 can each have a width and/or depth within a range from 1 mm to 10 mm, and can be spaced from each other by a distance within a range from 1 mm to 10 mm.

FIG. 7H is a perspective view of a shim structure 702f including a plurality of triangular notches 726. The notches 726 can be oriented so that the base of each triangular notch 726 is connected to the recess 710 and the apex of each triangular notch 726 points away from the recess 710. The spacing, size, and function of the notches 726 can otherwise be generally similar to the square or rectangular notches 724 of FIG. 7G.

In some embodiments, when the shim structures described herein are placed in the first interface 126 between the imaging arm 108 and support arm 120, the shim structure can reduce or prevent the imaging arm 108 from sliding relative to the support arm 120, thus inhibiting orbital rotation of the imaging arm 108. Alternatively, the shim structures described herein can be configured to permit orbital rotation of the imaging arm 108, which may improve convenience and case of use.

Figure 8A:
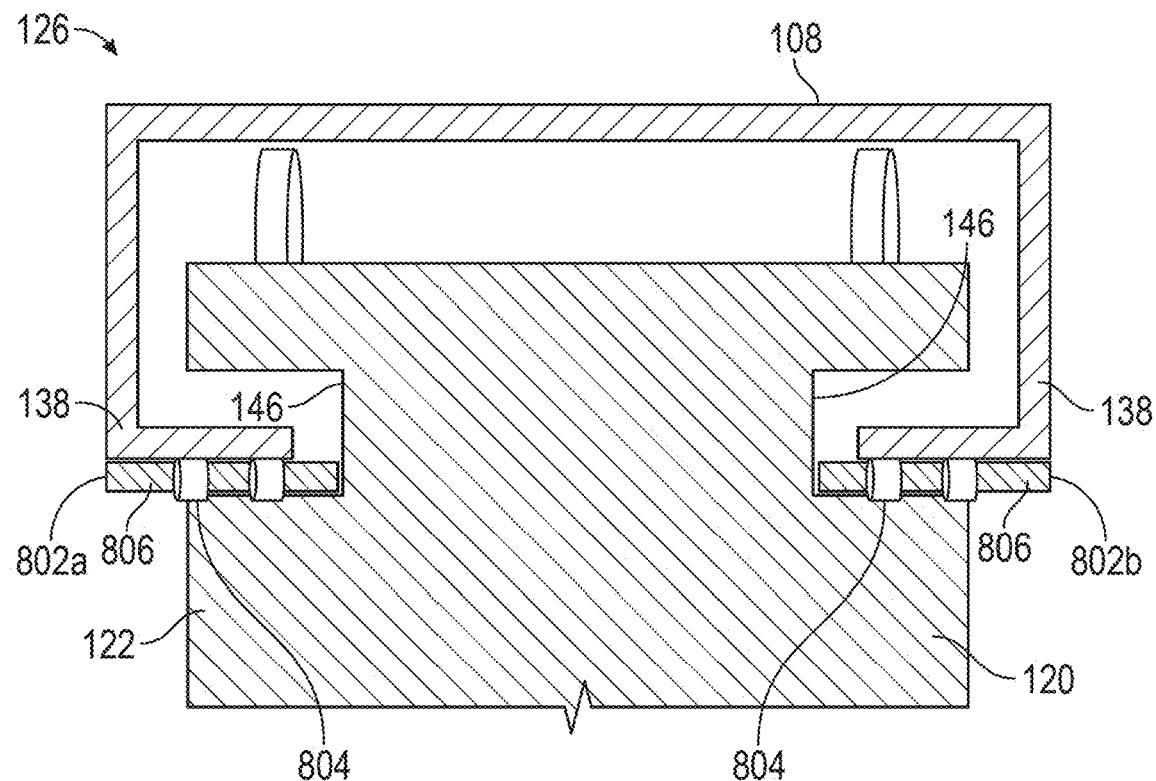
FIGS. 8A and 8B illustrate a set of shim structures with rollers configured in accordance with embodiments of the present technology.
Figure 8B:
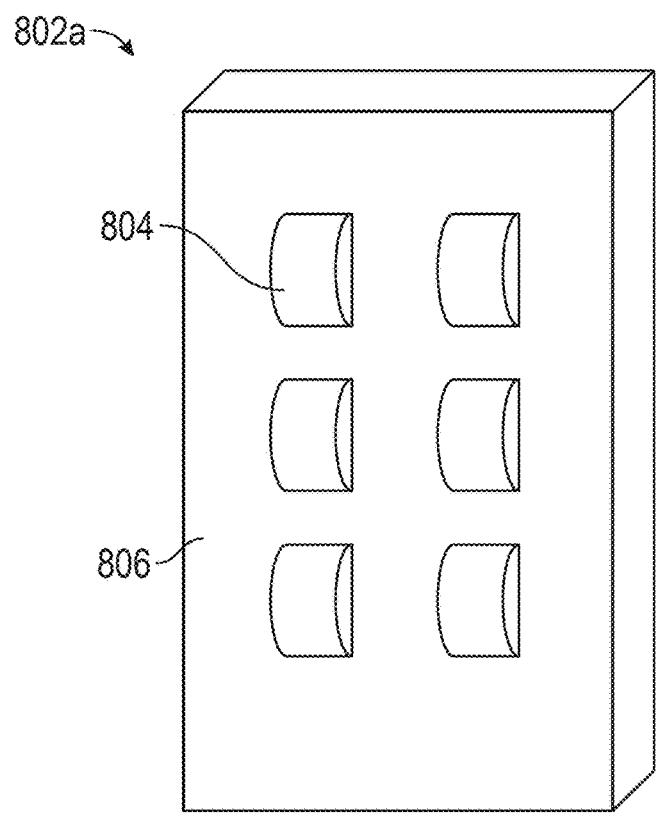

FIG. 8A is a partially schematic cross-sectional view of the first interface with a set of shim structures 802a, 802b with rollers 804, and FIG. 8B is a perspective view of an individual shim structure 802a, in accordance with embodiments of the present technology. The shim structures 802a, 802b can each include a panel 806, e.g., similar to the shim structures 302a, 302b of FIGS. 3A and 3B. One or more rollers 804 (e.g., wheels, ball bearings, etc.) can be embedded in or otherwise coupled to the panel 806. The rollers 804 can protrude out of the upper and/or lower surfaces of the panel 806. Accordingly, when the shim structure 802a, 802b are inserted in the first interface 126, the rollers 804 can contact the surfaces of the imaging arm 108 and/or support arm 120 to allow these components to slide relative to each other. In the illustrated embodiment, for example, the rollers 804 contact the lower surfaces of the rails 138 of the imaging arm 108 and the upper surfaces of the grooves 146 formed in the distal portion 122 of the support arm 120. Thus, the imaging arm 108 can still be rotated in an orbital rotation direction while being stabilized by the shim structures 802a, 802b for propeller rotation.

In some embodiments, the shim structures described herein are configured to be permanently or temporarily attached to the imaging apparatus 104, even when not in use. For example, the shim structure can be coupled to a portion of the imaging apparatus 104 (e.g., to the imaging arm 108) via a mounting mechanism. The mounting mechanism can allow the shim structure to be moved between an engaged configuration, in which the shim structure is stabilizing the imaging apparatus 104 for manual rotation as described elsewhere herein, and a disengaged configuration, in which the shim structure remains attached to the imaging apparatus 104 by the mounting mechanism but is not stabilizing the imaging apparatus 104. In the disengaged configuration, the components of the imaging apparatus 104 (e.g., the imaging arm 108 and support arm 120) can move freely relative to each other without being obstructed by the shim structure. This approach allows the operator to quickly and easily switch between stabilized and non-stabilized operation of the imaging apparatus 104, while reducing the likelihood of the shim structure being lost when not in use.

Figure 9A:
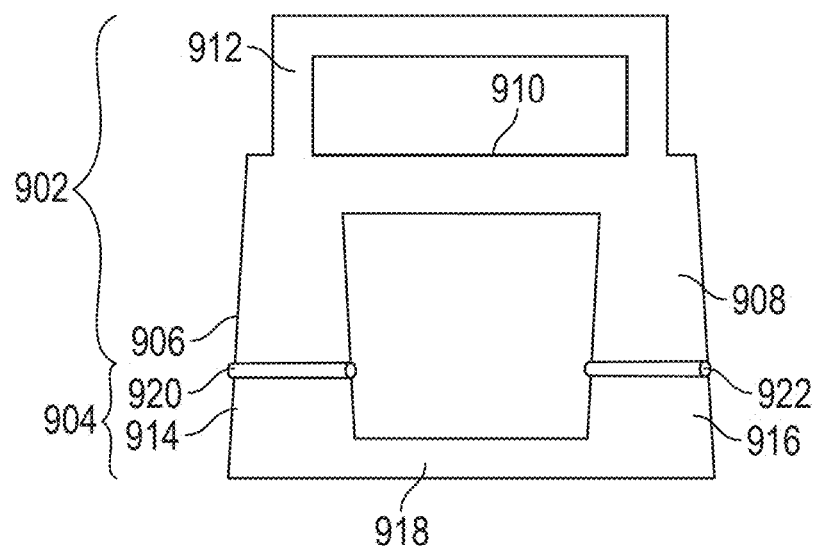
FIGS. 9A-9F illustrate a shim structure with a mounting mechanism configured in accordance with embodiments of the present technology.

FIGS. 9A-9F illustrate a shim structure 902 with a mounting mechanism 904 configured in accordance with embodiments of the present technology. Referring first to FIG. 9A, which is a partially schematic top view of the shim structure 902, the shim structure 902 is a flattened, U-shaped structure that is generally similar to the shim structures 702a and 702b of FIGS. 7A-7D. For example, the shim structure 902 can include a first arm region 906, a second arm region 908, and a bridge region 910 connecting the first and second arm regions 906, 908. The shim structure 902 can optionally include a handle 912 coupled to the bridge region 910 to allow an operator to engage and disengage the shim structure 902 from the first interface 126 of the imaging apparatus 104, as described further below.

In some embodiments, the mounting mechanism 904 is also a flattened, U-shaped structure including a respective first arm region 914, second arm region 916, and bridge region 918. The first arm region 914 of the mounting mechanism 904 can be coupled to the first arm region 906 of the shim structure 902 via a first hinge 920, and the second arm region 916 of the mounting mechanism 904 can be coupled to the second arm region 908 of the shim structure 902 via a second hinge 922. The bridge region 918 can be a bar or similar structure that engages a portion of the imaging apparatus 104 to prevent the shim structure 902 from being removed from the imaging arm 108.

Figure 9B:
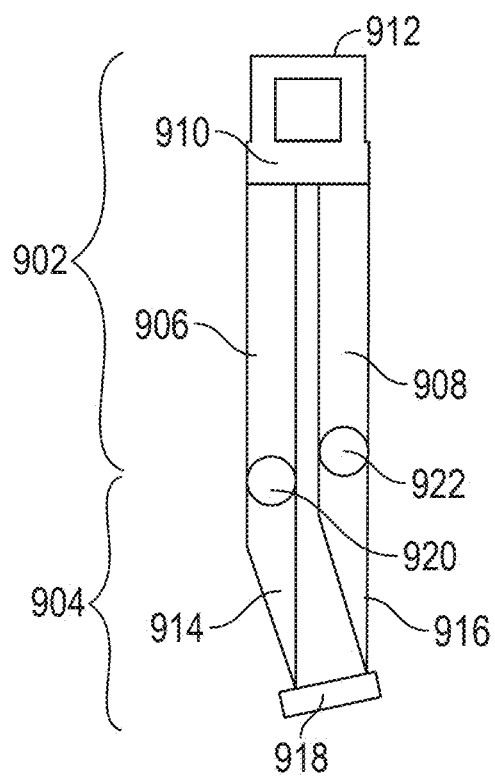
Figure 9C:
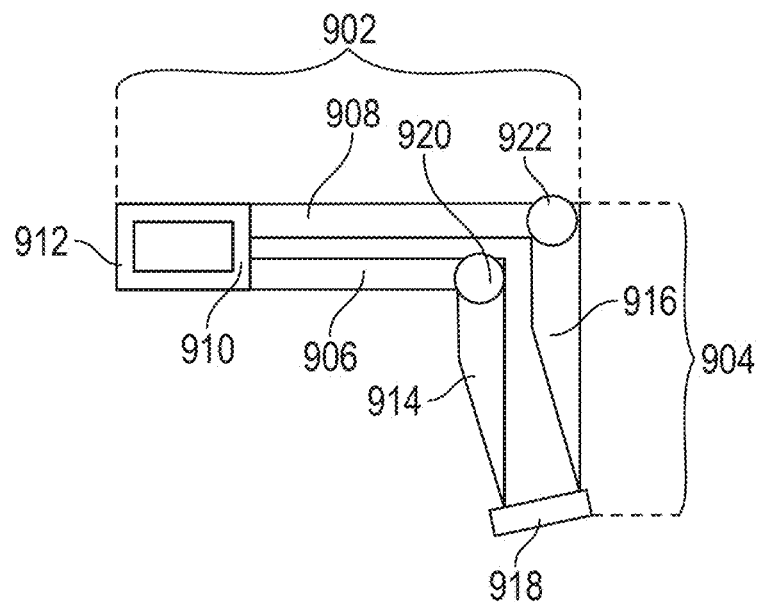

FIGS. 9B and 9C are partially schematic side views of the shim structure 902 and mounting mechanism 904 in a straightened state (FIG. 9B) and a bent state (FIG. 9C). As shown in FIG. 9B, in the straightened state, the longitudinal axis of the shim structure 902 can be generally aligned with (e.g., parallel to) the longitudinal axis of the mounting mechanism 904. As shown in FIG. 9C, in the bent state, the shim structure 902 can pivot relative to the mounting mechanism 904 around the first and second hinges 920, 922, such that the longitudinal axis of the shim structure 902 is offset from (e.g., perpendicular to) the longitudinal axis of the mounting mechanism 904.

Figure 9D:
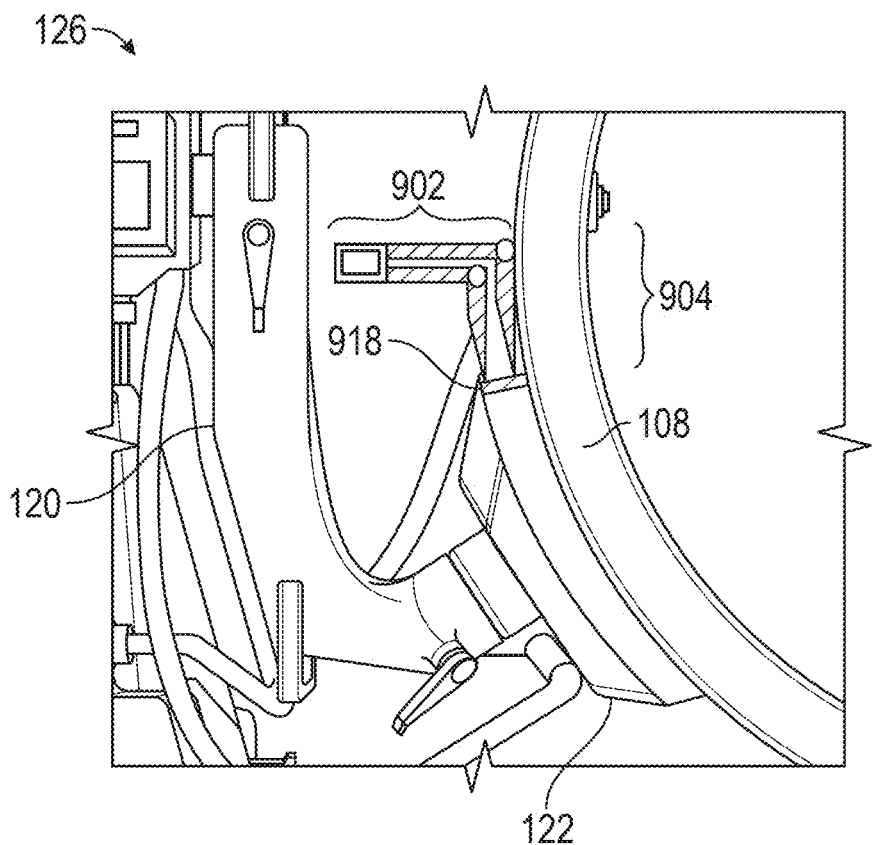
Figure 9E:
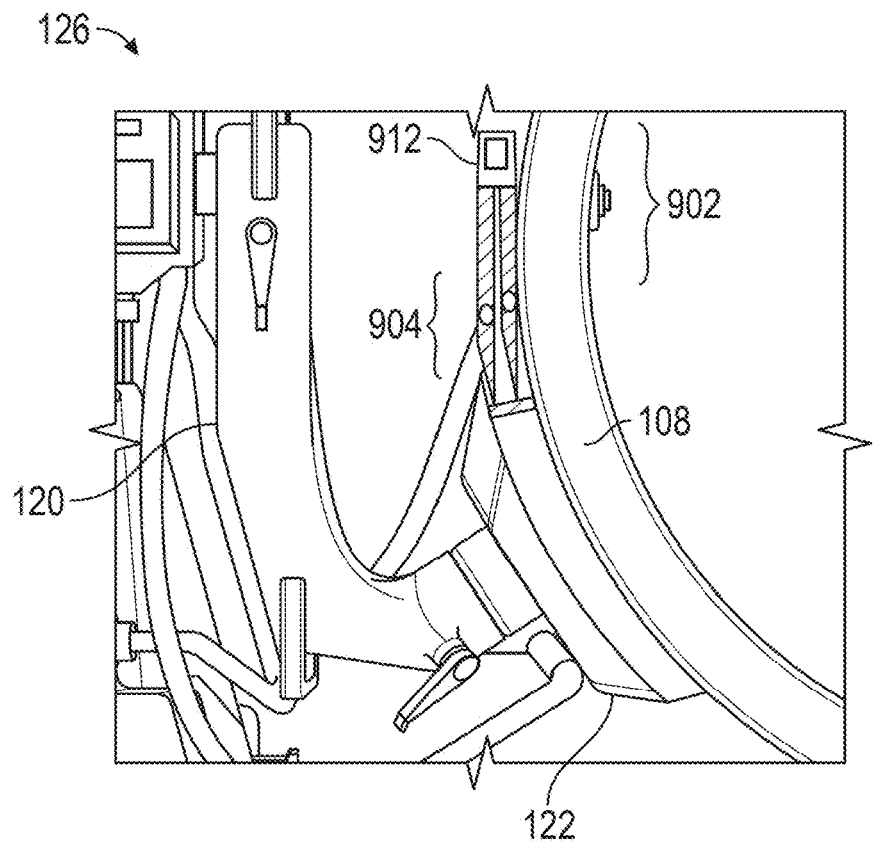
Figure 9F:
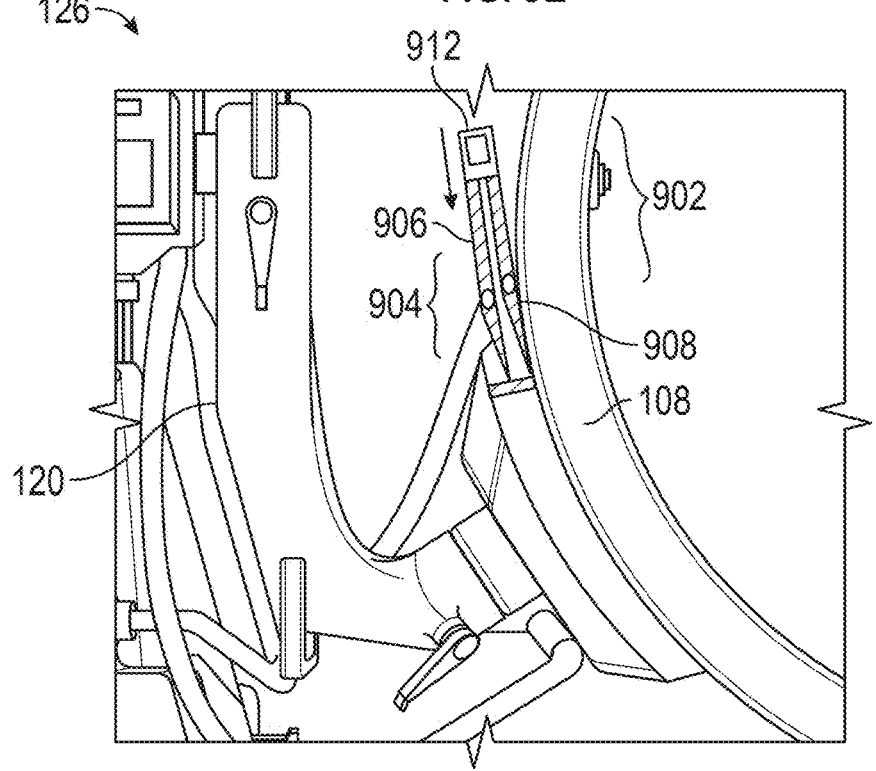

FIGS. 9D-9F are partially schematic side views of the shim structure 902 and mounting mechanism 904 during use, in accordance with embodiments of the present technology. Referring first to FIG. 9D, the mounting mechanism 904 can be positioned at the first interface 126 between the imaging arm 108 and the distal portion 122 of the support arm 120. In some embodiments, the bridge region 918 of the mounting mechanism 904 is inserted into the grooves 146 (FIG. 1C) between the distal portion 122 of the support arm 120 and the rails 138 (FIG. 1C) of the imaging arm 108, in an orientation extending laterally across the track 140 (FIG. 1C) of the imaging arm 108. Accordingly, the distal portion 122 of the support arm 120 located within the track 140 can obstruct the mounting mechanism 904, and thus, the shim structure 902, from being removed from the first interface 126. In such embodiments, the shim structure 902 can be coupled to the mounting mechanism 904 after the mounting mechanism 904 has been inserted into the first interface 126.

When stabilization is not needed, the shim structure 902 can be placed in a disengaged configuration as shown in FIG. 9D. In the disengaged configuration, the shim structure 902 is positioned out of and away from the first interface 126. To prevent the shim structure 902 from inadvertently sliding into the first interface 126 (e.g., due to gravity or if bumped by an operator), the shim structure 902 can be rotated into the bent state. In some embodiments, the bridge region 918 of the mounting mechanism 904 is sufficiently low-profile such that the imaging arm 108 can move relative to the support arm 120 (e.g., along an orbital rotation direction) when the shim structure 902 is in the disengaged configuration.

Referring next to FIG. 9E, when stabilization is desired, the operator can rotate the shim structure 902 into the straightened state using the handle 912. Subsequently, the operator can place the shim structure 902 into an engaged configuration as shown in FIG. 9F by advancing the shim structure 902 into the first interface 126 using the handle 912. In the engaged configuration, the first and second arm regions 906, 908 of the shim structure 902 can be positioned in the gaps between the support arm 120 and imaging arm 108 to inhibit unwanted movements, as described elsewhere herein. Once the imaging procedure is complete, the shim structure 902 can be retracted out of the first interface 126 and folded back into the disengaged configuration of FIG. 9D.

Figure 10A:
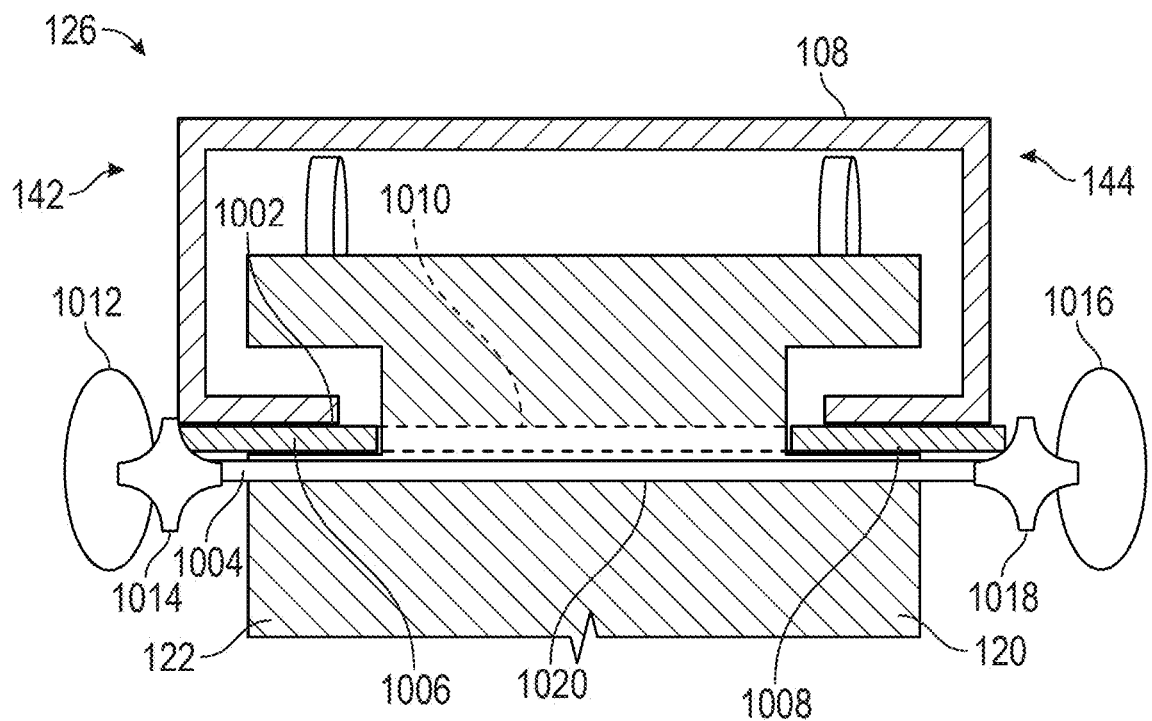
FIGS. 10A-10D illustrate another shim structure with a mounting mechanism configured in accordance with embodiments of the present technology.

FIG. 10A is a partially schematic cross-sectional view of the first interface 126 of imaging apparatus 104 with a shim structure 1002 and mounting mechanism 1004, and FIG.

Figure 10B:
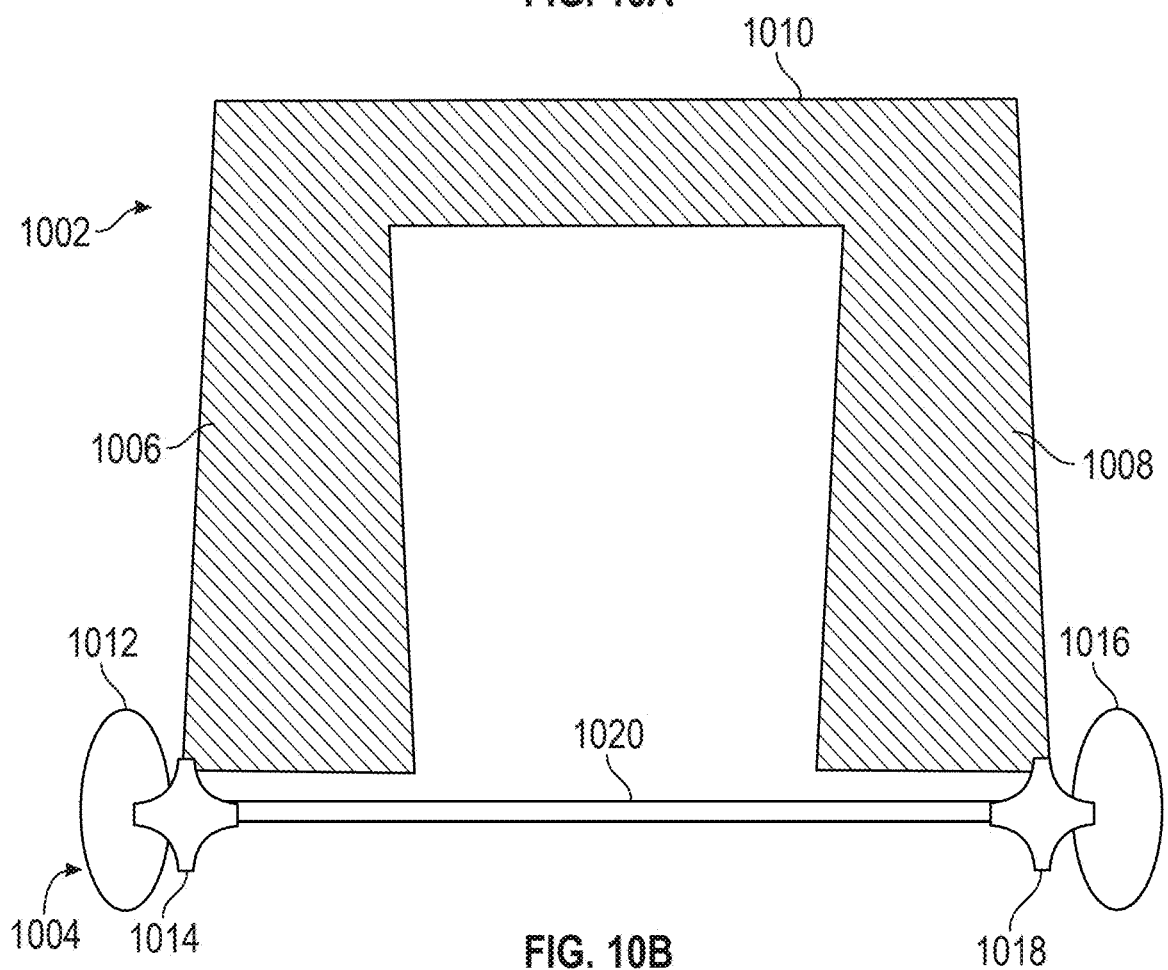

10B is a front view of the shim structure 1002 and mounting mechanism 1004, in accordance with embodiments of the present technology. As best seen in FIG. 10B, the shim structure 1002 is a flattened, U-shaped structure that is generally similar to the shim structures 702a and 702b of FIGS. 7A-7D. For example, the shim structure 1002 can include a first arm region 1006, a second arm region 1008, and a bridge region 1010 connecting the first and second arm regions 1006, 1008.

Referring to FIGS. 10A and 10B together, the mounting mechanism 1004 includes a first knob 1012 attached to a first gear 1014 that is coupled to the first arm region 1006 of the shim structure 1002, and a second knob 1016 attached to a second gear 1018 that is coupled to the second arm region 1008 of the shim structure 1002. The first and second knobs 1012, 1016 can each be rotated by an operator to turn the first and second gears 1014, 1018, which in turn translate the shim structure 1002 between a disengaged configuration and an engaged configuration, as described further below. Optionally, the first and second gears 1014, 1018 can be coupled to each other via a connector 1020 (e.g., a crossbar), such that the first and second arm regions 1006, 1008 are concurrently translated even when only one of the knobs 1012, 1016 is rotated. This configuration can be advantageous for ensuring that the first and second arm regions 1006, 1008 are advanced into the gaps at the first and second sides 142, 144, respectively, of the first interface 126 (FIG. 10A) by the same or similar distances.

Figure 10C:
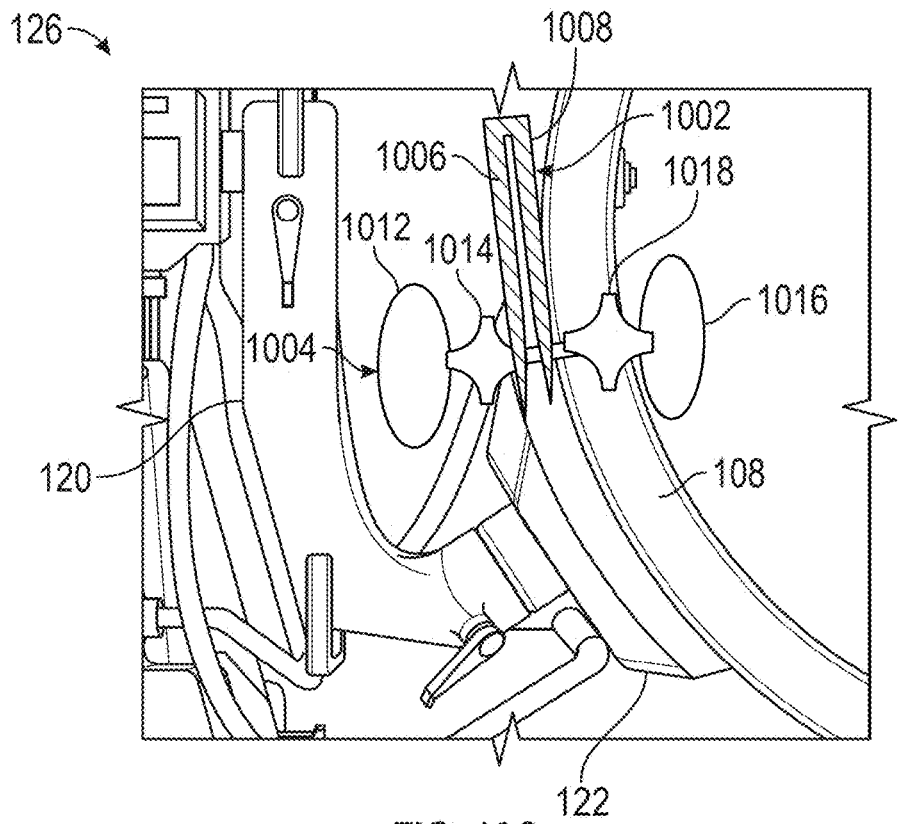
Figure 10D:
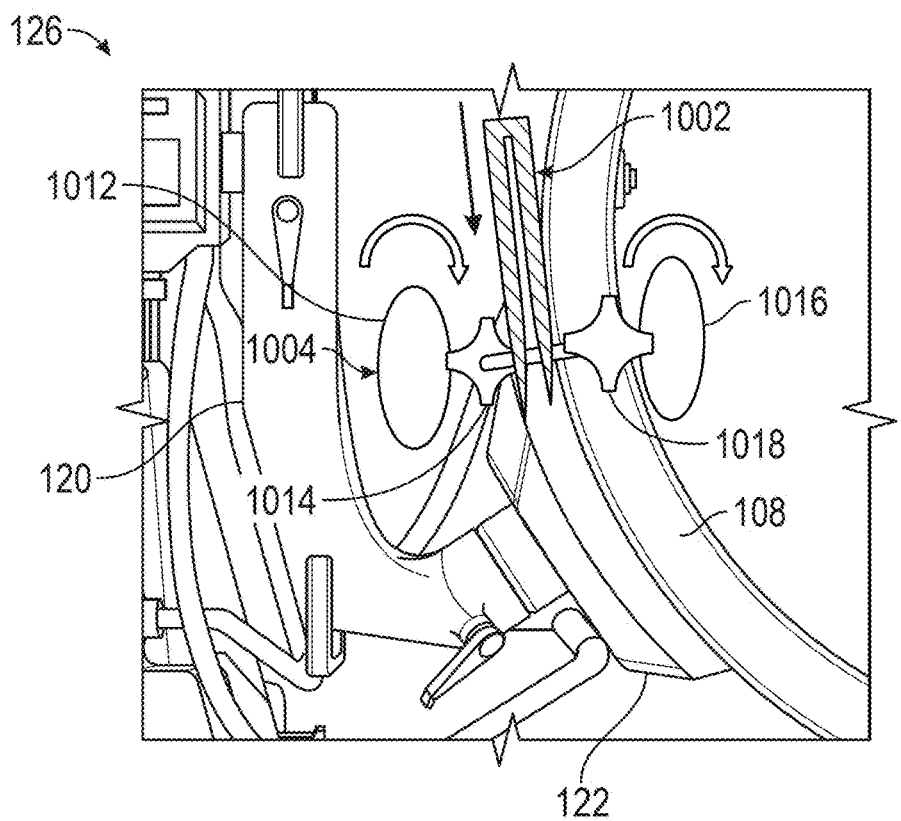

FIGS. 10C and 10D are partially schematic side views of the shim structure 1002 and mounting mechanism 1004 during use, in accordance with embodiments of the present technology. Referring first to FIG. 10C, the mounting mechanism 904 can be positioned at the first interface 126 between the imaging arm 108 and the distal portion 122 of the support arm 120. In some embodiments, the connector 1020 of the mounting mechanism 1004 is inserted into the grooves 146 (FIG. 1C) between the distal portion 122 of the support arm 120 and the rails 138 (FIG. 1C) of the imaging arm 108, in an orientation extending laterally across the track 140 (FIG. 1C) of the imaging arm 108. Alternatively, the connector 1020 can be positioned outside and laterally across the distal portion 122 of the support arm 120.

When stabilization is not needed, the shim structure 1002 can be placed in a disengaged configuration as shown in FIG. 10C. In the disengaged configuration, the shim structure 1002 is positioned out of and away from the first interface 126. When stabilization is desired, the operator can rotate the first and/or second knobs 1012, 1016 of the mounting mechanism 1004 to place the shim structure 1002 into an engaged configuration as shown in FIG. 10D. The rotation of the first and/or second knobs 1012, 1016 can turn the first and/or second gears 1014, 1018 to advance the shim structure 1002 forward relative to the mounting mechanism 1004 and into the first interface 126. In the engaged configuration, the first and second arm regions 1006, 1008 of the shim structure 1002 can be positioned in the gaps between the support arm 120 and imaging arm 108 to inhibit unwanted movements, as described elsewhere herein. Once the imaging procedure is complete, the first and/or second knobs 1012, 1016 can be rotated in the reverse direction to turn the first and/or second gears 1014, 1018 backward to retract the shim structure 1002 relative to the mounting mechanism 1004 and out of the first interface 126.

Figure 11:
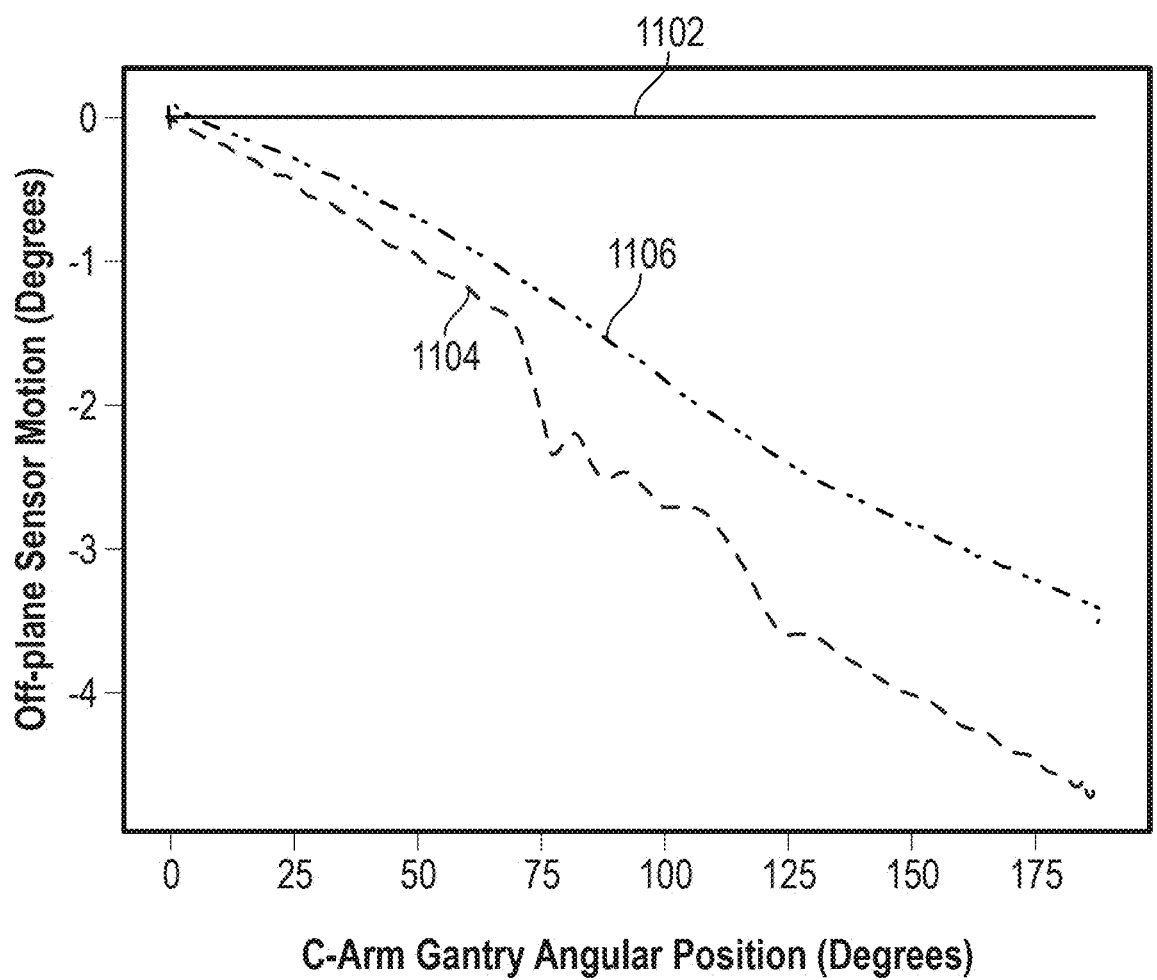
FIG. 11 is a graph illustrating motion of a motion sensor on a C-arm detector with and without shim stabilization.

FIG. 11 is a graph illustrating motion of an IMU on a C-arm detector with and without shim stabilization. The motion data was generated by an IMU with an accelerometer while the C-arm was manually rotated through a continuous 180° propeller rotation. The x-axis represents the rotational position of the C-arm as measured by the IMU. The y-axis represents the degree of off-plane motion of the IMU during the rotation (e.g., unwanted motion). In the illustrated embodiment, there is ideally little or no off-plane motion (e.g., line 1102), indicating that the detector is moving within a single rotational plane. In the absence of shim structures (line 1104), the IMU motion data includes significant oscillations and sharp changes in slope, corresponding to sudden weight shifts and reverberations that occur due to mechanical laxity and weight imbalances between the C-arm detector and source. These movements can be variable and inconsistent between rotations, which can make it difficult or impossible to compensate for such movements using the calibration processes described further below. However, when shim structures are used (line 1106), the IMU motion data exhibits a smooth trajectory with a generally constant slope (in FIG. 11, the C-arm was stabilized with two shim structures similar to the shim structure 702b of FIGS. 7C and 7D). The shim structures can also allow the C-arm to move in a generally consistent trajectory over multiple rotations, which can make it feasible to compensate for the off-plane motion using the calibration processes described further below. As shown in FIG. 11, the shim structures can help with reducing off-plane motion, but may not eliminate it completely. Any residual off-plane motion can be compensated for via a geometric calibration process, as described in greater detail below.

Figure 12:
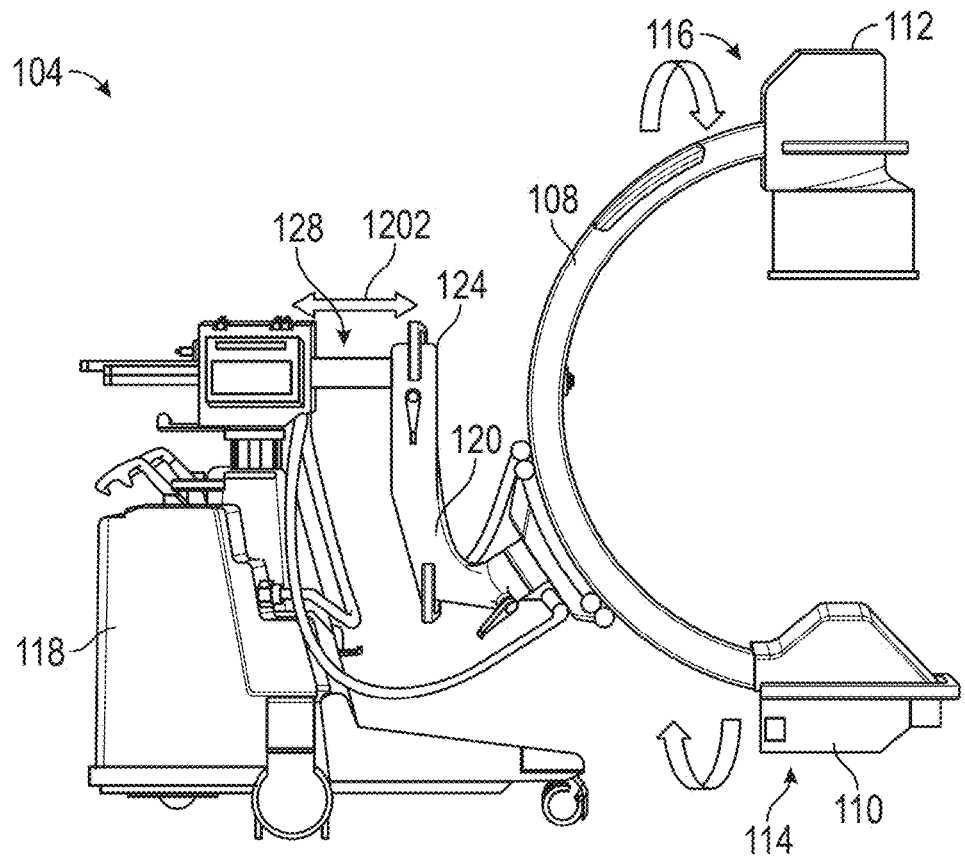
FIG. 12 illustrates an example of unwanted movements that may occur with a manually-operated imaging apparatus.

FIG. 12 illustrates an example of unwanted movements that may occur at the second interface 128 during a manual rotation of the imaging arm 108. In some instances, the location(s) at which force is applied may affect the stability of the imaging arm 108 during manual rotation. Specifically, certain locations may be more likely to produce unwanted and/or non-uniform movements when pushed and/or pulled during manual rotation. For example, when performing a manual propeller rotation, it may be mechanically advantageous to apply force to the first and second end portions 114, 116 of the imaging arm 108, since these locations are located farther from the center of rotation (also known as the "pivot point"), and thus require less force to initiate and/or maintain rotation. However, in situations where the second interface 128 is mechanically unstable (e.g., due to spaces, gaps, or other mechanical laxity between the base 118 and support arm 120), applying force to the first and second end portions 114, 116 of the imaging arm 108 may produce greater torque on the second interface 128, which can cause the support arm 120 and imaging arm 108 to shift relative to the base 118 (e.g., along a translational direction 1202) or otherwise exhibit unwanted and/or non-uniform motions.

In some embodiments, the amount of torque on the second interface 128 can be reduced by applying the rotational force to the proximal portion 124 of the support arm 120 at or near the second interface 128, rather than to the imaging arm 108. However, because this location is closer to the pivot point, the amount of force to perform a manual propeller rotation may be significantly increased. Additionally, the proximal portion 124 of the support arm 120 may lack handles or grips to facilitate manual rotation, or the handle at that location may be too small to offer sufficient leverage. Accordingly, to reduce the amount of force for performing a manual propeller rotation at or near the second interface 128, the present technology can provide a temporary or permanent lever structure that attaches to the proximal portion 124 of the support arm 120 near the second interface 128 to provide greater mechanical advantage for rotation.

FIGS. 13A-14E illustrate representative examples of lever structures that can be used to facilitate manual rotation of an imaging apparatus, in accordance with embodiments of the present technology. Although the lever structures of FIGS. 13A-14E are described and illustrated with reference to components of the imaging apparatus 104 of FIG. 1A, it will be appreciated that the lever structures can also be used with other imaging apparatuses and systems. Additionally, any of the features of the lever structures of FIGS. 13A-14E can be combined with each other.

Figure 13A:
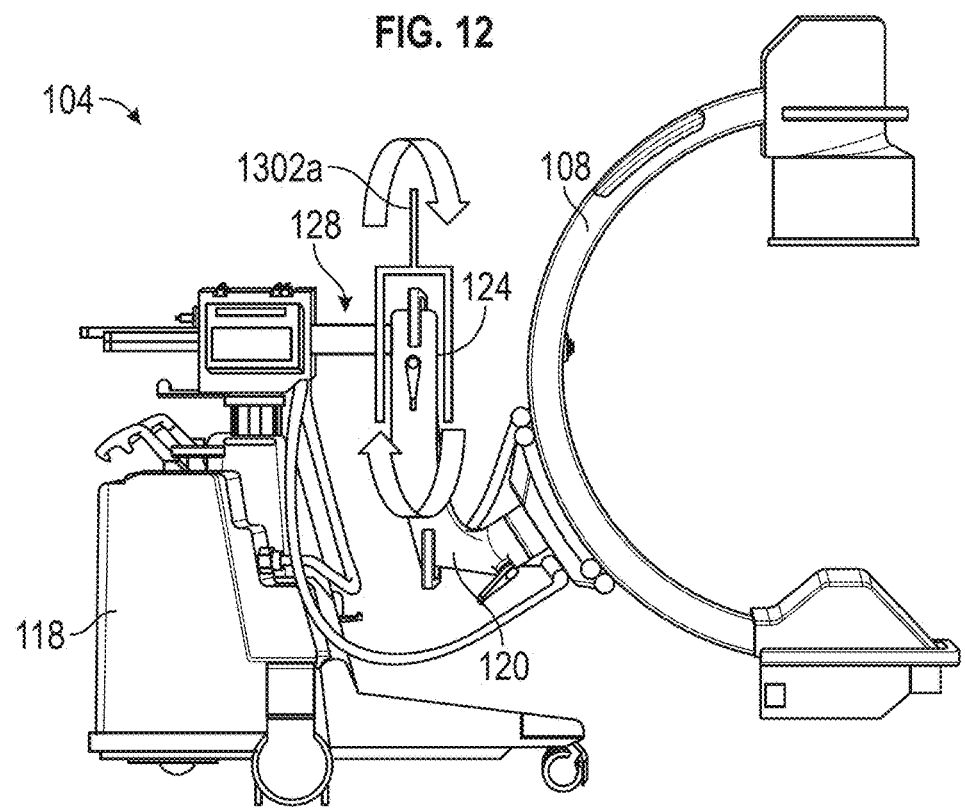

FIG. 13A is a partially schematic view of the imaging apparatus 104 with a lever structure 1302a and FIG. 13B is a closeup, cross-sectional view of the support arm 120 with the lever structure 1302a, in accordance with embodiments of the present technology. The lever structure 1302a is configured to temporarily or permanently attach to the support arm 120 to assist a user in applying a rotational force to the proximal portion 124 of the support arm 120 during a propeller rotation. As best seen in FIG. 13B, the lever structure 1302a includes a handle 1304 coupled to a clamp 1306. The clamp 1306 can include a pair of clamp members 1308 connected to a crossbar 1310 in a fixed geometry. The lever structure 1302a can have a fork-like configuration in which one end of the handle 1304 is coupled to the central portion of the crossbar 1310, and the clamp members 1308 are coupled to the end portions of the crossbar 1310 and extend longitudinally away from the crossbar 1310.

The handle 1304 can be an elongate rod or shaft configured to be held by one or both of the user's hands. The handle 1304 can be sufficiently long to provide leverage for rotating the support arm 120 and imaging arm 108. In some embodiments, for example, the handle 1304 has a length within a range from 10 cm to 70 cm. Optionally, the handle 1304 can include texturing, coatings, an ergonomic shape, and/or other suitable features to improve grip.

The clamp members 1308 can be elongate prongs, arms, etc., configured to secure the lever structure 1302a to the proximal portion 124 of the support arm 120 at or near the second interface 128. The clamp members 1308 can be configured to fit tightly around the support arm 120 so that the lever structure 1302a does not become dislodged when the user applies force to the handle 1304. For example, the spacing between the clamp members 1308 can be within a range from 5 cm to 20 cm. The spacing can be identical or similar to the cross-sectional dimension of the proximal portion 124 of the support arm 120 to provide a tight fit around the support arm 120. In the illustrated embodiment, the clamp members 1308 are affixed to the crossbar 1310 at an angle, such that the spacing between the clamp members 1308 increases with distance from the crossbar 1310. This configuration can allow the clamp members 1308 to fit snugly around the support arm 120 near the pivot point during rotation. Alternatively, the clamp members 1308 can be substantially parallel to each other, such that the spacing between the clamp members 1308 is constant. Each clamp member 1308 can have a length within a range from 10 cm to 30 cm, and a thickness and/or diameter within a range from 1 cm to 5 cm. The clamp members 1308 can have any suitable cross-sectional shape (e.g., square, rectangular, circular).

FIG. 13C is a cross-sectional view of the support arm 120 with an adjustable lever structure 1302b configured in accordance with embodiments of the present technology. The lever structure 1302b can be generally similar to the lever structure 1302a of FIGS. 13A and 13B, except that the lever structure 1302b includes an adjustable clamp member 1314 that can be moved along the crossbar 1310, and a fixed clamp member 1316 that remains stationary. The adjustable clamp member 1314 can be moved relative to the fixed clamp member 1316 to alter the clamp spacing, which can allow the clamp 1312 to accommodate different support arm geometries. In the illustrated embodiment, for example, the adjustable clamp member 1314 is coupled to a trigger 1318 for repositioning the adjustable clamp member 1314. When the trigger 1318 is squeezed, the adjustable clamp member 1314 can slide along the crossbar 1310 toward and/or away from the fixed clamp member 1316. When the trigger 1318 is released, the adjustable clamp member 1314 can be locked in place at its current position along the crossbar 1310. Optionally, the clamp 1312 can include teeth, detents, and/or other ratchet-like features so the adjustable clamp member 1314 is movable to a plurality of different predetermined locations along the crossbar 1310.

FIG. 13D is a cross-sectional view of the support arm 120 with another adjustable lever structure 1302c configured in accordance with embodiments of the present technology. The lever structure 1302c includes a handle 1304 coupled to a clamp 1320 (e.g., a C-clamp, G-clamp, U-clamp). The clamp 1320 can include a frame 1322 (e.g., a curved, square, or rectangular bracket) having an adjustable pad 1324 at one end, and a fixed pad 1326 at the other end. The handle 1304 can be connected to the central portion of the frame 1322 between the two ends. The adjustable pad 1324 can be coupled to a screw 1328 that is rotatable to alter the position of the adjustable pad 1324. Accordingly, the user can turn the screw 1328 to change the spacing between the adjustable pad 1324 and fixed pad 1326 to accommodate different support arm geometries.

Figure 14A:
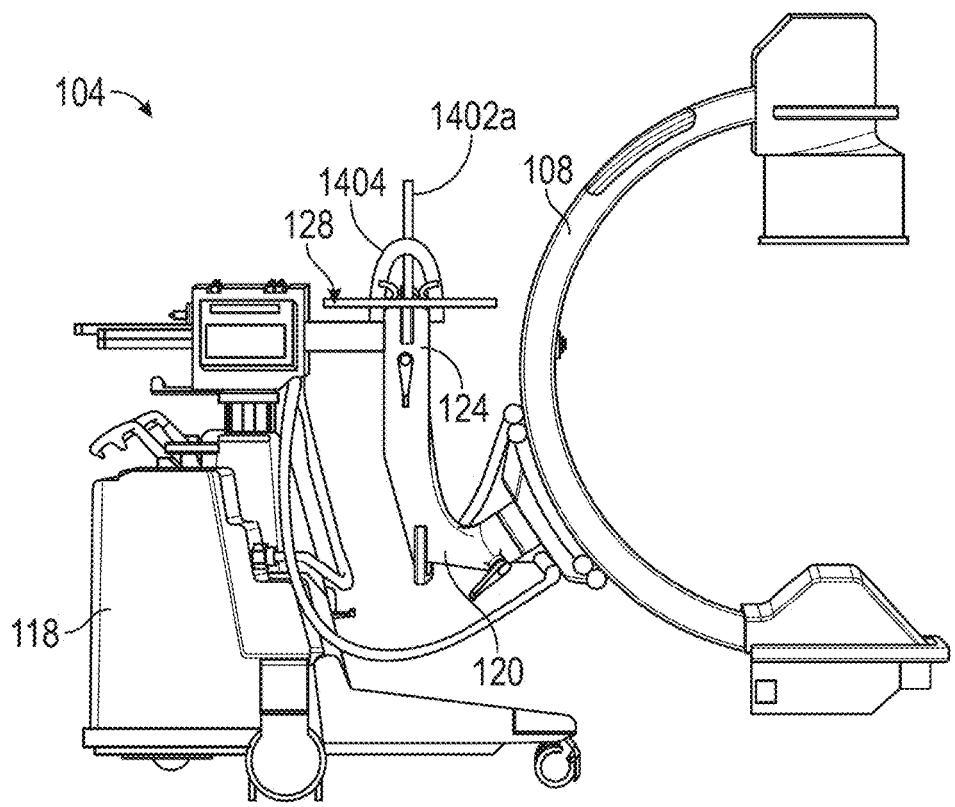
FIGS. 14A and 14B illustrate a lever structure in accordance with embodiments of the present technology.
Figure 14B:
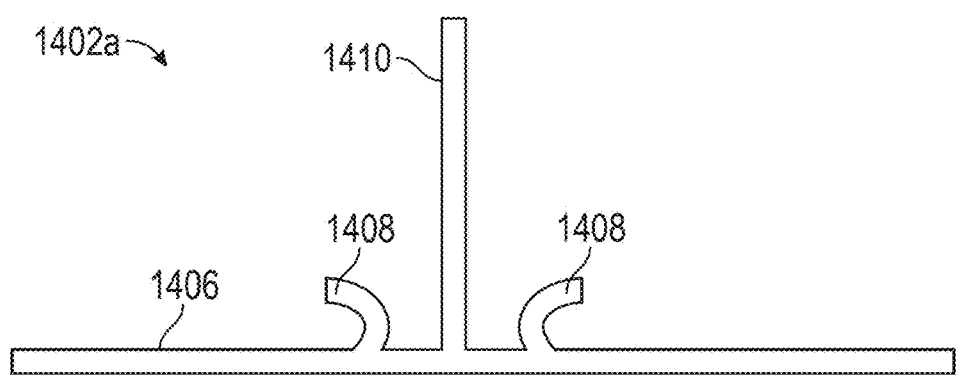

FIG. 14A is a partially schematic view of the imaging apparatus 104 with a lever structure 1402a and FIG. 14B is a front view of the lever structure 1402a, in accordance with embodiments of the present technology. Referring first to FIG. 14A, in some embodiments, the imaging apparatus 104 already includes a handle 1404 at or near the proximal portion 124 of the support arm 120 near the second interface 128. However, the handle 1404 may be too small to provide sufficient mechanical advantage for manually rotating the support arm 120 and imaging arm 108. Accordingly, the lever structure 1402a can be temporarily or permanently coupled to the handle 1404 to provide a longer lever arm and/or otherwise increase the mechanical advantage.

Referring next to FIG. 14B, the lever structure 1402a can include a first elongate member 1406 (e.g., a rod, shaft, or tube) having a pair of hooks 1408. The hooks 1408 can engage the handle 1404 (FIG. 14A) to secure the lever structure 1402a to the support arm 120. The lever structure 1402a can also include a second elongate member 1410 (e.g., a rod, shaft, or tube) connected to the first elongate member 1406 between the hooks 1408. The second elongate member 1410 can be attached to the first elongate member 1406 at a 90° angle or any other suitable angle. During use, the user can grip the first elongate member 1406 and/or second elongate member 1410 to apply a rotational force to the support arm 120 for propeller rotation. In other embodiments, the second elongate member 1410 can be omitted, such that the user applies force using the first elongate member 1406 only.

Figure 14C:
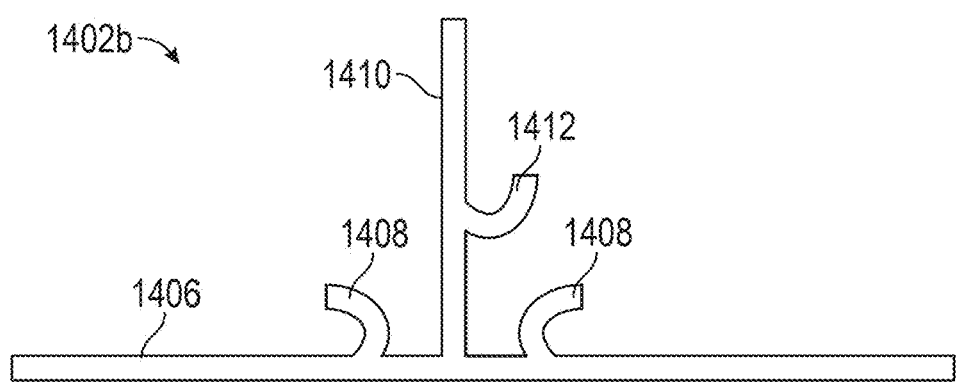
FIG. 14C illustrates another lever structure configured in accordance with embodiments of the present technology.

FIG. 14C is a front view of a lever structure 1402b configured in accordance with embodiments of the present technology. The lever structure 1402b is identical to the lever structure 1402a of FIGS. 12A and 12B, except that the lever structure 1402b includes a third hook 1412 on the second elongate member 1410. The third hook 1412 can further secure the lever structure 1402b to the handle 1404 on the support arm 120 (FIG. 14A). It will be appreciated that lever structure 1402a, 1402b of FIGS. 14A-14C can include any suitable number of hooks (e.g., one, two, three, four, five, or more hooks), and the hooks can be at any suitable location on the first elongate member 1406 and/or the second elongate member 1410.

Figure 14D:
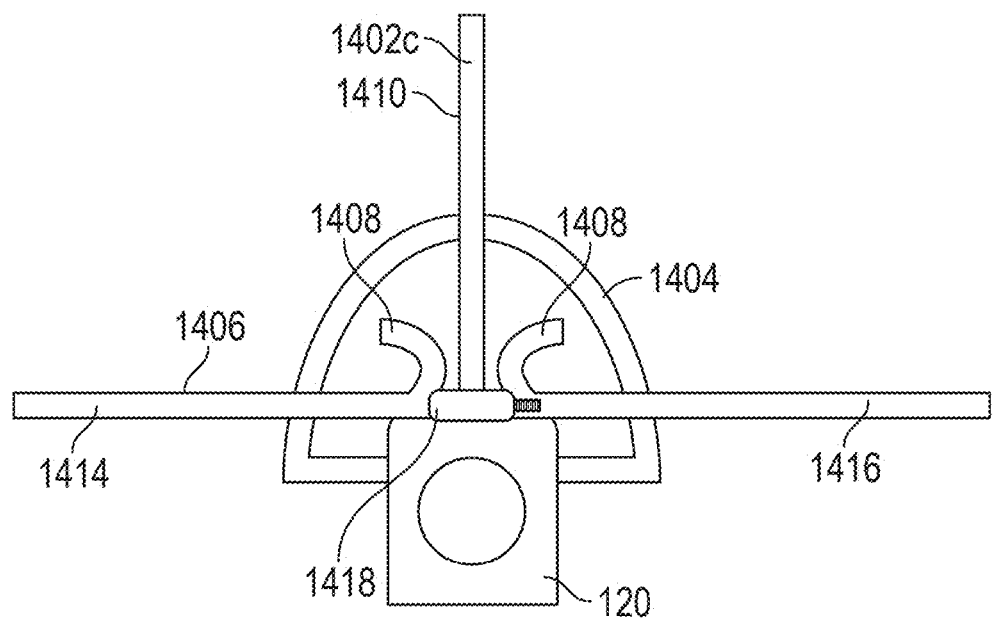
FIGS. 14D and 14E illustrate an adjustable lever structure configured in accordance with embodiments of the present technology.
Figure 14E:
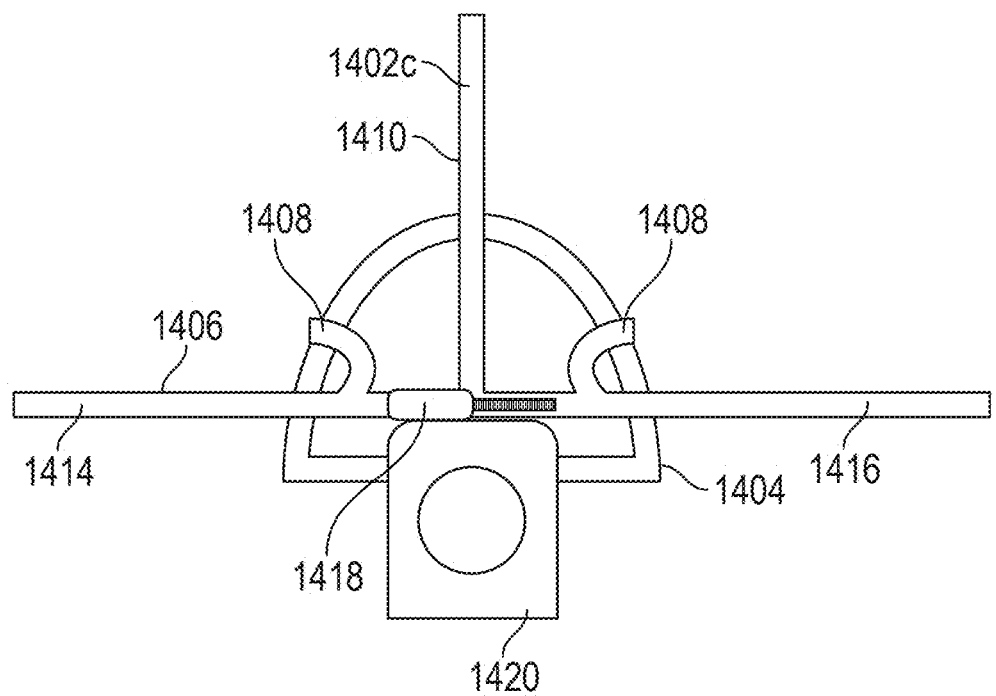

FIGS. 14D and 14E are partially schematic cross-section views of an adjustable lever structure 1402c coupled to the handle 1404 of the imaging apparatus 104, in accordance with embodiments of the present technology. Although the lever structure 1402c is depicted as having two hooks 1408 (e.g., similar to the lever structure 1402a of FIGS. 14A and 14B), in other embodiments, the lever structure 1402c can instead have three hooks (e.g., similar to the lever structure 1402b of FIG. 14C). Referring first to FIG. 14D, the first elongate member 1406 of the lever structure 1402c can include a first section 1414 and a second section 1416 connected to each other by an adjustable connection 1418. The adjustable connection 1418 can allow the first and second sections 1414, 1416 to be moved (e.g., translated) relative to each other along the longitudinal axis of the first elongate member 1406. The adjustable connection 1418 can be any suitable joint or mechanism that permits movement of the first section 1414 relative to the second section 1416, such as a slidable mechanism (e.g., a slidable bolt), a screw mechanism (e.g., a threaded bolt), a spring-loaded mechanism, or a combination thereof.

The first and second sections 1414, 1416 can each include at least one hook 1408, such that the distance between the hooks 1408 can be increased or decreased by changing the separation between the first and second sections 1414, 1416. For example, the hooks 1408 can be positioned closer together in a retracted configuration (FIG. 14D) when initially positioning the lever structure 1402c on the handle 1404, and can then be pushed outwards into an extended configuration (FIG. 14E) to contact and grip the handle 1404. This approach can make it easier to connect the lever structure 1402c to the handle 1404, while also providing a tighter fit to prevent the lever structure 1402c from inadvertently becoming dislodged when force is applied.

In some embodiments, the systems, methods, and devices disclosed herein reduce or eliminate unwanted movements during manual rotation, as measured by some or all of the following metrics: (1) imaging arm motion (e.g., as measured by an IMU or other motion sensor), (2) amount and type of unwanted motion in the projection images generated by the detector, (3) image quality of the 3D reconstruction generated from the projection images, and/or (4) physical distance between the imaging arm and the support arm. Each of these metrics is described in detail below.

First, as previously discussed with respect to FIG. 11, in the absence of any stabilization, the detector exhibits sudden shifts, oscillations, and/or other unwanted movements. When stabilized with shim structures and/or by rotation from the support arm, these undesirable movements can be significantly reduced to produce a relatively smooth and unidirectional rotation of the detector.

Second, in the absence of stabilization, undesirable motions (e.g., caused by weight shifts and/or flexing of the imaging arm) can be seen in the projection images as a sudden jump in all the structures in the field of view in the same direction simultaneously. This can indicate that the center of rotation of the detector was rapidly shifting back and forth, rather than maintaining a single center of rotation, since all the structures moved together in the same direction (whereas during a rotation, there are often structures moving in opposite directions based on depth). Further, during and/or after the initial shift, the structures may reverse direction briefly as the imaging arm moves backwards with the oscillations. When the imaging arm is stabilized using shim structures and/or the other techniques described herein, the sudden jumps in the projection image and/or reversed movements can be reduced or eliminated entirely.

Third, it may be difficult or impossible to generate coherent 3D reconstructions without using the stabilization techniques described herein. For example, the unwanted motions of the detector can change the center of rotation, thus causing some or all of the structures in the 3D reconstruction to be misaligned. In some instances, when imaging a marker bead in a phantom, the misalignment can cause the bead to appear as star-like shape in the 3D reconstruction, rather than a coherent spherical shape. Similarly, when imaging a cylindrical phantom with circular markers, the misalignment can cause the circles to appear as discontinuous half-circles in the 3D reconstruction, rather than a single continuous circle. This misalignment can be reduced or eliminated by using shim structures and/or rotating from the support arm to improve the stability of the imaging arm and/or detector during image acquisition, e.g., in combination with the calibration processes described below.

Fourth, in the absence of shim stabilization, the components of the imaging arm (e.g., the rails) and the support arm (e.g., the distal portion of the support arm) can be displaced by a distance within a range from 1 mm to 5 mm as measured at various angular rotation points. When shim structures are used, it may be nearly impossible for the imaging arm rails to move relative to the support arm since the shim structures can reduce or prevent the laxity between these components, thus producing a smoother, more uniform motion during image acquisition.

B. Sensors and Methods for Pose Estimation

Referring again to FIG. 1A, as previously discussed, during an mrCBCT procedure, the imaging arm 108 can be rotated to a plurality of different angles while the detector 112 obtains 2D images of the patient's anatomy. In some embodiments, to generate a 3D reconstruction from the 2D images, the pose of the imaging arm 108 needs to be determined for each image with a high degree of accuracy. However, as described above, a manually-operated imaging apparatus such as a mobile C-arm apparatus may lack the capability to track the pose of the imaging arm 108 with sufficient accuracy for CBCT purposes.

Accordingly, the system 100 can include at least one sensor 154 for tracking the pose of the imaging arm 108 during a manual rotation. The sensor 154 can be positioned at any suitable location on the imaging apparatus 104. In the illustrated embodiment, for example, the sensor 154 is positioned on the detector 112. Alternatively or in combination, the sensor 154 can be positioned at a different location, such as on the radiation source 110, on the imaging arm 108 (e.g., at or near the first end portion 114, at or near the second end portion 116), on the support arm 120 (e.g., at or near the distal portion 122, at or near the proximal portion 124), and so on. Additionally, although FIG. 1A illustrates a single sensor 154, in other embodiments, the system 100 can include multiple sensors 154 (e.g., two, three, four, five, or more sensors 154) distributed at various locations on the imaging apparatus 104. For example, the system 100 can include a first sensor 154 on the detector 112, a second sensor 154 on the radiation source 110, etc. The sensors 154 can be removably coupled or permanently affixed to the imaging apparatus 104.

In some embodiments, because the spatial configuration of the various components of the imaging apparatus 104 are known, the pose of the imaging arm 108 can be correlated to the pose of other components of the imaging apparatus 104. For example, in embodiments where the detector 112 is in a fixed position and orientation with respect to the imaging arm 108, the pose of the detector 112 can be calculated from the pose of the imaging arm 108, and vice-versa. Accordingly, any embodiment described herein as using the pose of the imaging arm 108 can alternatively or additionally be adapted to use the pose of the detector 112 (or any other suitable component of the imaging apparatus 104).

The sensor 154 can be any sensor type suitable for tracking the pose (e.g., position and/or orientation) of a movable component. For example, the sensor 154 can be configured to track the rotational angle of the imaging arm 108 during a manual propeller rotation. Examples of sensors 154 suitable for use with the imaging apparatus 104 include, but are not limited to, motion sensors (e.g., IMUs, accelerometers, gyroscopes, magnetometers), light and/or radiation sensors (e.g., photodiodes), image sensors (e.g., video cameras), EM sensors (e.g., EM trackers or navigation systems), shape sensors (e.g., shape sensing fibers or cables), or suitable combinations thereof. In embodiments where the system 100 includes multiple sensors 154, the sensors 154 can be the same or different sensor types. For example, the system 100 can include two motion sensors, a motion sensor and a photodiode, a motion sensor and a shape sensor, etc.

In some embodiments, the sensor 154 includes at least one motion sensor, such as a 9-axis IMU having an accelerometer, gyroscope, and/or magnetometer. The motion sensor can be configured to generate motion data (e.g., position and/or orientation data over time) as the imaging arm 108 is manually rotated. The motion sensor can be attached to any portion of the imaging apparatus 104 that undergoes rotation, such as the detector 112, radiation source 110, imaging arm 108, support arm 120, or a combination thereof. In some embodiments, two or more motion sensors are used, with each motion sensor being attached to a different portion of the imaging apparatus 104 (e.g., a first motion sensor can be attached to the detector 112 and a second motion sensor can be attached to the radiation source 110).

Figure 15:
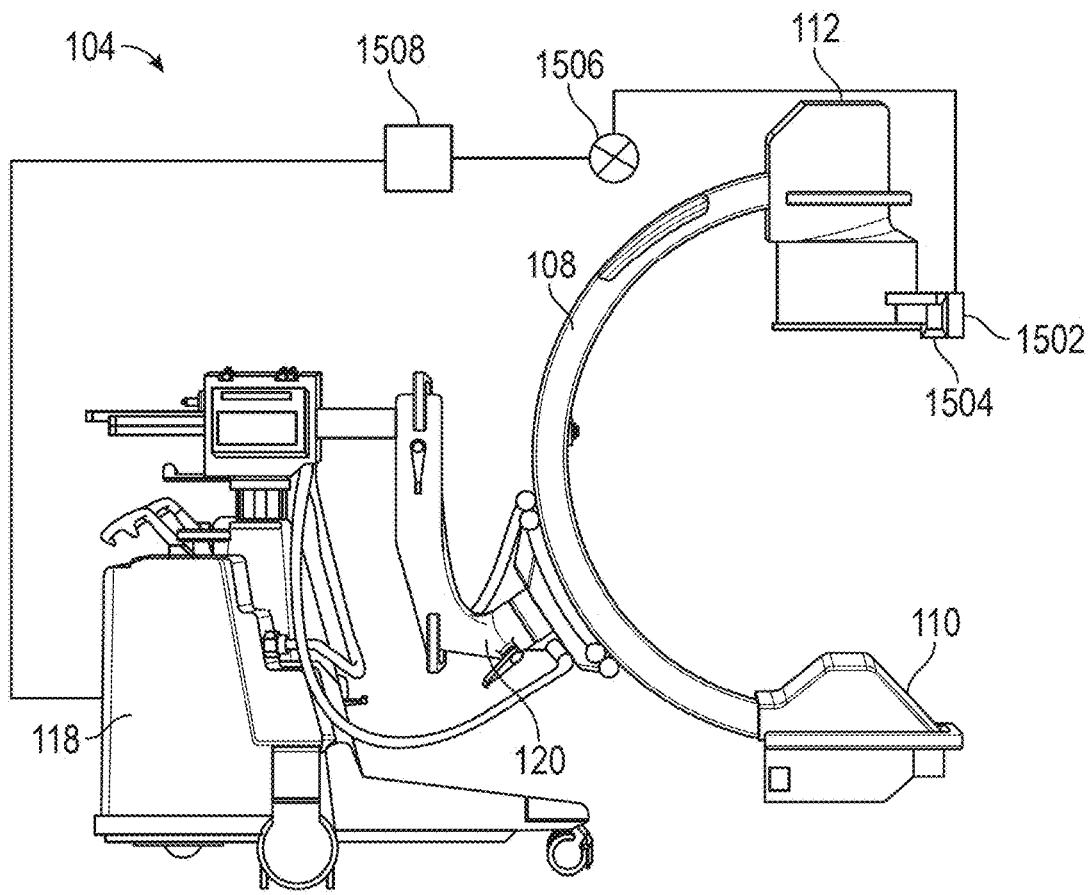
FIG. 15 illustrates a motion sensor coupled to an imaging apparatus in accordance with embodiments of the present technology.

FIG. 15 is a partially schematic view of a motion sensor 1502 coupled to the imaging apparatus 104 via an attachment device 1504 configured in accordance with embodiments of the present technology. The motion sensor 1502 is coupled to the attachment device 1504, which in turn is coupled to the detector 112 of the imaging apparatus 104. In the embodiment of FIG. 15, the attachment device 1504 is configured to attach to the lateral surface of the detector 112. In other embodiments, however, the attachment device 1504 can be configured to attach to a different portion of the detector 112, such as the upper surface, lower surface, etc. Optionally the detector 112 and/or the attachment device 1504 can include alignment markings (e.g., lines, arrows, or other indicators) to guide the user in placing the attachment device 1504 (and thus, the motion sensor 1502) at a predetermined position and/orientation on the detector 112.

In the illustrated embodiment, the attachment device 1504 is configured as a clip or bracket that attaches to the edge of the detector 112 at or near the lower surface. The clip can include a small, vertically-oriented peg having a short lip or overhanging protrusion that grips onto the lower edge of the detector 112. Optionally, the clip can be spring-loaded, can include a rotatable screw, and/or can be otherwise configured to lock into place once positioned at the desired location on the detector 112. In other embodiments, however, the attachment device 1504 can be configured differently. For example, the attachment device 1504 can instead be configured as a container for holding the motion sensor 1502, such as a small rectangular box that can be placed flat against a flat portion of the detector 112. The container can include loops, handles, apertures, etc., allowing the container to be secured to the detector 112 using straps (e.g., straps made of velcro or other adhesive material) and/or other fasteners. Optionally, the attachment device 1504 can be omitted altogether, the motion sensor 1502 can instead be coupled directly to the detector 112 via adhesives, fasteners, magnets, straps, etc.

The motion sensor 1502 can generate motion data indicative of the pose of the imaging arm 108. For example, as the imaging arm 108 moves (e.g., during a manual propeller rotation), the motion sensor 1502 can output motion data representing the position and/or orientation (e.g., rotational angle) of the imaging arm 108 over time. In some embodiments, the motion sensor 1502 generates motion data independently of the image acquisition performed by the detector 112. Accordingly, in order to determine the pose of the imaging arm 108 for each image obtained by the detector 112, the motion data from the motion sensor 1502 can be temporally synchronized or otherwise associated with the images from the detector 112.

The synchronization can be performed in many different ways. In the illustrated embodiment, for example, the motion sensor 1502 is coupled to a controller 1506 (e.g., an Arduino microcontroller), which in turn is coupled to an image output device 1508. The image output device 1508 can receive the images generated by the detector 112 (e.g., in video format or any other suitable format). As shown in FIG. 15, the images produced by the detector 112 can be transmitted to the base 118, and the base 118 can be coupled to the image output device 1508. In other embodiments, the detector 112 can be coupled directly to the image output device 1508. The connections between the motion sensor 1502, controller 1506, image output device 1508, detector 112, and base 118 can be wired or wireless connections.

The controller 1506 can collect the motion data from the motion sensor 1502 in real time and temporally synchronize each image acquired by the image output device 1508 with the motion data from the motion sensor 1502. For example, the controller 1506 can time stamp the motion data received from the motion sensor 1502. The controller 1508 can then compare the time stamps for the motion data to the time stamps on the image data, and can associate each image with motion data that was acquired at the same time point or over a similar time period. Thus, each image recorded from the image output device 1508 can be associated with a corresponding angle (or a very small range of angles) from the motion sensor 1502.

Figure 16:
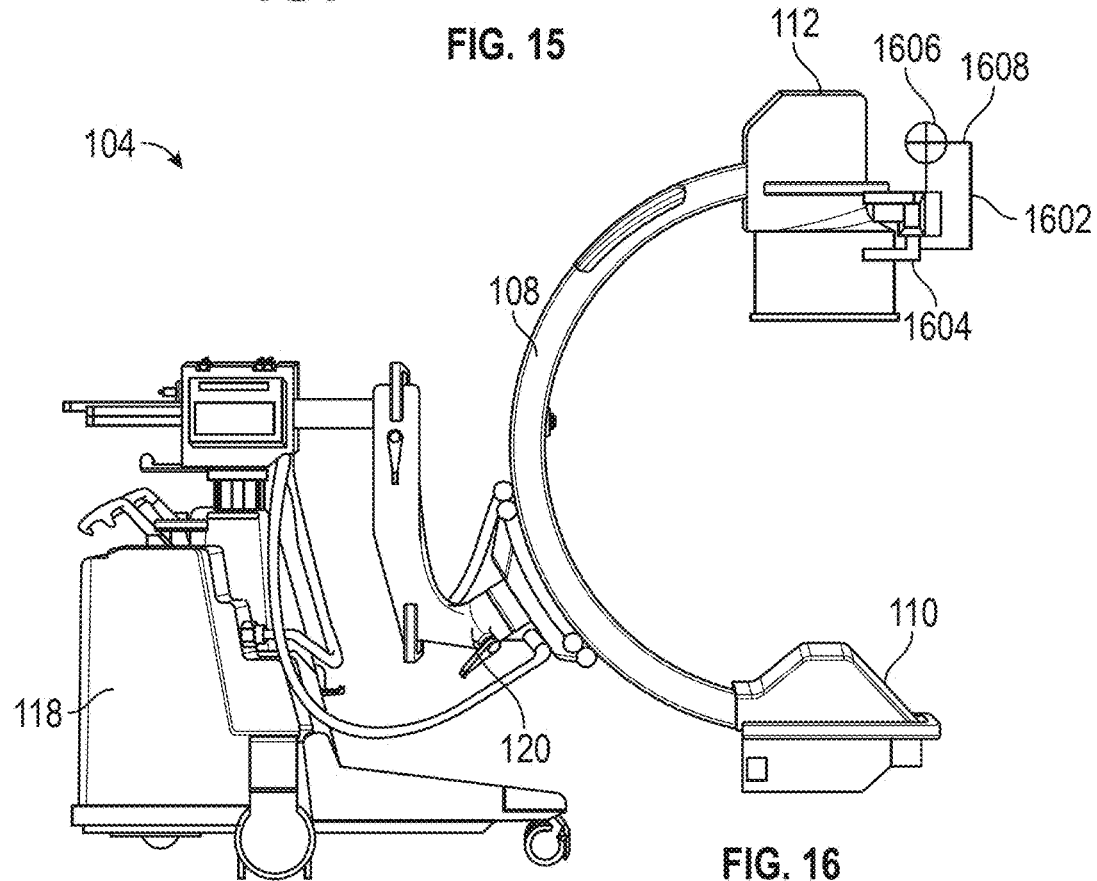
FIG. 16 illustrates a motion sensor and a radiation sensor coupled to an imaging apparatus in accordance with embodiments of the present technology.

FIG. 16 is a partially schematic view of a motion sensor 1602 and radiation sensor 1604 attached to the imaging apparatus 104 in accordance with embodiments of the present technology. The motion sensor 1602 (e.g., IMU) and radiation sensor 1604 can be coupled to an attachment device 1606. The attachment device 1606 can be generally similar to the attachment device 1504 of FIG. 15, except that the attachment device 1606 is configured to support both the motion sensor 1602 and the radiation sensor 1604. For example, the attachment device 1606 can be a clip with a vertically-oriented peg that can be temporarily coupled to the detector 112. The attachment device 1606 can be mounted on the detector 112 such that the motion sensor 1602 is located along the lateral surface of the detector 112, while the radiation sensor 1604 protrudes at least partially into the path of the radiation beam output by the detector 112.

The radiation sensor 1604 can be any device capable of detecting exposure to radiation (e.g., x-rays), such as a photodiode. For example, the photodiode can include a scintillator made of silicon-based materials and/or other suitable materials, and can be provided with or without a signal amplifier. Accordingly, the radiation sensor 1604 can accurately measure the time of image acquisition based on exposure radiation passing through the radiation sensor 1604 toward the detector 112.

The motion sensor 1602 and radiation sensor 1604 can each be coupled to a controller 1608 (e.g., an Arduino microcontroller) via wired or wireless connections. When the radiation sensor 1604 detects radiation, it can send a signal to the controller 1608 to generate a time stamp indicating that an image was acquired. Similarly, the controller 1608 can also determine time stamps for the motion data produced by the motion sensor 1602. Accordingly, the image acquisition timing can be linked to the timing of the rotational measurements from the motion sensor 1602, thus allowing each image generated by the detector 112 to be temporarily synchronized to the corresponding rotational angle of the imaging arm 108.

Figure 17A:
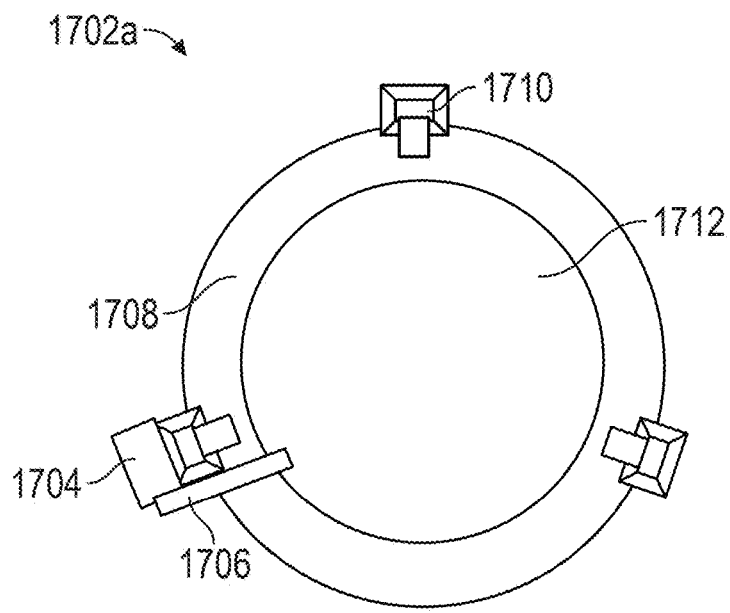
FIGS. 17A and 17B illustrate an attachment device configured in accordance with embodiments of the present technology.
Figure 17B:
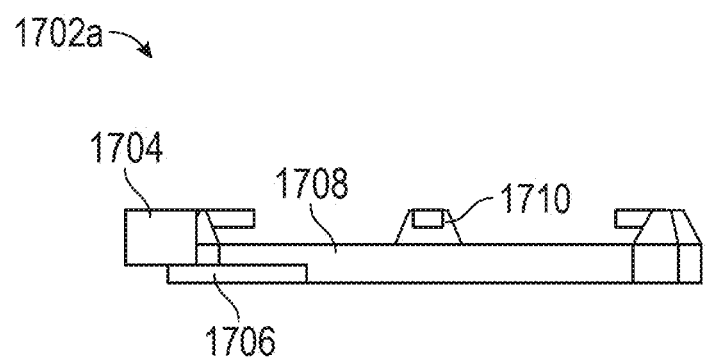
Figure 17C:
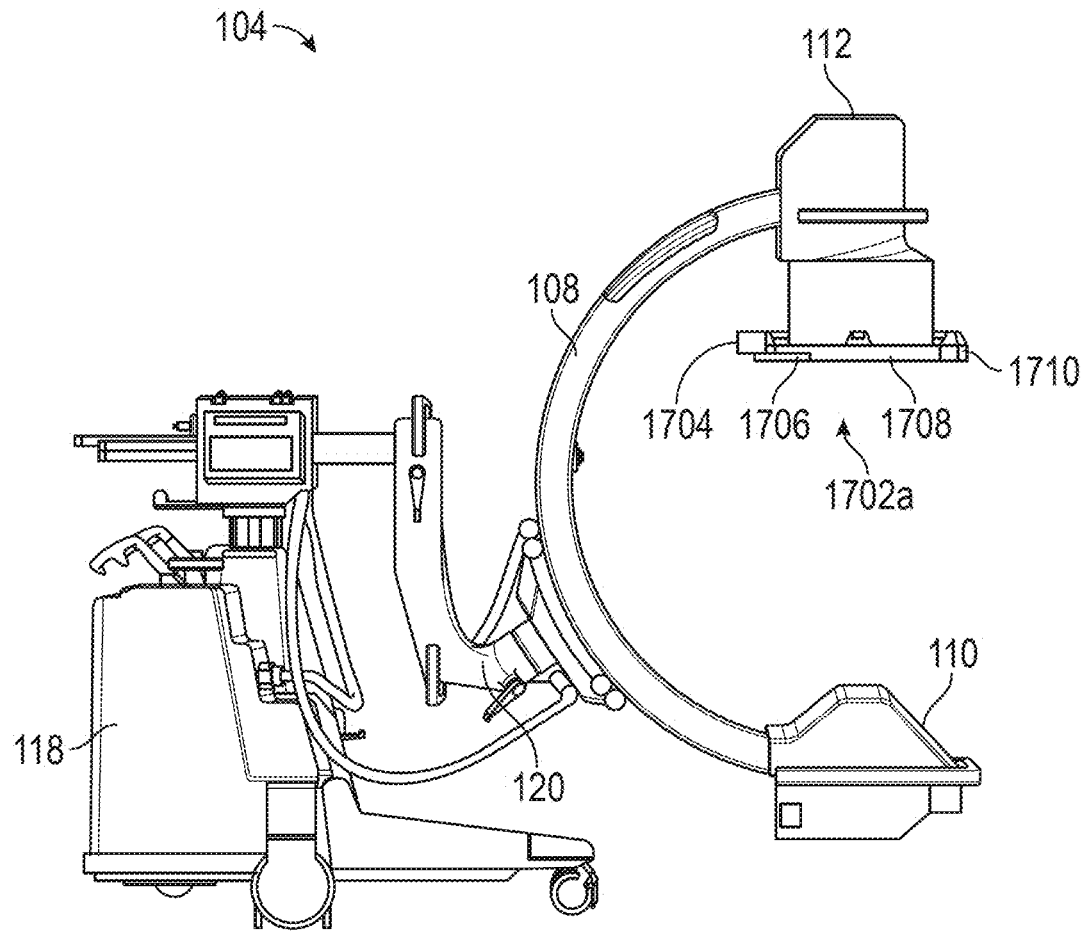
FIG. 17C illustrates the attachment device of FIGS. 17A and 17B coupled to an imaging apparatus, in accordance with embodiments of the present technology.

FIG. 17A is a top view of an attachment device 1702a, FIG. 17B is a side view of the attachment device 1702a, and FIG. 17C is a partially schematic illustration of the attachment device 1702a coupled to the imaging apparatus 104, in accordance with embodiments of the present technology. Referring first to FIGS. 17A and 17B together, the attachment device 1702a is configured to support a motion sensor 1704 (e.g., an IMU) and a radiation sensor 1706 (e.g., a photodiode). The attachment device 1702a can include a frame 1708 and one or more clips 1710 located along the periphery of the frame 1708. Although the frame 1708 is depicted as having a circular shape, in other embodiments, the frame 1708 can have a different shape, such as an oval, square, rectangular, or other suitable shape. The frame 1708 can include a central aperture 1712 to allow radiation to pass through. The frame 1708 can also be used to support a fiducial marker grid for a calibration procedure, as described in detail further below.

The clips 1710 can be configured to couple the attachment device 1702a to the detector 112 in a temporary or permanent manner. In some embodiments, the clips 1710 are small, vertically-oriented pegs located at the edge of the frame 1708, each having a short lip or overhanging protrusion to grip onto the edge of the detector 112. As best seen in FIG. 17C, the clips 1710 can secure the attachment device 1702a to the lower surface of the detector 112, with the frame 1708 located partially or entirely out of the radiation path of the detector 112 to avoid attenuating or otherwise interfering with the radiation beam. Optionally, the detector 112, frame 1708, and/or clips 1710 can include alignment markers to guide the user in placing the attachment device 1702a at the appropriate position and/or orientation on the detector 112.

In some embodiments, the attachment device 1702a includes one or more sites along the frame 1708 and/or clips 1710 for attaching the motion sensor 1704 and/or radiation sensor 1706. For example, the motion sensor 1704 and radiation sensor 1706 can both be coupled to one of the clips 1710, similar to the configuration of the attachment device 1606 of FIG. 16. The motion sensor 1704 can be located along an edge of the attachment device 1702a away from the path of the radiation beam, while the radiation sensor 1706 can protrude at least partially under the frame 1708 and into path of the radiation beam. In other embodiments, however, the motion sensor 1704 and/or radiation sensor 1706 can be at different locations on the attachment device 1702a. The motion sensor 1704 and/or radiation sensor 1706 can each be removably coupled to the attachment device 1702a or permanently affixed to the attachment device 1702a. The motion sensor 1704 and radiation sensor 1706 can be coupled to other components (e.g., controller, image output device) for temporally synchronizing the output of the motion sensor 1704 with the images produced by the detector 112, as discussed above with respect to FIGS. 15 and 16. Optionally, the radiation sensor 1706 can be omitted, such that the attachment device 1702a is used to support the motion sensor 1704 only.

Figure 17D:
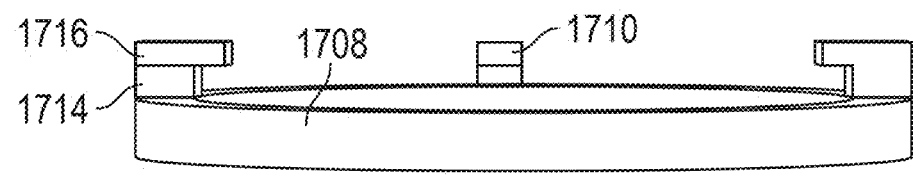
FIG. 17D illustrates another attachment device configured in accordance with embodiments of the present technology.

FIG. 17D is a side view of an attachment device 1702b configured in accordance with embodiments of the present technology. The attachment device 1702b can be generally similar to the attachment device 1702a of FIGS. 15A-15C, except that the attachment device 1702b includes a spring-loaded clip 1714 in place of one or more of the clips 1710. The clip 1714 can include a spring-loaded protrusion 1716 that can be retracted when positioning the attachment device 1702b on the detector 112. After the attachment device 1702b is positioned at the desired location, the spring-loaded protrusion 1716 can lock into place around the edge of the detector 112 to secure the frame 1708 to the detector 112. The clip 1714 can include a release mechanism (not shown) to retract the spring-loaded protrusion 1716 when removing and/or mounting the frame 1708. The attachment device 1702b can optionally be configured to support a motion sensor and/or radiation sensor (not shown in FIG. 17D), as discussed above with reference to FIGS. 17A and 17B. The attachment device 1702b can also be used to support a fiducial marker grid for a calibration procedure, as described in detail further below.

Figure 17E:
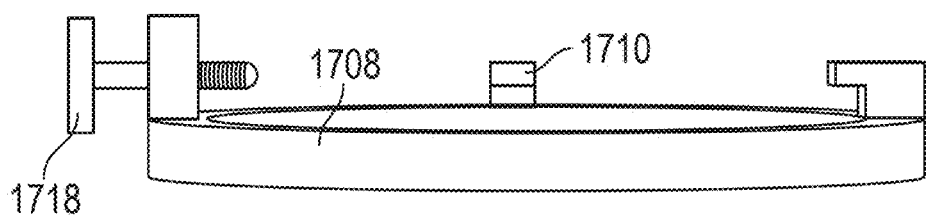
FIG. 17E illustrates another attachment device configured in accordance with embodiments of the present technology.

FIG. 17E is a side view of an attachment device 1702c configured in accordance with embodiments of the present technology. The attachment device 1702c can be generally similar to the attachment device 1702a of FIGS. 15A-15C, except that the attachment device 1702c includes a screw 1718 in place of one or more of the clips 1710. The screw 1718 can be in a retracted position when placing the attachment device 1702c on the detector 112. After the attachment device 1702c is positioned at the desired location, the screw 1718 can be rotated to advance the screw 1718 toward the detector 112. The screw 1718 can be advanced until it engages the edge of the detector 112, thus securing the frame 1708 to the detector 112. To release the attachment device 1702c, the screw 1718 can be rotated in the opposite direction to retract the screw 1718 away from the detector 112. The attachment device 1702c can optionally be configured to support a motion sensor and/or radiation sensor (not shown in FIG. 17E), as discussed above with reference to FIGS. 17A and 17B. The attachment device 1702c can also be used to support a fiducial marker grid for a calibration procedure, as described in detail further below.

Referring again to FIG. 1A, the present technology also provides other techniques that may be used to estimate the pose of the imaging arm 108, alternatively or in addition to the motion sensor-based techniques described herein. For example, in some embodiments, the pose of the imaging arm 108 can determined using one or more imaging devices (e.g., video cameras) positioned around the imaging apparatus 104. In such embodiments, the system 100 can include one or more fiducial markers placed at known locations, such as on the patient 102, operating table 152, and/or the components of the imaging apparatus 104 (e.g., detector 112, radiation source 110, imaging arm 108, and/or support arm 120). The imaging devices can track the markers as the imaging arm 108 is rotated to determine the pose of the imaging arm 108.

In another example, the system 100 can include a 3D scanner coupled to the imaging arm 108. The 3D scanner can be configured to scan a reference object (e.g., a block) attached to a fixed location relative to the imaging arm 108, such as to the operating table 152 and/or the patient's body. The reference object can have a known geometry, such that the pose of the imaging arm 108 can be determined from the pose of the reference object within the scans.

As another example, the pose of the imaging arm 108 can be determined using shape sensors (e.g., shape-sensing fibers or cables). For example, one portion of a shape-sensing cable can be attached to the operating table 152, and another portion to the detector 112. Alternatively or in combination, one or more shape-sensing cables can be attached to other locations, such as to the patient 102, radiation source 110, imaging arm 108, support arm 120, or suitable combinations thereof. When the imaging arm 108 is rotated, the change in shape of the shape-sensing cable can be measured and used to calculate the rotational angle of the imaging arm 108.

In a further example, a shape sensor can be carried by a tool within the patient's body, such as a shape-sensing endoscope. For example, the tool can output shape data that allows the 3D pose of the tool to be accurately determined before image acquisition. The pose of the internal shape sensor in each projection image can be used to estimate the pose of the imaging arm 108 when the image was acquired. For example, the actual pose of the tool can be output as a virtual rendering or representation of the 3D shape of the tool inside the patient's body. The pose of the internal shape sensor within the images can be identified (e.g., using known computer vision and/or image processing techniques), and registered to the virtual representation of the actual pose. The registration can be used to determine the pose of the imaging arm with respect to the tool and/or the patient's body for each acquired image.

In yet another example, an EM sensing system can be used to determine the pose of the imaging arm 108 during rotation. For example, one or more EM sensors or trackers can be positioned at various locations, such as on the patient 102, operating table 152, detector 112, radiation source 110, imaging arm 108, support arm 120, or suitable combinations thereof. The position and/orientation of each EM sensor can be tracked and used to estimate the angle of the imaging arm 108. Optionally, an EM sensor can also be carried by a tool within the patient's body, such as an endoscope, biopsy needle, ablation probe, etc. The internal EM sensor can be used in combination with one or more externally-located EM sensors to perform pose estimation.

In some embodiments, the pose of the imaging arm is estimated using a fiducial marker board placed near the patient's body, as an alternative to or in combination with the other pose estimation techniques described herein. Conventional fiducial marker boards for intraprocedural image-based pose estimation (e.g., for tomosynthesis) are typically flat structures with one or more layers of markers. Conventional fiducial marker boards are generally unsuitable for imaging techniques involving a large angular range of rotation such as CBCT because the markers in the board may not be visible at certain angles due to the limited vertical height of the board. For example, the markers in a conventional fiducial marker board may be obscured or disappear entirely from the field of view when imaged from a lateral angle (e.g., at or near 180°). In contrast, the fiducial marker boards of the present technology can have a 3D shape in which at least some of the markers lie in different planes or are otherwise sufficiently vertically separated so most or all of the markers remain visible over a wide range of imaging angles. This allows for estimation of the imaging arm pose over a wide range of imaging angles. Additionally, conventional fiducial marker boards are generally unsuitable for determining the geometric calibration parameters of the imaging apparatus (e.g., piercing point, pitch, roll, etc.). The fiducial marker boards disclosed herein can be combined with a fiducial marker phantom in order to perform geometric calibration, which can improve the accuracy of the CBCT reconstruction as described in greater detail below.

Figure 18A:
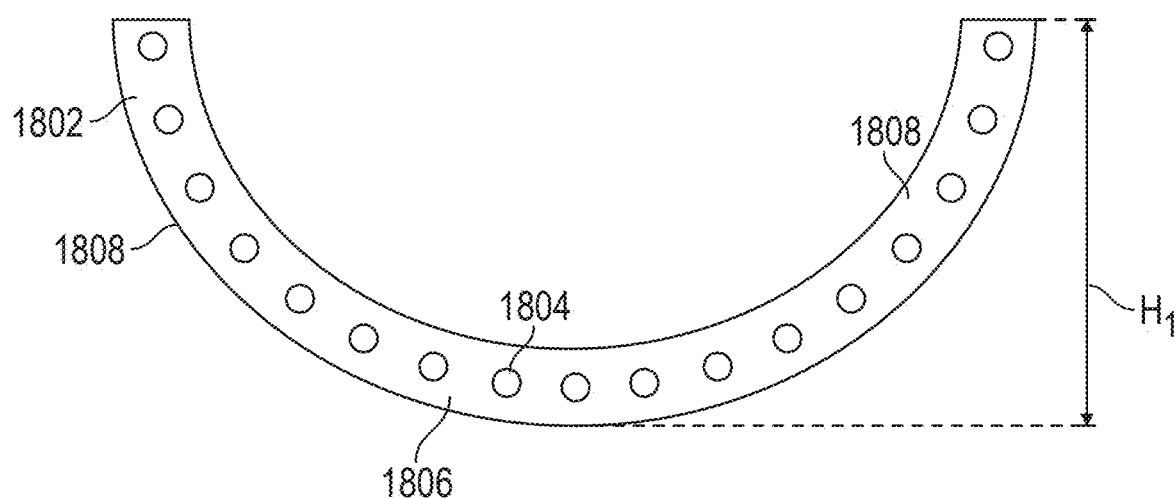
FIGS. 18A and 18B illustrate a fiducial marker board for pose estimation in accordance with embodiments of the present technology.
Figure 18B:
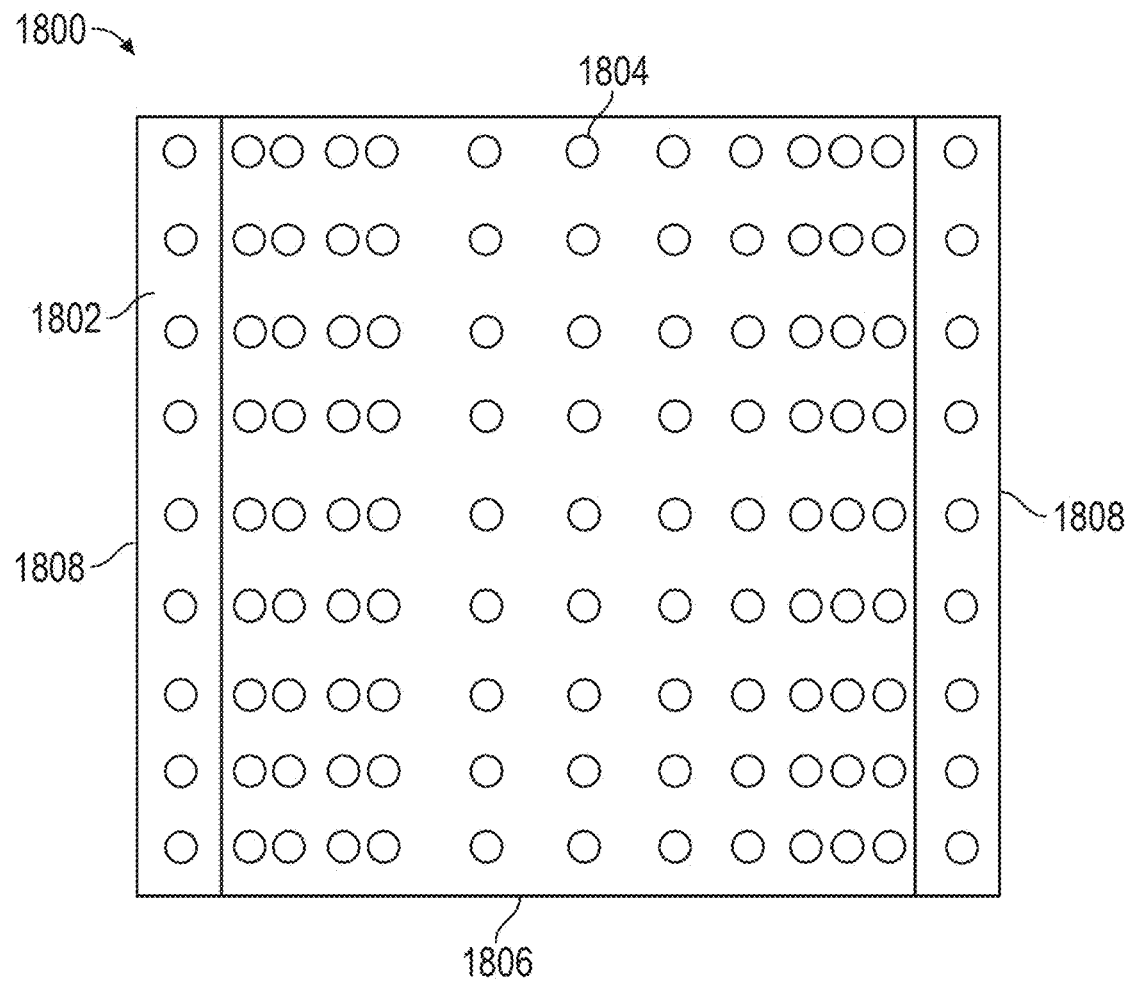

FIG. 18A is a side view of a fiducial marker board 1800 for determining the pose of an imaging arm, and FIG. 18B is a top view of the fiducial marker board 1800, in accordance with embodiments of the present technology. The fiducial marker board 1800 can be positioned adjacent or near a patient's body to provide a reference for estimating a pose of an imaging arm. The fiducial marker board 1800 includes a substrate 1802 (e.g., a radiolucent material) containing a plurality of fiducial markers 1804 (e.g., beads, bearings, flattened disks, etc., made of a radiodense or radiopaque material). The markers 1804 can be arranged in a known geometry (e.g., a grid, pattern, or other spatial configuration) such that when the fiducial marker board 1800 is imaged by an imaging apparatus, the pose of the imaging apparatus (e.g., the angle of the imaging arm) relative to the fiducial marker board 1800 can be determined based on the locations of the markers 1804 in the acquired images, in accordance with techniques known to those of skill in the art.

As best seen in FIG. 18A, the substrate 1802 can have a non-planar shape (e.g., a curved, semicircular, semioval, and/or U shape) such that at least some of the markers 1804 are in different planes. In the illustrated embodiment, for example, the substrate 1802 includes a base region 1806 and a pair of curved sidewalls 1808 extending upward from the base region 1806 by a height $H_1$. For example, the height $H_1$ can be at least 1 cm, 2 cm, 5 cm, 10 cm, 15 cm, 20 cm, or 30 cm. In some embodiments, the height $H_1$ is greater than or equal to the anterior-posterior height of a patient's torso. The height $H_1$ can be sufficiently large such that most or all of the markers 1804 remain visible even when the fiducial marker board 1800 is imaged from a lateral angle (e.g., at or near 180° relative to the surface of the table). Accordingly, the fiducial marker board 1800 can be used to estimate the pose of the imaging arm over a wider range of angles compared to flat fiducial marker boards in which most or all of the markers lie within a single plane. Optionally, the sidewalls 1808 can be movably coupled to the base region 1806 (e.g., via a sliding or pivoting connection) so that the height $H_1$ can be adjusted, e.g., to accommodate different body sizes and/or imaging setups.

During a medical procedure, the fiducial marker board 1800 can be placed on a operating table with the base region 1806 resting on a surface of the table, and the sidewalls 1808 extending upward away from the surface. A portion of the patient's body (e.g., the patient's torso) can be positioned on the fiducial marker board 1800 in the cavity formed by the base region 1806 and sidewalls 1808. A plurality of 2D projection images can be acquired while the imaging arm of the imaging apparatus is rotated to a plurality of different angles relative to the patient's body and the fiducial marker board 1800. The 2D projection images can then be analyzed to identify the locations of the markers 1804 in each image, e.g., using computer vision algorithms or other suitable algorithms. Optionally, in embodiments where the markers 1804 are made of a metallic material, the images can be processed to remove any imaging artifacts caused by the presence of the metallic material. The identified marker locations can be used to estimate the rotational angle of the imaging arm for each image, using techniques known to those of skill in the art.

FIGS. 18C-18G illustrate additional examples of fiducial marker boards 1810-1840 suitable for use with the present technology. The features of the fiducial marker boards 1810-1840 can be generally similar to the features of the fiducial marker board 1800 of FIGS. 18A and 18B. Accordingly, the discussion of the fiducial marker boards 1810-1840 of FIGS. 18C-18G will be limited to those features that differ from the embodiments of FIGS. 18A and 18B. Any of the features of the fiducial marker boards 1810-1840 can be combined with each other and/or with the features of the fiducial marker board 1800 of FIGS. 18A and 18B.

Figure 18C:
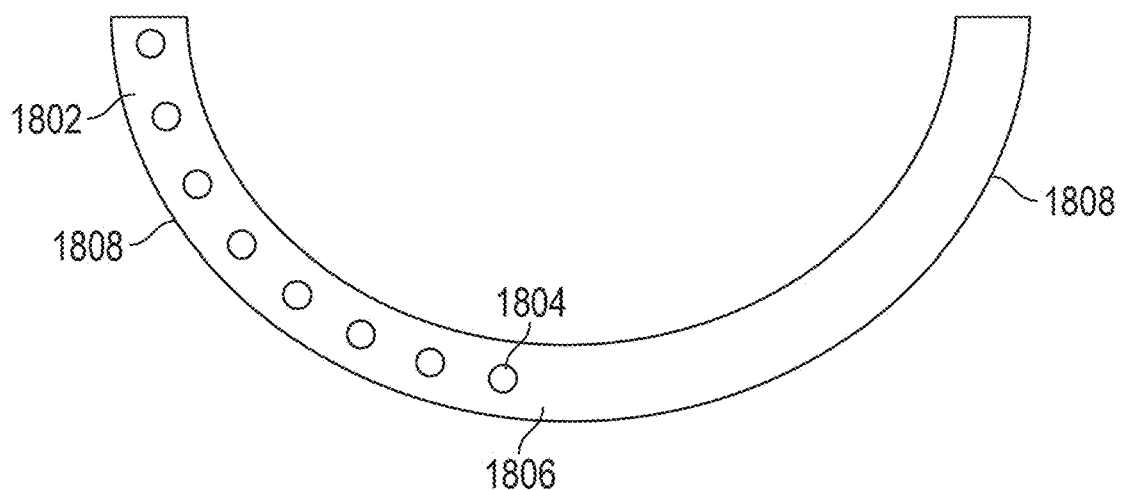
FIG. 18C illustrates another fiducial marker board in accordance with embodiments of the present technology.

FIG. 18C is a side view of another fiducial marker board 1810 configured in accordance with embodiments of the present technology. As shown in FIG. 18C, the markers 1804 in the fiducial marker board 1810 are located only in a portion of the substrate 1802, rather than being distributed throughout the entirety of the substrate 1802. For example, the markers 1804 can be localized to one lateral side or half of the substrate 1802, such that only one of the sidewalls 1808 includes markers 1804. This configuration can be used, for example, in situations where only a single side or section of the patient's body is to be imaged (e.g., during a bronchoscopic procedure performed within a single lung). In such situations, the fiducial marker board 1810 can be positioned so that the markers 1804 are near the side or section of the patient's body to be imaged.

Figure 18D:
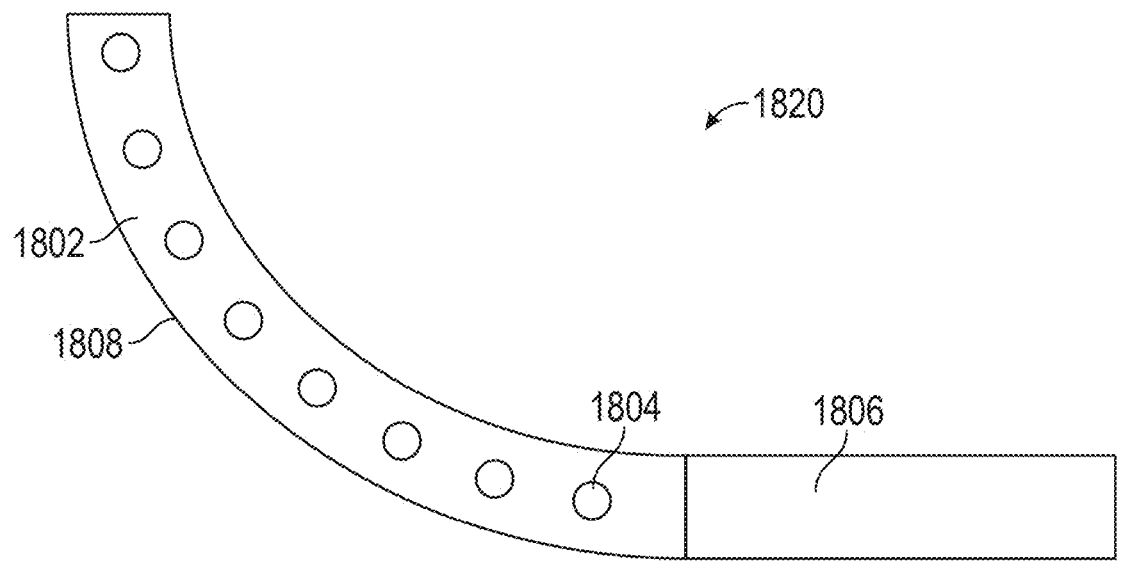
FIG. 18D illustrates yet another fiducial marker board in accordance with embodiments of the present technology.

FIG. 18D is a side view of yet another fiducial marker board 1820 configured in accordance with embodiments of the present technology. The fiducial marker board 1820 includes a single sidewall 1808, rather than two sidewalls 1808. In such embodiments, the base region 1806 can be extended to provide support for the sidewall 1808, such that the fiducial marker board 1820 is J-shaped. Although the base region 1806 is depicted without any markers 1804, in other embodiments the base region 1806 can also include markers 1804. The fiducial marker board 1820 can be used when imaging a single side or section of the patient's body. In such situations, the fiducial marker board 1820 can be positioned so that the single sidewall 1808 is near the side or section of the patient's body to be imaged.

Figure 18E:
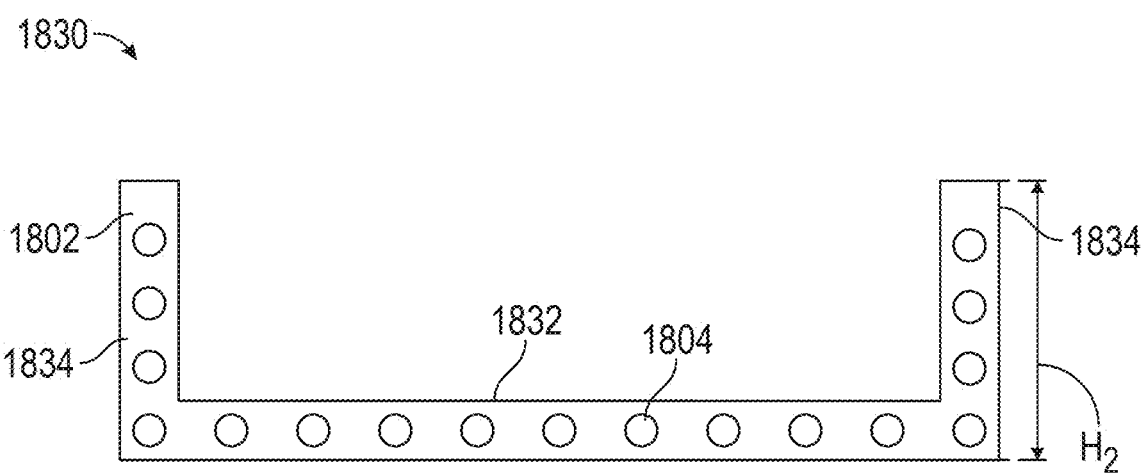
FIG. 18E illustrates another fiducial marker board in accordance with embodiments of the present technology.

FIG. 18E is a side view of a fiducial marker board 1830 configured in accordance with embodiments of the present technology. The fiducial marker board 1830 includes a flattened base region 1832 and a pair of straight sidewalls 1834. The sidewalls 1834 can be connected to the base region 1832 at any suitable angle, such as an angle greater than or equal to 90°, 110°, 120°, 130°, 140°, or 150°. The height $H_2$ of the sidewalls 1834 can be sufficiently large so that that most or all of the markers 1804 remain visible even when the fiducial marker board 1830 is imaged from a lateral angle, and can be identical or similar to the height $H_1$ of the fiducial marker board 1800 of FIGS. 18A and 18B. Optionally, the sidewalls 1834 can be movably coupled to the base region 1832 so the height $H_2$ can be adjusted, if desired.

Although the fiducial marker board 1830 is illustrated as including markers 1804 throughout the entirety of the substrate 1802, in other embodiments the fiducial marker board 1830 can include markers 1804 in only a portion of the substrate 1802 (e.g., similar to the fiducial marker board 1820 of FIG. 18C). Additionally, although the fiducial marker board 1830 is shown as having two sidewalls 1834, in other embodiments the fiducial marker board 1830 can include a single sidewall 1834 (e.g., similar to the fiducial marker board 1830 of FIG. 18D).

Figure 18F:
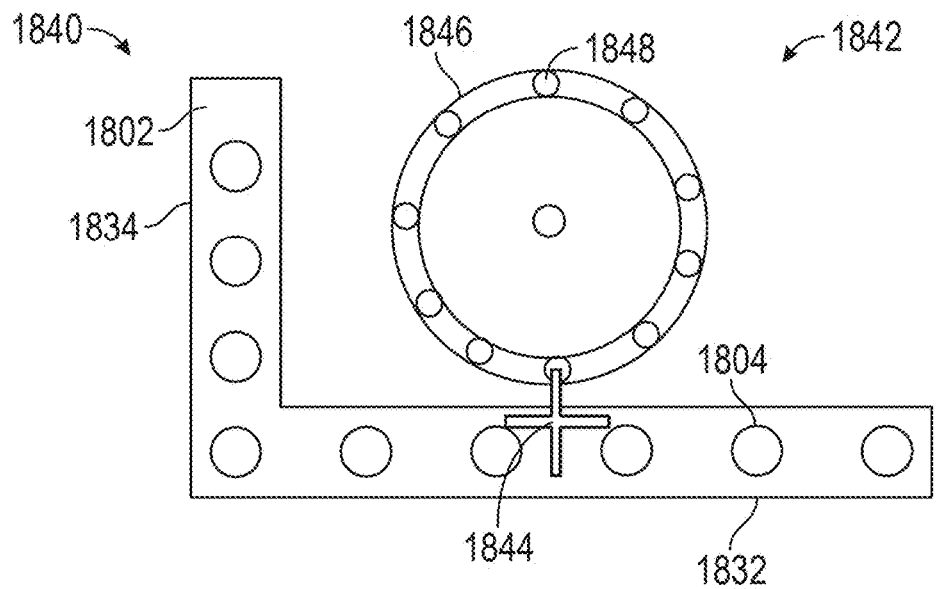
FIGS. 18F and 18G illustrate a fiducial marker board and a phantom in accordance with embodiments of the present technology.
Figure 18G:
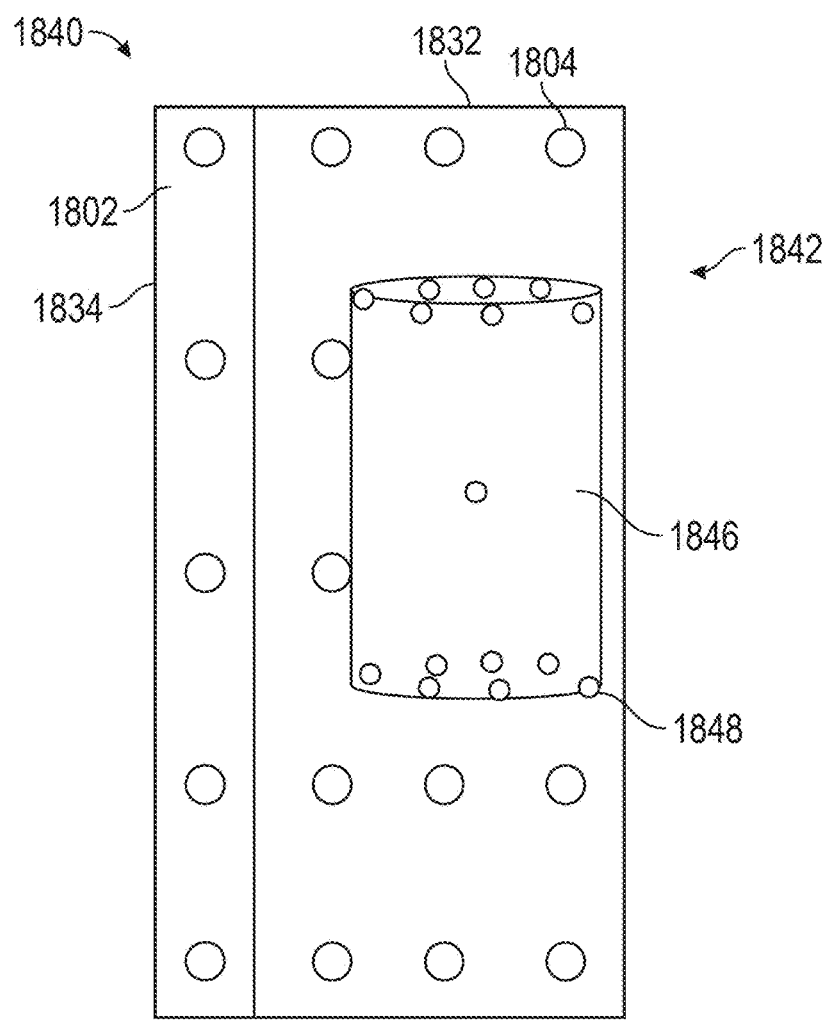

FIGS. 18F and 18G are side and top views, respectively, of a fiducial marker board 1840 together with a fiducial marker phantom 1842, in accordance with embodiments of the present technology. The fiducial marker board 1840 can be similar to the fiducial marker board 1830 of FIG. 18E, except that the fiducial marker board 1840 includes a single sidewall 1834 connected to the base region 1832. The phantom 1842 can be temporarily coupled to the fiducial marker board 1840 via one or more fasteners 1844 (e.g., pegs, screws, magnets, etc.). The phantom 1842 can include a respective substrate 1846 (e.g., a radiolucent material) containing a plurality of fiducial markers 1848 (e.g., beads, bearings, flattened disks, etc., made of a radiodense or radiopaque material). The markers 1848 can be arranged in a configuration suitable for performing geometric calibration, as described further below with respect to FIGS. 22A-22D.

As best seen in FIG. 18G, the phantom 1842 can be positioned over a portion of the base region 1832 that does not include any markers 1804. In such embodiments, when the fiducial marker board 1840 and phantom 1842 are imaged together (e.g., during a geometric calibration procedure), the markers 1804 of the fiducial marker board 1840 do not overlap the markers 1848 of the phantom 1842 in the acquired images, and thus can be identified and distinguished from each other. The use of the phantom 1842 together with the fiducial marker board 1840 for performing geometric calibration and image acquisition is described in further detail below with respect to FIG. 25A.

C. Methods for Imaging

Figure 19:
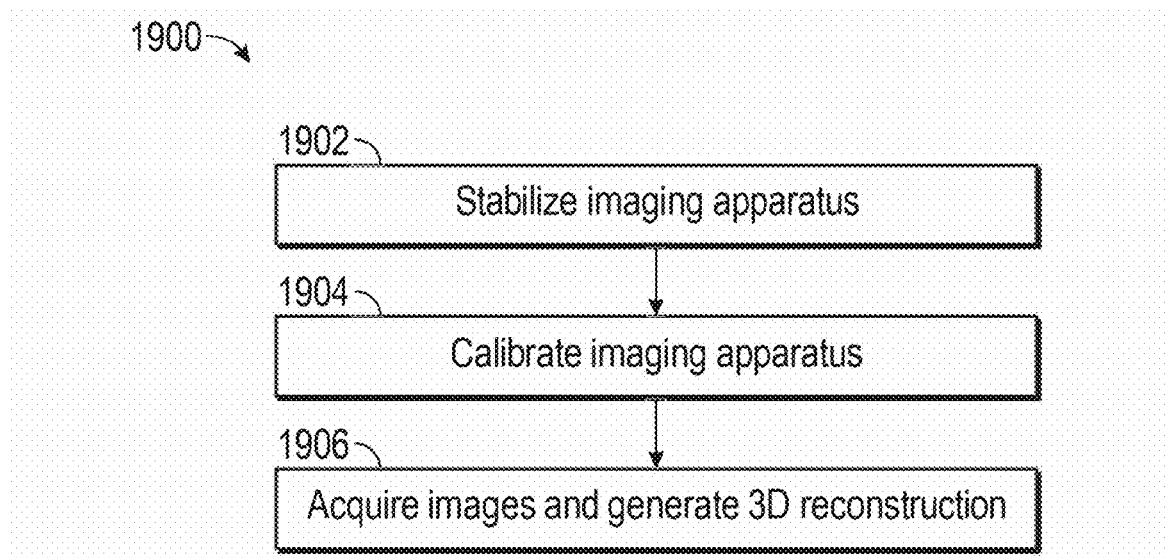
FIG. 19 is a flow diagram illustrating a method for operating an imaging apparatus, in accordance with embodiments of the present technology.
Figure 23A:
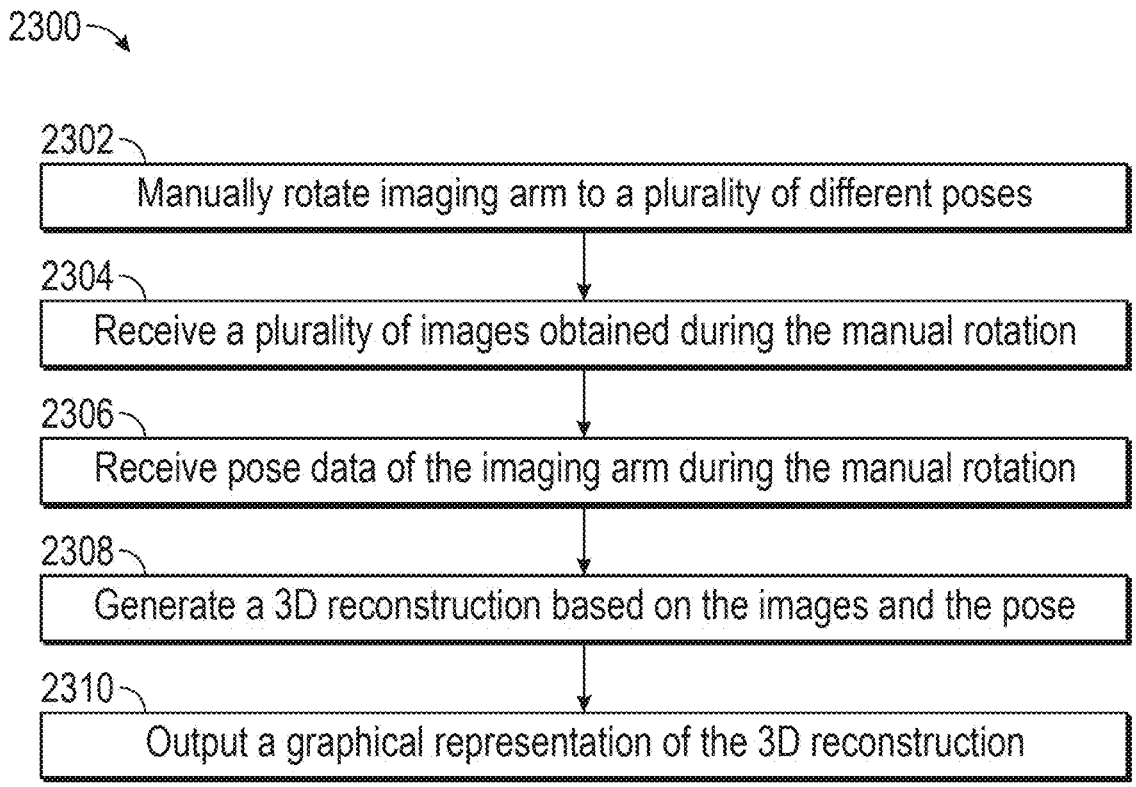
FIG. 23A is a flow diagram illustrating a method for imaging an anatomic region, in accordance with embodiments of the present technology.
Figure 23B:
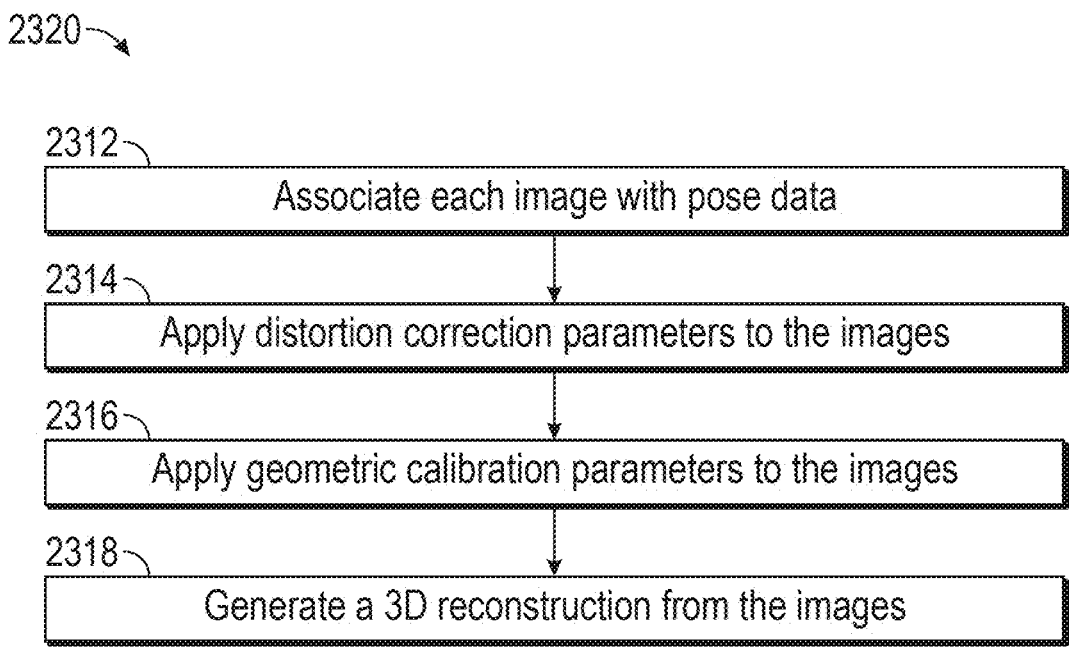
FIG. 23B is a flow diagram illustrating a method for generating a 3D reconstruction, in accordance with embodiments of the present technology.
Figure 24:
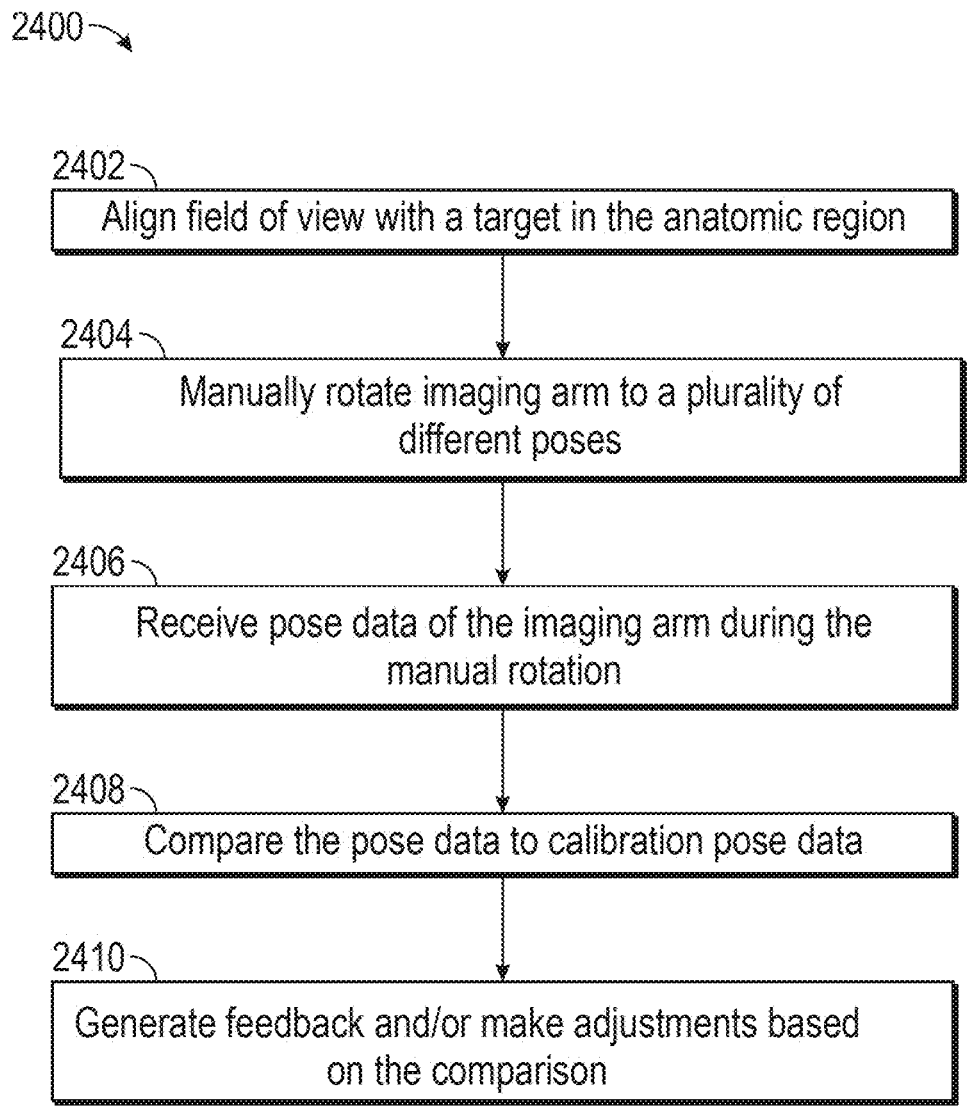
FIG. 24 is a flow diagram illustrating a method of preparing an imaging apparatus for image acquisition, in accordance with embodiments of the present technology.

FIGS. 19-25 illustrate various methods for imaging an anatomic region of a patient with an imaging apparatus such as a mobile C-arm apparatus. Specifically, FIG. 19 provides a general overview of the imaging process, FIGS. 20-22D illustrate methods and devices for calibrating the imaging apparatus, FIGS. 23A and 23B illustrate methods for image acquisition and reconstruction, FIG. 24 illustrates a method for preparing the imaging apparatus for imaging, and FIG. 25A illustrates a method for calibration and imaging using a fiducial marker board. The methods disclosed herein can be performed using any embodiment of the systems and devices described herein, such as the system 100 of FIG. 1A. Any of the methods disclosed herein can be performed by an operator (e.g., a physician, nurse, technician, or other healthcare professional), by a computing device (e.g., the computing device 130 of FIG. 1A), or suitable combinations thereof. For example, some processes in a method can be performed manually by an operator, while other processes in the method can be performed automatically or semi-automatically by one or more processors of a computing device.

FIG. 19 is a flow diagram illustrating a method 1900 for operating an imaging apparatus for mrCBCT imaging, in accordance with embodiments of the present technology. The method 1900 can be performed with a manually-operated imaging apparatus (e.g., a mobile C-arm apparatus) or any other suitable imaging system or device. The method 1900 begins at block 1902 with stabilizing the imaging apparatus. As discussed above, mrCBCT imaging can involve stabilizing the imaging apparatus to reduce or prevent undesirable and/or inconsistent movements (e.g., oscillations, jerks, shifts, flexing, etc.) during manual rotation.

For example, the imaging arm can be stabilized using one or more shim structures, such as any of the embodiments described herein with respect to FIGS. 1A and 3A-10D. Alternatively or in combination, the imaging arm can be rotated by applying force to the support arm (e.g., to the proximal portion of the support arm at or near the center of rotation), rather than by applying force to the imaging arm. As previously described, the force can be applied via one or more lever structures coupled to the support arm, such as any of the embodiments described herein with respect to FIGS. 13A-14E. In other embodiments, however, the imaging arm can be manually rotated without any shim structures and/or without applying force to the support arm.

Alternatively or in combination, the stabilization process of block 1902 can include other processes. For example, block 1902 can also include adjusting the orbital tilt of the imaging arm to improve weight balance and/or ensure the detector surface remains close to tangential to the path of the detector during rotation. Optionally, a motion sensor (e.g., IMU) can be used to provide feedback about the stability of the imaging arm and/or the effectiveness of specific stabilization steps. For example, the feedback can include information characterizing the quality of the stabilization (e.g., are there residual oscillations, should the shims be repositioned), whether the movement trajectory of the imaging arm was satisfactory (e.g., was there significant tilt during the rotation, which may be improved by adjusting the orbital tilt of the C-arm and/or adjusting the shim configuration), and so on. The motion sensor can be attached to any suitable location on the imaging apparatus, such as the detector, radiation source, imaging arm, and/or support arm.

At block 1904, the method 1900 continues with calibrating the imaging apparatus. Calibration can be used to compensate for the variations in the imaging environment and/or mechanical properties of the imaging apparatus that may affect image reconstruction. In some embodiments, calibration includes determining one or more calibration parameters (e.g., distortion correction parameters, geometric calibration parameters) that are used in the subsequent image acquisition and/or image reconstruction processes to adjust for the particular characteristics of the imaging apparatus. Additional details of methods and devices suitable for use in the calibration process of block 1904 are described below with reference to FIGS. 20-22D.

Figure 20:
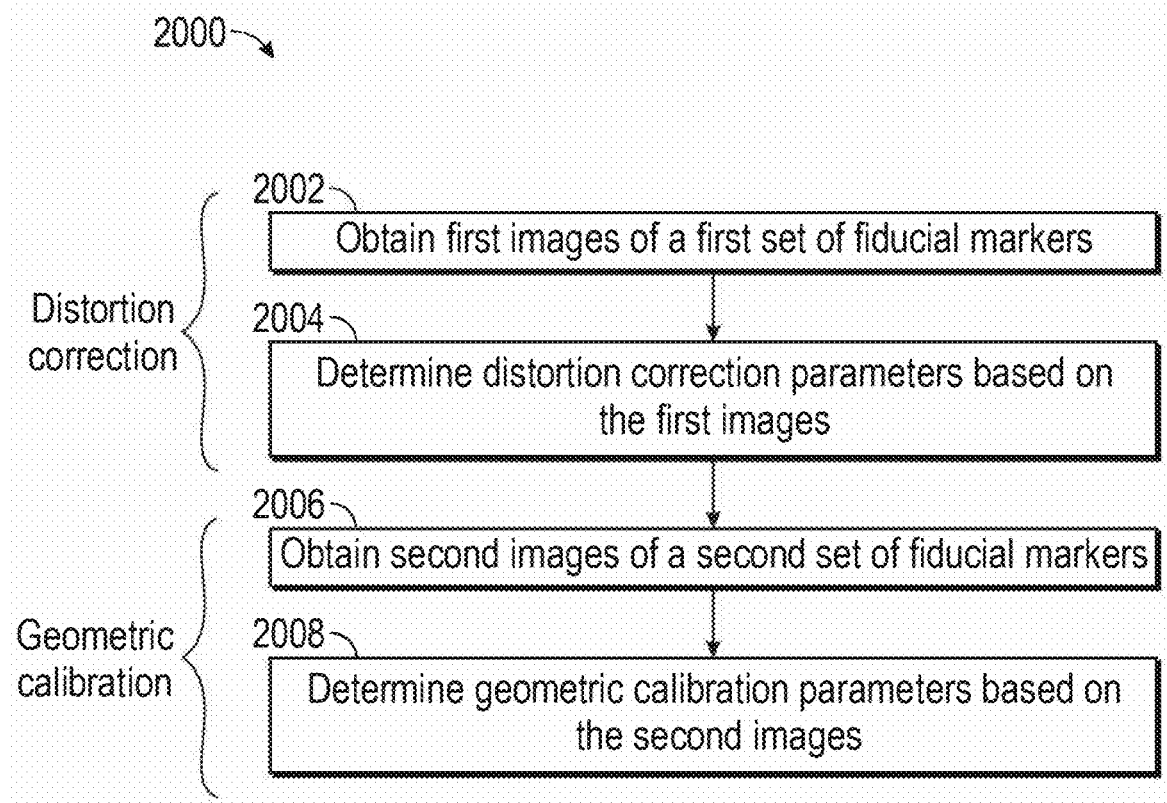
FIG. 20 is a flow diagram illustrating a method for calibrating an imaging apparatus, in accordance with embodiments of the present technology.

FIG. 20 is a flow diagram illustrating a method 2000 for calibrating an imaging apparatus, in accordance with embodiments of the present technology. The method 2000 can be performed as part of the calibration process of block 1904 of the method 1900 of FIG. 19. As shown in FIG. 20, the calibration process can be subdivided into two parts: distortion correction (blocks 2002 and 2004) and geometric calibration (blocks 2006 and 2008).

Distortion correction can be performed in embodiments where one or more components of the imaging apparatus (e.g., the detector) are prone to image distortion that may reduce the accuracy of the subsequent 3D reconstruction. For example, mobile C-arm apparatuses commonly use an image intensifier as the detector, and the images generated by the image intensifier can exhibit pincushion and/or barrel distortion, among others. The distortion can also change depending on the pose (e.g., angle) of the image intensifier. Accordingly, the method 2000 can include performing a distortion correction process to identify the amount of image distortion at various poses of the imaging arm, and determine correction parameters that can be applied to the images to reduce or eliminate distortion. In other embodiments, the distortion correction process can be omitted, e.g., if using a flat panel detector rather than an image intensifier.

At block 2002, the method 2000 can include obtaining one or more first images of a first set of fiducial markers ("first fiducial markers"). The first fiducial markers can be radiodense or radiopaque beads, bearings, etc., that are arranged in a known 2D or 3D geometry, such as a grid, array, pattern, shape, etc. The first fiducial markers can be coupled to the detector in a fixed spatial configuration relative to the detector. The first images can be 2D projection images of the first fiducial markers acquired by the detector as the imaging arm is manually rotated through a plurality of different poses (e.g., rotation angles). Each first image can be associated with a corresponding pose of the imaging arm using any of the devices and techniques described elsewhere herein, such as the embodiments of FIGS. 15-18E.

At block 2004, the method 2000 continues with determining a set of distortion correction parameters based on the first images. The first images can be transmitted to a computing device (e.g., the computing device 130 of FIG. 1A), and the computing device can analyze the first images to detect the locations of the first fiducial markers in the first images (e.g., using image processing and/or computer vision techniques known to those of skill in the art). The computing device can then determine the distortion correction parameters by comparing the locations of the first fiducial markers in the first images to the known, true locations of the first fiducial markers on the grid, array, etc. The distortion correction parameters can represent a set of transformations (e.g., rigid and/or non-rigid transformations such as rotation, translation, deformation, etc.) that would realign the first fiducial markers in the distorted images to their true locations. The distortion correction parameters can be determined through an optimization process according to techniques known to those of skill in the art. This process can be performed for each image to determine the appropriate distortion correction parameters for different poses (e.g., angles) of the imaging arm. The determined distortion correction parameters can then be applied to each image individually to remove distortion artifacts due to the properties of the detector and/or the pose of the detector, as discussed in greater detail below.

Figure 21A:
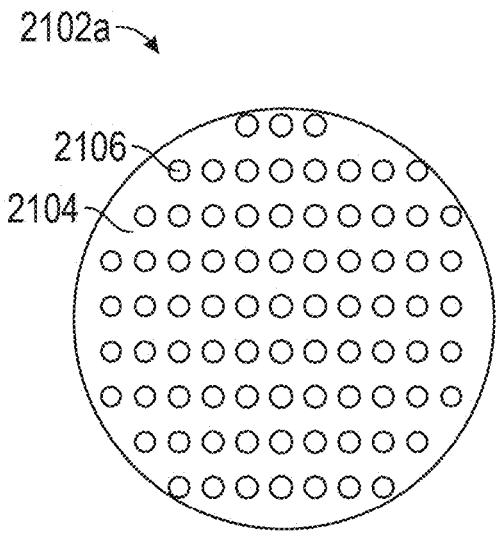
FIGS. 21A-21D illustrate fiducial marker grids for distortion correction in accordance with embodiments of the present technology.

FIG. 21A is a front view of a fiducial marker grid 2102a configured in accordance with embodiments of the present technology. The grid 2102a can be used to determine distortion correction parameters for an imaging apparatus, e.g., as described above with respect to blocks 2002-2004 of FIG. 20. The grid 2102a includes a substrate 2104 containing a plurality of fiducial markers 2106. The substrate 2104 can be made of a radiolucent material, such as acrylonitrile butadiene styrene (ABS), among others. In the illustrated embodiment, the substrate 2104 has a circular shape. In other embodiments, the substrate 2104 can have a different shape, such as square, rectangular, oval, etc. The substrate 2104 can be sized to fit partially or entirely over the surface of a typical detector. For example, the substrate 2104 can have a diameter and/or width within a range from 9 inches to 12 inches.

The markers 2106 can be beads, bearings, flattened disks, etc., made of a radiodense or radiopaque material, such as steel or other metallic material. As shown in FIG. 21A, the markers can be arranged in a regular (e.g., square) grid. In some embodiments, the markers 2106 have a size (e.g., diameter and/or width) within a range from 0.5 mm to 3 mm, and are spaced from each other by a distance of 1 cm. In other embodiments, the size and/or arrangement of the markers 2106 can be varied as desired. The grid 2102a can include any suitable number of discrete markers, such as at least 10, 25, 50, 100, 200, 300, 400, 500, 600, 700, 800, 900, 1000, or more markers.

During use, the grid 2102a can be placed adjacent or near the surface of the detector so that some or all of the markers 2106 are within the field of view of the detector. The grid 2102a can be temporarily coupled to the detector via clips, brackets, clamps, suction cups, velcro straps, rubber bands, magnets, or any other suitable attachment mechanism. Optionally, the grid 2102a and/or detector can include one or more alignment markers so the grid 2102a can be coupled to the detector at a consistent position and/or orientation.

In some embodiments, the grid 2102a is coupled to an attachment device that is connected to the detector. For example, the attachment device 1702a of FIGS. 17A-17E can be used to mount the grid 2102a to the detector. In such embodiments, the attachment device 1702a can be coupled to the detector, and the grid 2102a can be inserted into or otherwise coupled to the frame 1708 of the attachment device 1702a. After the distortion correction process has been completed, the grid 2102a can be removed from the frame 1708 while leaving the attachment device 1702a in place, or the attachment device 1702a and grid 2102a can be removed together.

Optionally, the grid 2102a can include functional components such as a motion sensor (e.g., an IMU) and/or a radiation sensor (e.g., a photodiode). The motion sensor and radiation detector can be used to track the pose of the imaging arm and temporally synchronize the pose data to the acquired images, as discussed above. These components can be embedded in or otherwise coupled to the peripheral portion of the grid 2102a to avoid obscuring the field of view of the detector. In other embodiments, however, the grid 2102a can be provided without the motion sensor and/or the radiation sensor.

Figure 21B:
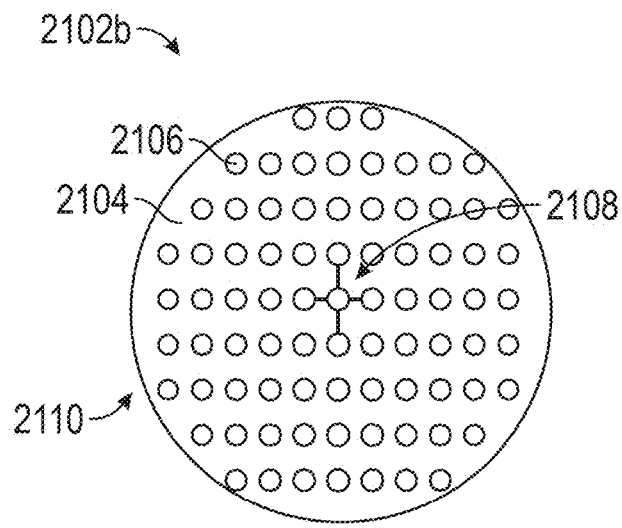
Figure 21C:
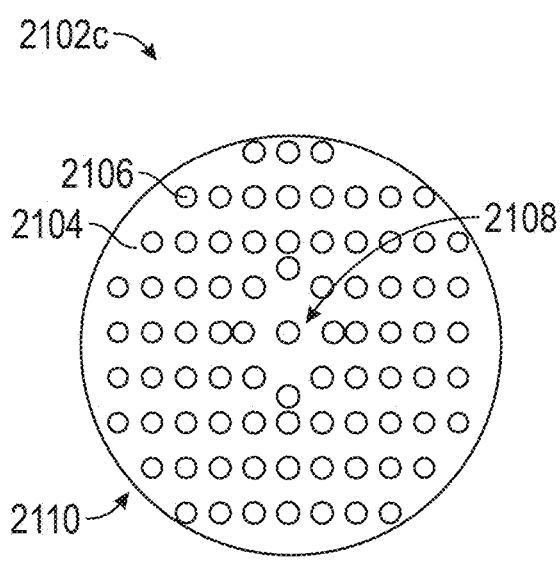
Figure 21D:
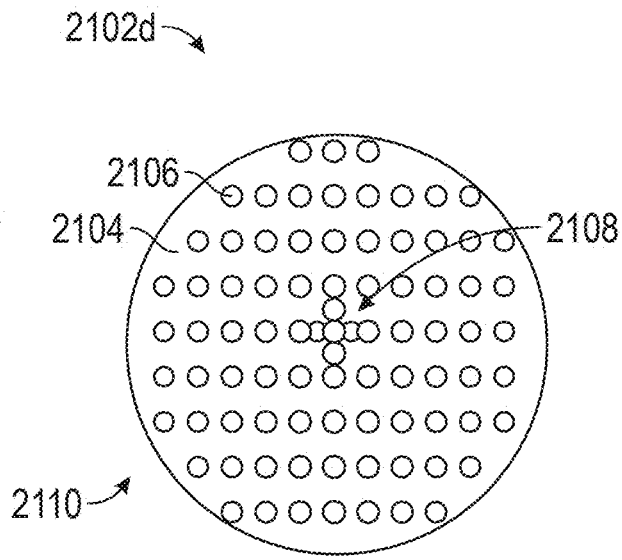

FIGS. 21B-21D are front views of additional fiducial marker grids 2102b-2102d configured in accordance with embodiments of the present technology. The grids 2102b-2102d can be generally similar to the grid 2102a of FIG. 21A. Accordingly, the discussion of the grids 2102b-2102d will be limited to those features that differ from the grid 2102a of FIG. 21A.

Referring first to FIG. 21B, the markers 2106 in the grid 2102b are arranged so that the central portion 2108 has a different pattern than the peripheral portion 2110. This approach can facilitate automated identification of the central portion 2108 of the grid 2102b, which can simplify the optimization process for calculating the distortion correction parameters. In FIG. 21B, for example, the five markers 2106 at the central portion 2108 are connected with radiodense or radiopaque lines to form a cross shape. In FIG. 21C, the central marker 2106 at the central portion 2108 of the grid 2102c is spaced apart from the other markers 2106 by a known radial distance, so that the central portion 2108 has a lower marker density than the peripheral portion 2110. In FIG. 21D, the central portion 2108 of the grid 2102d includes additional markers 2106, so that the central portion 2108 has a higher marker density than the peripheral portion 2110. Alternatively or in combination, other types of patterns, shapes, geometries, etc., can be used to distinguish the central portion 2108 from the peripheral portion 2110.

Referring again to FIG. 20, the geometric calibration process of the method 2000 can include characterizing the geometry of the imaging apparatus during a manual rotation. In some embodiments, geometric calibration is required because of the mechanical instabilities of the imaging apparatus, which can lead to shifting and/or other non-uniform motions during rotation as described above. For example, the manual rotation can cause the imaging arm to deviate from the ideal rotation path (e.g., a single plane, circular rotation path) for CBCT imaging purposes. Additionally, the components of the imaging apparatus may shift during manual rotation, e.g., the internal components of the detector may shift relative to the outer housing. Such internal movements may be difficult or impossible to detect using an externally-placed sensor (e.g., an IMU coupled to the detector housing), and thus may require an image-based calibration process. In some embodiments, the changes in geometry during rotation cause the projection images acquired by the imaging apparatus to be misaligned (e.g., the center of rotation shifts between images), which can detrimentally affect the quality and accuracy of the 3D reconstruction.

Accordingly, the method 2000 can include determining the geometry of the imaging apparatus at various rotational positions in order to determine deviations and/or other movements that may occur during subsequent rotations. Based on the determined geometry, the method 2000 can compute a set of geometric calibration parameters that can be used to adjust the projection images to compensate for the changes in geometry during rotation. For example, the geometric calibration parameters can represent a set of transformations that, when applied to the projection images, corrects any misalignment present in the images due to unwanted movements of the imaging apparatus.

At block 2006, the method 2000 includes obtaining second images of a second set of fiducial markers ("second fiducial markers"). The second fiducial markers can be radiodense or radiopaque beads, bearings, etc., that are positioned within a phantom in a known 3D configuration. The second images can be 2D projection images acquired by the detector as the imaging arm is manually rotated to a plurality of different poses relative to the phantom. In some embodiments, the phantom is positioned at or near the isocenter of the imaging arm, and the imaging arm is manually rotated around the phantom (e.g., in a propeller rotation direction) to obtain the second images of the phantom from a plurality of different rotational angles. Each second image can be associated with a corresponding pose of the imaging arm using any of the devices and techniques described elsewhere herein, such as the embodiments of FIGS. 15-18E. In embodiments where the pose is determined using a fiducial marker board (e.g., the fiducial marker boards 1800-1830 of FIGS. 18A-18E), the phantom can be mounted on or otherwise coupled to the fiducial marker board in a known spatial configuration (e.g., using a stand, at a fixed location on the operating table, etc.).

At block 2008, the method 2000 continues with determining a set of geometric calibration parameters based on the second images. The second images can be transmitted to a computing device (e.g., the computing device 130 of FIG. 1A) for analysis. In some embodiments, the computing device first corrects any image distortion present in the second images using the distortion correction parameters determined in block 2004. The computing device can then analyze the second images to detect the locations of the second fiducial markers in the second images (e.g., using image processing and/or computer vision techniques known to those of skill in the art). Subsequently, the computing device can use the imaged locations of the second fiducial markers and the known 3D configuration of the second fiducial markers in the phantom to determine the geometry of the imaging apparatus during rotation, such as the piercing point, skewness, pitch, roll, tilt, and/or source-to-detector distance, among others. For example, the piercing point can represent the center of rotation of the imaging arm and/or the center of the reference coordinate system in the image data. The geometry of the imaging apparatus can be determined using image-based geometric calibration algorithms known to those of skill in the art.

Subsequently, the geometric calibration parameters can be computed based on the determined geometry of the imaging apparatus. As discussed above, the geometric calibration parameters can represent a set of transformations (e.g., rigid and/or non-rigid transformations such as rotation, translation, deformation, etc.) for adjusting the projection images at each rotational angle of the imaging apparatus to correct any misalignment present. For example, if the piercing point of the imaging apparatus shifts for a particular angle of the imaging arm, the projection image acquired at that angle can be shifted in the opposite direction to realign the piercing point. The determined geometric calibration parameters can be applied to each image individually to realign the images in preparation for image reconstruction, as discussed in greater detail below.

FIG. 22A is a perspective view of a fiducial marker phantom 2202a configured in accordance with embodiments of the present technology. The phantom 2202a can be used to perform geometric calibration for an imaging apparatus, e.g., as described above with respect to blocks 2006-2008 of FIG. 20. The phantom 2202a includes a substrate 2204 containing a plurality of fiducial markers 2206. The substrate 2204 can be made of a radiolucent material (e.g., ABS) and can be manufactured using 3D printing or other suitable techniques. In the illustrated embodiment, the substrate 2204 has an elongated, cylindrical shape. The substrate 2204 can have a length within a range from 7 cm to 25 cm, and a diameter within a range from 7 cm to 25 cm. Optionally, the substrate 2204 can be hollow, with a sidewall thickness within a range from 0.5 cm to 5 cm. In other embodiments, however, the geometry (e.g., size, shape) of the substrate 2204 can be varied as desired, e.g., the substrate 2204 can be rectangular rather than cylindrical, the substrate 2204 can be solid rather than hollow, etc.

The markers 2206 can be beads, bearings, flattened disks, etc., made of a radiodense or radiopaque material, such as steel or other metallic material. The markers 2206 can be embedded in the phantom 2202a at known spatial locations. In the illustrated embodiment, for example, the markers 2206 are arranged in two parallel circles at the first end 2208 and second end 2210 of the substrate 2204. This arrangement can allow the piercing point to be automatically identified in images of the phantom 2202a by connecting diametrically opposed markers 2206 and determining the intersection of the connections, in accordance with techniques known to those of skill in the art. In other embodiments, however, the markers 2206 can be arranged in a different geometry and/or can be positioned at different locations in the substrate 2204 (e.g., between the first and second ends 2208, 2210).

FIG. 22B is a perspective view of another fiducial marker phantom 2202b configured in accordance with embodiments of the present technology. The phantom 2202b can be generally similar to the phantom 2202a of FIG. 22A, except that the phantom 2202b includes a central marker 2212 representing the piercing point of the imaging apparatus. The central marker 2212 can be a bead, bearing, etc., made of a radiodense or radiopaque material, such as copper or another metal. The use of the central marker 2212 can be advantageous because it allows the location of the piercing point to be directly identified in the image data, rather than indirectly calculated from the locations of other markers (e.g., the markers 2206). Although FIG. 22A depicts the phantom 2202b as including the central marker 2212 together with the markers 2206 at the first and second ends 2208, 2210, of the substrate 2204, in other embodiments, the markers 2206 can be omitted such that the central marker 2212 is the only marker within the phantom 2202b.

FIG. 22C is a perspective view of an assembly 2214 that can be used to form the phantom 2202b, in accordance with embodiments of the present technology. The assembly 2214 includes an elongate shaft 2216 (e.g., rod, peg, tube, etc.) carrying the central marker 2212. The elongate shaft 2216 can be formed via additive manufacturing (e.g., 3D printing) with a recess for receiving the central marker 2212, or the central marker 2212 can be deposited or otherwise formed at the appropriate location in the elongate shaft 2216 during the additive manufacturing process.

The elongate shaft 2216 can be connected to a first disk 2218 and a second disk 2220. The first and second disks 2218, 2220 can be located at or near the opposite ends of the elongate shaft 2216. The first and second disks 2218, 2220 can be integrally formed with the elongate shaft 2216 as a single unitary component (e.g., via additive manufacturing). Alternatively, the first and second disks 2218, 2220 can be discrete components that are coupled to the elongate shaft 2216 via fasteners, adhesives, bonding, etc. For example, the first and second disks 2218, 2220 can each include a central hole, and the ends of the elongate shaft 2216 can fit into the holes to form the assembly 2214.

Referring to FIGS. 22B and 22C together, to assemble the phantom 2202b, the elongate shaft 2216 can be positioned into the hollow interior cavity of the substrate 2204. The elongate shaft 2216 can have a length identical or similar to the length of the substrate 2204 so that the elongate shaft 2216 extends from the first end 2208 of the substrate 2204 to the second end 2210 of the substrate 2204. In embodiments where the first and second disks 2218, 2220 are separable from the elongate shaft 2216, the first and second disks 2218, 2220 can then be positioned over the first and second ends 2208, 2210 of the substrate 2204, respectively, and connected to the elongate shaft 2216. The first and second disks 2218, 2220 can be sized to partially or fully cover the first and second ends 2208, 2210 of the substrate 2204. For example, the first and second disks 2218, 2220 can each have a diameter identical or similar to the diameter of the first and second ends 2208, 2210, respectively. Optionally, the first and second disks 2218, 2220 can be attached to the substrate 2204 using fasteners (e.g., snaps), adhesives (e.g., tape), or any other suitable technique to ensure that the central marker 2212 is positioned at the center of the phantom 2202b.

FIG. 22D is a perspective view of a fiducial marker phantom 2202c configured in accordance with embodiments of the present technology. The phantom 2202c can be generally similar to the phantom 2202b of FIG. 22A, except that the phantom 2202b includes rings 2222 rather than individual markers at the first and second ends 2208, 2210 of the substrate 2204. In certain situations, continuous structures such as rings 2222 may be easier to identify in projection images than discrete markers, which can improve the accuracy of the calibration process. The rings 2222 can be made of a radiodense or radiopaque (e.g., metallic) material. The rings 2222 can have a diameter identical or similar to the diameter of the substrate 2204, and can have a thickness within a range from 1 mm to 5 mm. The rings 2222 can be formed in many different ways. For example, the rings 2222 can be discrete components that are coupled to the substrate 2204 to form the phantom 2202c. In such embodiments, the first and second ends 2208, 2210 of the substrate 2204 can include grooves for receiving the rings 2222. Alternatively, the rings 2222 can be integrally formed with the substrate 2204, such as by using an additive manufacturing process in which material is deposited into the substrate 2204 at the appropriate locations.

Referring again to FIG. 20, the various steps of the method 2000 can be performed at different times before and/or during an imaging procedure. For example, the distortion correction process of blocks 2002 and 2004 can be performed before an imaging apparatus is used for mrCBCT imaging for the first time. The distortion correction parameters determined in block 2004 can be reused for subsequent mrCBCT procedures performed using the same imaging apparatus, such that the distortion correction process does not need to be performed again. For example, the distortion correction parameters can be interpolated or extrapolated to subsequent images, e.g., using an IMU or other sensor to correlate the stored distortion correction parameters at a certain angle of rotation to a similar angle in the subsequent images. In other embodiments, however, the distortion correction process can be performed periodically for the same imaging apparatus (e.g., once every week, month, six months, year, etc.), performed when there are significant changes in the imaging setup (e.g., if the detector is replaced, if the imaging apparatus is moved to a different environment), or can even be performed each time the imaging apparatus is used. Alternatively, in embodiments where little or no image distortion is observed (e.g., when a flat panel detector is used), the distortion correction process of blocks 2002 and 2004 can be omitted entirely.

Similarly, the geometric calibration process of blocks 2006 and 2008 can be performed before an imaging apparatus is used for mrCBCT imaging for the first time, e.g., after performing distortion correction for the imaging apparatus. The geometric calibration parameters determined in block 2008 can be reused for subsequent mrCBCT procedures performed using the same imaging apparatus, such that the geometric calibration process does not need to be performed again. In other embodiments, however, the geometric calibration process can be performed periodically for the same imaging apparatus (e.g., once every week, month, six months, year, etc.), performed when there are significant changes in the imaging setup, or can even be performed each time the imaging apparatus is used (e.g., once before a medical procedure is performed). Optionally, the geometric calibration process of blocks 2006 and 2008 may be omitted entirely.

Referring again to FIG. 19, at block 1906, the method 1900 continues with acquiring images and generating a 3D reconstruction from the images. As described elsewhere herein, the process of block 1906 can be used to perform intraprocedural mrCBCT imaging of a target in the patient anatomy using a manually-operated imaging apparatus that lacks any motors, actuators, etc., for automatically rotating the imaging arm. A representative example of an image acquisition and reconstruction method that can be performed as part of the imaging process of block 1906 is described below with reference to FIGS. 21A and 21B.

FIG. 23A is a block diagram illustrating a method 2300 for imaging an anatomic region, in accordance with embodiments of the present technology. Some or all of the steps of the method 2300 can be performed as part of the image acquisition and reconstruction process of block 1906 of the method 1900 of FIG. 19. The method 2300 begins at block 2302 with manually rotating an imaging arm to a plurality of different poses. As previously described, the imaging arm can be part of an imaging apparatus, such as the imaging apparatus 104 of FIG. 1A. For example, the imaging apparatus can be a mobile C-arm apparatus, and the imaging arm can be the C-arm of the mobile C-arm apparatus. The imaging arm can be rotated around a target anatomic region of a patient along any suitable direction, such as a propeller rotation direction. In some embodiments, the imaging arm is manually rotated to a plurality of different poses (e.g., angles) relative to the target anatomic region. The imaging arm can be rotated through an arc that is sufficiently large for performing CBCT imaging. For example, the arc can be at least 90°, 100°, 110°, 120°, 130°, 140°, 150°, 160°, 170°, 180°, 190°, 200°, 210°, 220°, 230°, 240°, 250°, 260°, 270°, 280°, 290°, 300°, 310°, 320°, 330°, 340°, 350°, or 360°.

At block 2304, the method 2300 continues with receiving a plurality of images obtained during the manual rotation. The images can be 2D projection images generated by a detector (e.g., an image intensifier or flat panel detector) carried by the imaging arm. The method 2300 can include generating any suitable number of images, such as at least 50, 100, 200, 300, 400, 500, 600, 700, 800, 900, or 1000 images. The images can be generated at a rate of at least 5 images per second, 10 images per second, 20 images per second, 30 images per second, 40 images per second, 50 images per second, or 60 images per second. In some embodiments, the images are generated while the imaging arm is manually rotated through the plurality of different poses, such that some or all of the images are obtained at different poses of the imaging arm.

At block 2306, the method 2300 can include receiving pose data of the imaging arm during the manual rotation. The pose data can be generated using any of the techniques and devices described herein. For example, the pose data can be generated based on sensor data from at least one sensor, such as an IMU or another motion sensor coupled to the imaging arm (e.g., to the detector), to the support arm, or a combination thereof. The sensor data can be processed to determine the pose of the imaging arm at various times during the manual rotation. As previously discussed, the pose of the imaging arm can be estimated without using a fiducial marker board or other reference object positioned near the patient. In other embodiments, however, the pose data can be determined using a fiducial marker board, such as the embodiments described above with reference to FIGS. 18A-18E. In such embodiments, the fiducial marker board can be positioned on the operating table at a known spatial configuration relative to the imaging apparatus (e.g., the same spatial configuration used during calibration).

Optionally, the pose data of block 2306 can also be used to provide feedback to the user on the speed, smoothness, and/or other characteristics of the manual rotation. For example, if the imaging arm is being rotated too slowly (e.g., if the estimated total rotation time would take longer than 30 seconds and/or would exceed an automatic shut-off time for the imaging apparatus), then the computing device could output an alert (e.g., an image, text, sound, etc.) instructing the user to increase the rotation speed. Conversely, if the imaging arm is being rotated too quickly, the alert could instruct the user to slow down. As another example, the computing device could display a target speed value or range for image acquisition, as well as the actual speed of the imaging arm. The target speed value or range can be based on a predetermined total rotation time for improved image quality, such as a rotation time within a range from 1 second to 20 seconds. In some embodiments, a graphical representation of the rotation speed is displayed to give the operator real-time feedback during the rotation, e.g., to increase, decrease, or maintain the current rotation speed. For example, the representation can show a first indicator when the rotation is at an appropriate speed, a second indicator (e.g. a red indicator) when the speed is too fast, a third indicator (e.g., a green indicator) when the speed is too slow, etc.

At block 2308, the method 2300 includes generating a 3D reconstruction based on the images received in block 2304 and the pose data received in block 2306. The 3D reconstruction process can include inputting the images into an image reconstruction algorithm, such as a filtered backprojection algorithm, iterative reconstruction algorithm, or other suitable algorithm known to those of skill in the art. Optionally, the images can be processed before being input into the algorithm, e.g., by applying calibration parameters to remove distortion artifacts, correct misalignment, and/or other adjustments to prepare the images for reconstruction. A representative example of method for generating a 3D reconstruction is discussed below in connection with FIG. 23B.

FIG. 23B is a flow diagram illustrating a method 2320 for generating a 3D reconstruction from a plurality of images, in accordance with embodiments of the present technology. Some or all of the processes of the method 2320 can be performed as part of block 2308 of the method 2300 of FIG. 23A. The method 2320 begins at block 2312 with associating each image with pose data. As discussed above, the pose data can be temporally synchronized with the projection images generated by the imaging apparatus, such that each image is associated with a corresponding pose (e.g., rotational angle) of the imaging arm at or near the time the image was obtained.

At block 2314, the method 2320 can include applying one or more distortion correction parameters to some or all of the images. As discussed above, the distortion correction parameters can be applied to the images in order to reduce or eliminate distortion present in the images, e.g., due to use of an image intensifier. The distortion correction parameters can be parameters that were determined in a previous calibration process (e.g., the process of block 2004 of FIG. 20). In some embodiments, the distortion correction parameters are stored as a lookup table (or similar data structure) that records a set of parameters for each angle of the imaging arm. Accordingly, to correct distortion in a particular image, the angle of the imaging arm at the time of image acquisition ("target angle") can be determined using any of the techniques described herein. The stored distortion correction parameters corresponding to the target angle can then be retrieved from the lookup table. If the target angle does not match any of the entries in the lookup table, the distortion correction parameters can be interpolated or extrapolated from other parameters, e.g., the stored distortion correction parameters for the angle(s) closest to the target angle.

At block 2316, the method 2320 can include applying one or more geometric calibration parameters to some or all of the images. As discussed above, the geometric correction parameters can be applied to the images in order to correct any misalignments present in the images, e.g., due to motions of the imaging arm that deviate from a single plane, isocentric trajectory. The distortion correction parameters can be parameters that were determined in a previous calibration process (e.g., the process of block 2008 of FIG. 20). In some embodiments, the geometric calibration parameters are stored as a lookup table (or similar data structure) that records a set of parameters for each angle of the imaging arm. Accordingly, when adjusting a particular image, the angle of the imaging arm at the time of image acquisition ("target angle") can be determined using any of the techniques described herein. The stored geometric calibration parameters corresponding to the target angle can then be retrieved from the lookup table. If the target angle does not match any of the entries in the lookup table, the geometric calibration parameters can be interpolated or extrapolated from other parameters, e.g., the stored geometric calibration for the angle(s) closest to the target angle. The geometric calibration parameters can therefore be used to correct the images in situations where it is not feasible to use a fiducial marker phantom or other physical calibration reference.

In some embodiments, the distortion correction parameters of block 2314 and/or the geometric calibration parameters of block 2316 are adjusted based on the pose data of the imaging arm. These adjustments can be made to account for any deviations from the calibration setup. For example, the actual rotation trajectory of the imaging arm during patient imaging ("imaging trajectory") can differ from the rotation trajectory of the imaging apparatus when determining the calibration parameters for the imaging apparatus as discussed with respect to FIG. 20 ("calibration trajectory"). If the imaging trajectory deviates significantly from the calibration trajectory, the original parameters may no longer be sufficient for correcting image distortion and/or image misalignment.

Accordingly, the method 2320 can further including detecting whether the imaging trajectory deviates significantly from the calibration trajectory, e.g., with respect to tilt, pitch, roll, or any other suitable measurement value. A deviation can be considered significant, for example, if the magnitude of the difference in the value in the calibration trajectory and the value in the imaging trajectory is at least 5%, 10%, 15%, 20%, 25%, or 50% of the value in the calibration trajectory. The deviations can be detected by comparing the pose data of the imaging apparatus during the imaging trajectory (e.g., the pose data of block 2306 of FIG. 23A) to the pose data of the imaging apparatus during the calibration trajectory (e.g., the pose data determined during the method 2000 of FIG. 20).

If significant deviations are detected, the method 2320 can include updating or otherwise modifying the distortion correction parameters and/or geometric calibration parameters to account for these deviations. The updates can be made to the distortion correction parameters only, to the geometric calibration parameters only, or to both sets of parameters. The updates can be determined based on the pose data of the imaging arm and the known geometry of the imaging apparatus, in accordance with techniques known to those of skill in the art. For example, if the imaging arm exhibited a forward tilt of 1.5° at the 90° angular position in the calibration trajectory, but exhibited a forward tilt of 2.0° at the 90° angular position in the imaging trajectory, the geometric calibration parameters for the image(s) obtained at or near the 90° angular position can be updated to compensate for the difference in the forward tilt. The updated geometric calibration parameters can be computed by determining how the detected deviation affects the geometry of the imaging apparatus (e.g., with respect to piercing point, skewness, pitch, roll, tilt, and/or source-to-detector distance), determining the amount and/or direction of additional image misalignment produced by the change in geometry, and then determining the parameters that would correct the additional misalignment.

At block 2318, the method 2320 can continue with generating a 3D reconstruction from the images, in accordance with techniques known to those of skill in the art. For example, the 3D reconstruction can be generated using filtered backprojection, iterative reconstruction, and/or other suitable algorithms. Optionally, image interpolation can also be applied to the reconstruction process to reduce image noise arising from a reduced number of image acquisition angles, if appropriate.

The method 2320 of FIG. 23B can be modified in many different ways, if desired. For example, in other embodiments, block 2314 can be omitted, e.g., if the imaging apparatus uses a flat panel detector or otherwise is not expected to produce much image distortion. As another example, block 2316 can be omitted, if the images are not expected to be significantly misaligned. Additionally, the method 2320 can include other image preprocessing steps not shown in FIG. 23B.

Referring again to FIG. 23A, at block 2310, the method 2300 can optionally include outputting a graphical representation of the 3D reconstruction. The graphical representation can be displayed on an output device (e.g., the display 132 and/or secondary display 134 of FIG. 1A) to provide guidance to a user in performing a medical procedure. In some embodiments, the graphical representation includes the 3D reconstruction generated in block 2308, e.g., presented as a 3D model or other virtual rendering. Alternatively or in combination, the graphical representation can include 2D images derived from the 3D reconstruction (e.g., 2D axial, coronal, and/or sagittal slices).

In some embodiments, the user views the graphical representation to confirm whether a medical tool is positioned at a target location. For example, the graphical representation can be used to verify whether a biopsy instrument is positioned within a nodule or lesion of interest. As another example, the graphical representation can be used to determine whether an ablation device is positioned at or near the tissue to be ablated. If the tool is positioned properly, the user can proceed with performing the medical procedure. If the graphical representation indicates that the tool is not at the target location, the user can reposition the tool, and then repeat some or all of the steps of the method 2300 to generate a new 3D reconstruction of the tool and/or target within the anatomy.

Referring again to FIG. 19, the method 1900 can optionally include additional processes not shown in FIG. 19. For example, once the calibration process of block 1904 has been completed, the method 1900 can optionally include performing a pre-acquisition rotation of the imaging arm. The pre-acquisition rotation can serve as a "practice" rotation in order to provide feedback to the user on the trajectory and quality of the manual rotation. The feedback can be used to adjust the stabilization, trajectory, speed, quality, and/or other aspects of the manual rotation and/or imaging apparatus setup. In some embodiments, some or all of the processes related to the pre-acquisition rotation are performed without any radiation to reduce the patient's radiation exposure. A representative example of a method that can be performed as part of a pre-acquisition process is described below with reference to FIG. 24.

FIG. 24 is a flow diagram illustrating a method 2400 of preparing an imaging apparatus for image acquisition, in accordance with embodiments of the present technology. The method 2400 can be performed before the image acquisition and reconstruction process of block 1906 of FIG. 19. The method 2400 can begin at block 2402, with aligning the field of view of the imaging apparatus with a target in the anatomic region. In some embodiments, the field of view in the 3D reconstruction is significantly smaller than the field of view in the projection images. Accordingly, the alignment process of block 2402 can be performed to ensure that the target site will be visible in the final CBCT images. In some embodiments, the alignment process is performed after the imaging apparatus has been stabilized and/or calibrated. In other embodiments, however, the alignment process of block 2402 is optional and may be omitted.

In some embodiments, the alignment process of block 2402 includes obtaining one or more test images of the patient anatomy, such as a lateral and/or frontal projection image. The computing device can then process the test images to identify the image locations that would be present in the image reconstruction. For example, the computing device can overlay an indicator (e.g., a circle or other shape, shading, arrows) onto the test images that represents the smaller field of view of the image reconstruction. As another example, the computing device can crop or otherwise remove portions of the test images to remove locations that would not be visible in the image reconstruction. Accordingly, the user can view the processed test images to determine whether the target will be visible in the image reconstruction. If the target will not be visible, the operator can adjust the positioning of the imaging apparatus and/or patient, and can acquire new test images.

At block 2404, the method can continue with manually rotating the imaging arm of the imaging apparatus to a plurality of different poses. The manual rotation can be performed under conditions identical or similar to the conditions during which the actual image acquisition will take place. For example, the imaging apparatus can already be stabilized, calibrated, and/or aligned as discussed above. The user can rotate the imaging arm along the rotational trajectory that will be used to generate the actual images, such as a propeller rotation over a range of at least 90°, 100°, 110°, 120°, 130°, 140°, 150°, 160°, 170°, 180°, 190°, 200°, 210°, 220°, 230°, 240°, 250°, 260°, 270°, 280°, 290°, 300°, 310°, 320°, 330°, 340°, 350°, or 360°.

At block 2406, the method 2400 continues with receiving pose data of the imaging arm during the manual rotation of block 2404. The pose data can be generated using any of the devices and techniques described herein. For example, the pose of the imaging arm can be determined using a motion sensor coupled to the imaging arm. The pose data can be transmitted to a suitable computing device (e.g., the computing device 130 of FIG. 1A) for storage and processing.

At block 2408, the method 2400 can include comparing the pose data of block 2406 to calibration pose data. The calibration pose data can include pose data of the imaging arm during a manual rotation performed as part of a previous calibration process (e.g., the geometric calibration process of FIG. 20). The calibration pose data can indicate the trajectory and/or speed of the imaging arm during the previous calibration rotation. In some embodiments, the characteristics of the manual rotation performed by the user during the actual image acquisition should be as close as possible to the characteristics of the calibration rotation to improve the quality of the image reconstruction. Accordingly, in block 2408, the computing device can analyze the pose data to determine whether the pre-acquisition rotation deviates significantly from the calibration rotation with respect to trajectory, speed, stabilization (e.g., absence of oscillations, shifts, or other unwanted motions), etc.

At block 2410, the method 2400 can include generating feedback and/or making adjustments to the imaging apparatus, based on the comparison performed in block 2408. For example, the computing device can provide feedback to the user about how the pre-acquisition rotation deviates from the calibration rotation. The computing device can also provide recommendations on how to adjust the rotation and/or imaging apparatus to more closely conform to the calibration rotation or otherwise improve the operation of the imaging apparatus. For example, if the imaging apparatus was not as well stabilized in the pre-acquisition rotation compared to the calibration rotation, the user can adjust the stabilization techniques used to improve stability, e.g., by adding more shim structures, changing the types and/or locations of the shim structures, altering where force is applied during the rotation, or any of the other approaches described herein. As another example, if the imaging arm is tilted or otherwise positioned in a way that differs from the positioning in the calibration rotation, the computing device can recommend that the user adjust the imaging arm accordingly. In yet another example, the feedback can also indicate whether the pre-acquisition rotation was sufficiently smooth, uniform (e.g., circular), and/or at the appropriate speed for image acquisition purposes.

In some embodiments, the computing device can output a graphical user interface to guide the operator in making the appropriate adjustments. For example, the interface can show a virtual representation of the imaging apparatus with indicators (e.g., arrows) displaying the recommended adjustments. Alternatively or in combination, the interface can output textual instructions describing the adjustments to the imaging apparatus and/or rotational trajectory to be made. In some embodiments, the interface displays real-time feedback, such as the actual position and/or orientation of the imaging arm (e.g., from IMU and/or other sensor data) as the user makes adjustments so the user can see whether the targeted position and/or orientation has been reached. Optionally, the interface can also output alerts, warnings, or other feedback during the manual rotation (e.g., "rotation is too fast," "imaging arm is too far to the left") so the user can adjust the rotation trajectory and/or speed in real-time.

The method 2400 of FIG. 24 can be modified in many different ways, if desired. For example, some or all of the processes of the method 2400 can be performed multiple times, e.g., to ensure that the user is performing the manual rotation appropriately and/or that the imaging apparatus is properly set up for acquiring images of the target. In some embodiments, some or all of the processes of blocks 2404, 2406, 2408, and/or 2410 are repeated until the pre-acquisition rotation is sufficiently close to the calibration rotation. As another example, the process of acquiring and reviewing test images in block 2402 can be repeated until the user confirms that the target is properly aligned for image reconstruction purposes. Moreover, some or all of the processes of the method 2400 can be omitted, such as the processes of blocks 2402 and/or 2410.

Referring again to FIG. 19, the method 1900 can be modified in many different ways. For example, the processes of the method 1900 can be performed in a different order. In some embodiments, stabilization may not be necessary to accurately determine the calibration parameters and/or to perform the pre-acquisition rotation. Accordingly, the stabilization process of block 1902 can be performed after the calibration process of block 1904. Moreover, some of the processes of the method 1900 can be optional. For example, any of the processes of blocks 1902 and/or 1904 can be omitted from the method 1900.

Figure 25A:
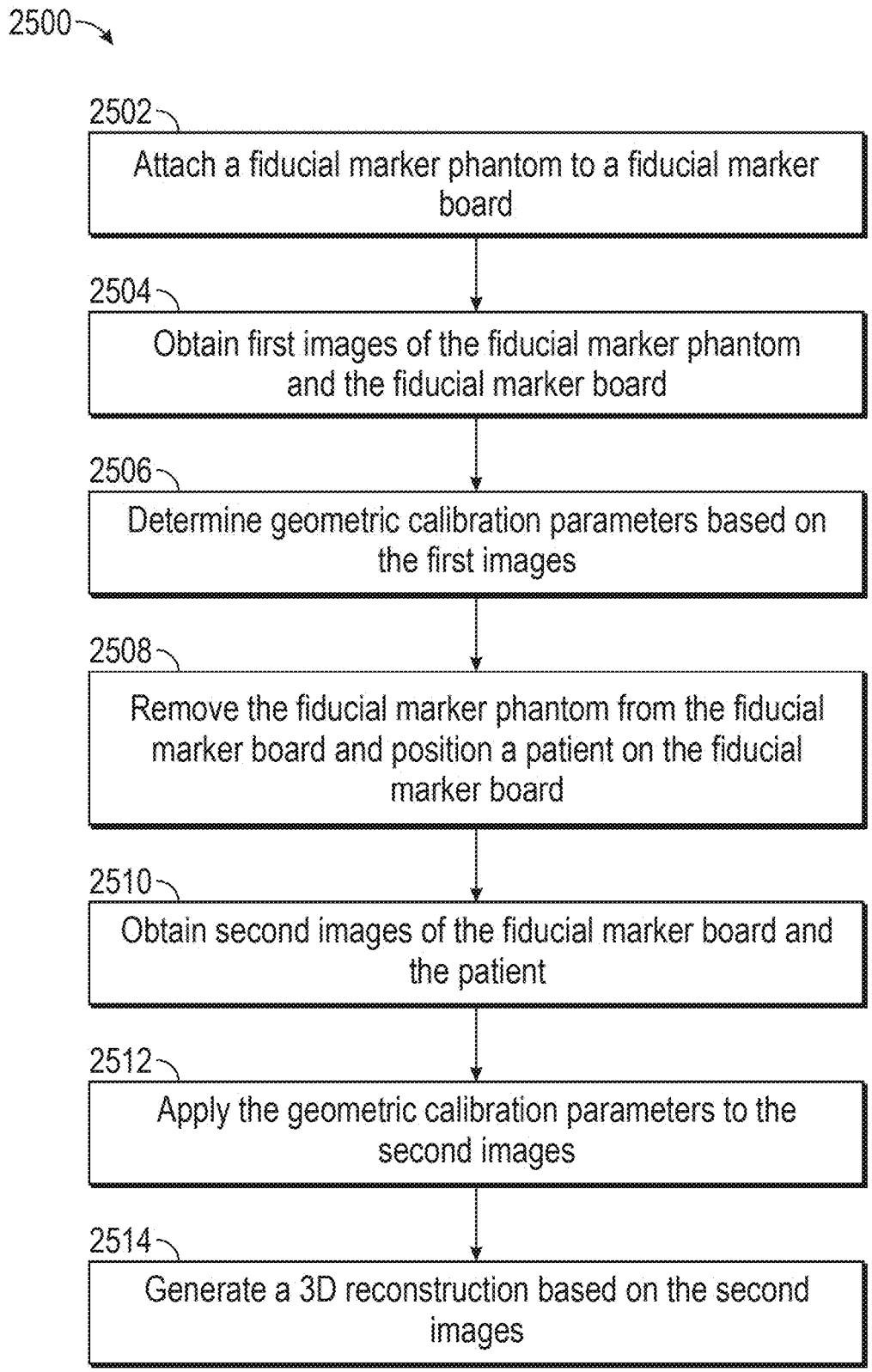
FIG. 25A is a flow diagram illustrating a method for calibration and image acquisition using a fiducial marker board in accordance with embodiments of the present technology.

FIG. 25A is a flow diagram illustrating a method 2500 for calibration and image acquisition using a fiducial marker board, in accordance with embodiments of the present technology. The method 2500 can be generally similar to the method 1900 of FIG. 19, except that a fiducial marker board is used to estimate the pose (e.g., rotational angle) of the imaging arm during geometric calibration and image acquisition.

The method 2500 begins at block 2502 with attaching a fiducial marker phantom to a fiducial marker board. The fiducial marker phantom can be any of the embodiments described with respect to FIGS. 22A-22D, and the fiducial marker board can be any of the embodiments described with respect to FIGS. 18A-18G.

At block 2504, the method 2500 can include obtaining a set of first images of the fiducial marker phantom and fiducial marker board. The first images can be 2D projection images acquired by the detector as the imaging arm is manually rotated through a plurality of different poses (e.g., rotation angles), as described elsewhere herein. Each first image can be associated with a corresponding pose of the imaging arm. The pose of the imaging arm can be determined from the markers of the fiducial marker board in the first images, as described above with respect to FIGS. 18A-18G.

At block 2506, the method 2500 continues with determining a set of geometric calibration parameters based on the first images. The geometric calibration parameters can be determined by identifying the locations of the fiducial markers of the phantom in the first images, as discussed above with respect to block 2006 of the method 2000 of FIG. 20. In some embodiments, the combination of the phantom with the fiducial marker board allows the geometry of the imaging apparatus (e.g., piercing point, skewness, pitch, roll, tilt, source-to-detector distance) to be fully determined.

At block 2508, the method 2500 can include removing the fiducial marker phantom from the fiducial marker board and positioning a patient on the fiducial marker board. For example, the patient can be placed in a supine position with their back resting on the board.

At block 2510, the method 2500 continues with obtaining a set of second images of the fiducial marker board and the patient. The second images can be 2D projection images acquired by the detector as the imaging arm is manually rotated through a plurality of different poses (e.g., rotation angles), as described elsewhere herein. Each second image can be associated with a corresponding pose of the imaging arm. The pose of the imaging arm can be determined from the markers of the fiducial marker board in the second images, as described above with respect to FIGS. 18A-18G.

At block 2512, the method 2500 can include applying the geometric calibration parameters to some or all of the second images. The process of block 2512 can be identical or similar to the process of block 2316 of the method 2320 of FIG. 23B. For example, in some embodiments, the geometric calibration parameters of block 2306 are retrieved from a lookup table (or similar data structure) based on the pose (e.g., rotational angle) of the imaging arm, as determined using the fiducial marker board. Because the same fiducial marker board is used for both geometric calibration and image acquisition, the pose estimates generated from the fiducial marker board are consistent across these processes and can therefore be used to determine the appropriate geometric calibration parameters to be applied to each second image.

At block 2514, the method 2500 can include generating a 3D reconstruction based on the second images. The 3D reconstruction can be produced from the second images using any of the techniques described elsewhere herein. Optionally, before the 3D reconstruction is generated, the markers of the fiducial marker board and/or any imaging artifacts produced by the markers can be subtracted from the second images. The subtraction can be performed using computer vision techniques and/or other image processing algorithms known to those of skill in the art.

FIG. 25B is a flow diagram illustrating a method for operating an imaging apparatus, in accordance with embodiments of the present technology. At block 2502', the method 2500' can include positioning a phantom (e.g., a calibration phantom and/or cylinder) near the imaging apparatus. For example, the phantom can be positioned near an axis of rotation of an imaging arm of the imaging apparatus. At block 2504', the method can include obtaining first 2D images using a shim-stabilized imaging arm at multiple angles. At block 2506', the method 2500' can include obtaining pose data of the imaging arm based on the first images that include the phantom. In some embodiments, a general model of the pose of the imaging arm can be created for any arbitrary projection angle. At block 2508', the method 2500' can include removing the phantom from the center of rotation and place a fiducial marker board around a patient area of interest. In some embodiments, the fiducial marker board is an L- or J-shaped fiducial marker board. In other embodiments, the fiducial marker board is not an L- or J-shaped fiducial marker board. At block 2510', the method 2500' can include obtaining second 2D images of both the fiducial marker board and the patient during a rotation of the imaging arm at multiple angles. At block 2512', the method 2500' can include obtaining second pose data of the imaging arm based on the second images. For example, the method 2500' can include estimating an imaging arm angle for each of the second images using the known geometric arrangement of the fiducial marker board. The method 2500' can include using the angle estimation from the fiducial marker board to reference the general calibration model generated from the first images to determine the imaging arm pose and other relevant geometric information for each of the second images. The method 2500' can include removing the signal of the fiducial markers in the fiducial marker board. At block 2514', the method 2500' can include generating a 3D reconstruction of the image volume using the second images with the estimated pose information determined using the angle estimation from the fiducial marker board.

In some embodiments of the present technology, a specialized fiducial board, such as an L- or J-shaped fiducial marker board or other fiducial marker board, can be used in conjunction with a phantom (e.g., a calibration phantom and/or cylinder) to perform manually rotated 3D reconstructions. In such embodiments, the phantom can be configured to determine the pose of the imaging arm using methods known to those skilled in the art. In some embodiments of the methods herein, the phantom can be placed near the center of the imaging arm axis of rotation and a first series of 2D images is acquired using a shim-stabilized imaging arm at multiple angles. The pose of the imaging arm at each image angle can be determined from the corresponding 2D image by tracking and/or segmenting the fiducial markers in the phantom as known to those skilled in the art. Once the pose of the imaging arm at each image is determined, a general model of the pose of the imaging arm can be created for any arbitrary projection angle using interpolation/extrapolation techniques known to those of skill in the art.

Subsequently, the phantom is removed and a patient area of interest (e.g., a chest) can be placed near the imaging arm (such as the isocenter of a C-arm). A fiducial marker board, such as an L- or J-shaped fiducial marker board can be placed around the patient near the area of interest. The fiducial marker board has an arrangement of radiodense ball bearings or other markers from which the angular position of the imaging arm can be determined using methods known to those skilled in the art. A second series of 2D images of both the fiducial marker board and the patient can then be obtained during a rotation of the imaging arm at multiple angles. The fiducial markers in the board can then be automatically tracked and segmented using their known pattern. The encoding of the fiducial pattern index allows for estimation of the imaging arm angle for each 2D projection image during the second series of images. Once the angle is estimated for each image of the second series of images, the estimated angle can be used to reference the general calibration model (e.g., a lookup table, etc.) generated from the first series of images. The angle determined from each image in the second series of images is thus used to determine the correct pose and other relevant geometric information of the C-arm as modeled from the first series of images. Once the pose of the C-arm is determined, then the signals of the fiducial markers in the board can be virtually (digitally) removed or suppressed from each projection image using techniques known to those of skill in the art (e.g. interpolation of pixel neighbors) to limit or prevent metal artifacts within the reconstructed 3D images of the patient. Once the signal from the fiducial markers is removed, a 3D reconstruction can be performed.

Figure 26A:
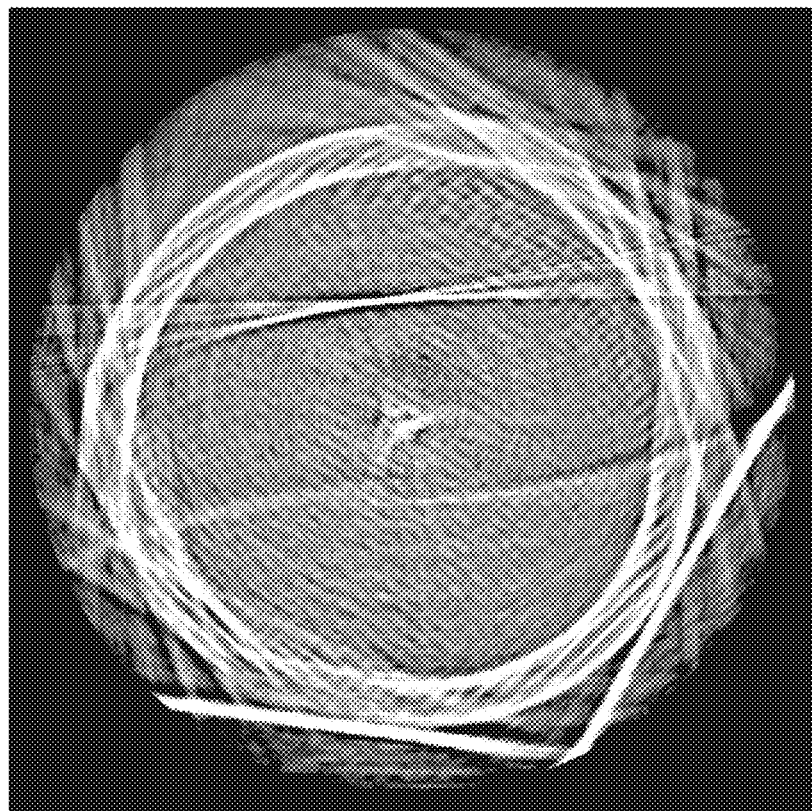
FIG. 26A is a CBCT image of a phantom generated by a manually-operated imaging apparatus without calibration or shim stabilization.
Figure 26B:
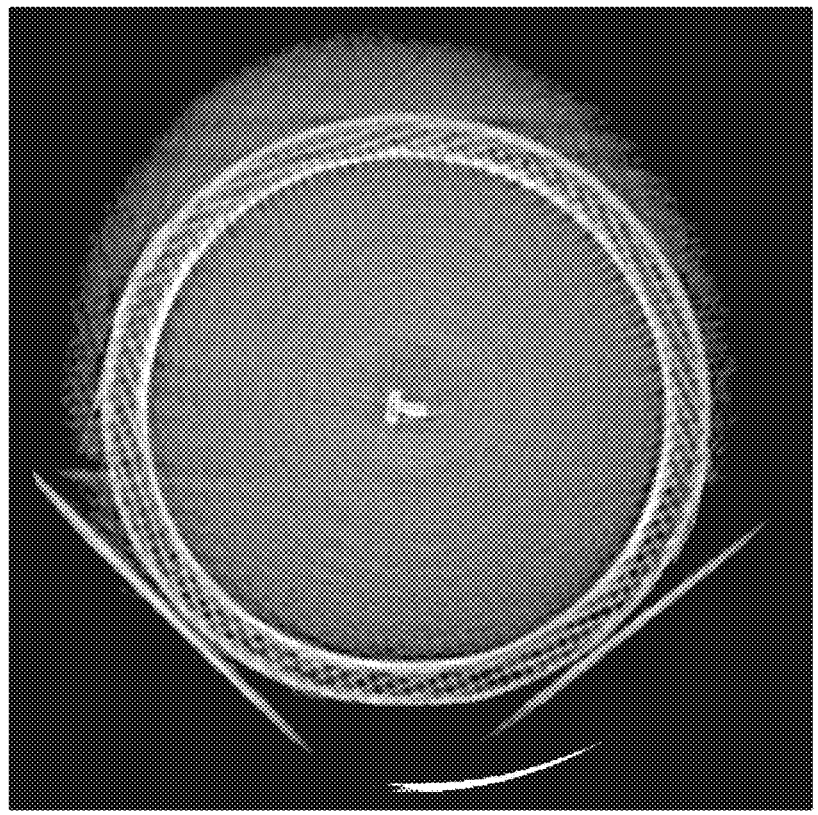
FIG. 26B is a CBCT image of a phantom generated by a manually-operated imaging apparatus with calibration and shim stabilization, in accordance with embodiments of the present technology.

FIGS. 26A and 26B are representative CBCT images of a phantom generated using a manually-rotated mobile C-arm apparatus. The images were acquired using a GE Healthcare OEC 9900 C-arm apparatus with an image intensifier and a rotation angle of approximately 180 degrees. The phantom was a cylindrical phantom including a set of rings and a central marker, similar to the phantom 2202c of FIG. 22D. The images are cross-section views of the phantom showing the outer edge of the cylinder and the shaft carrying the central marker (the central marker is not shown in the images). The image in FIG. 26A was generated without using calibration or shim stabilization, while the image in FIG. 26B was generated with calibration and shim stabilization, in accordance with embodiments of the present technology. As shown in FIG. 26A, in the absence of calibration and shim stabilization, the image is blurry, misaligned, and includes significant distortion artifacts. In contrast, after calibration and shim stabilization, the image of FIG. 26B accurately and clearly depicts the geometry of the phantom.

Figure 27A:
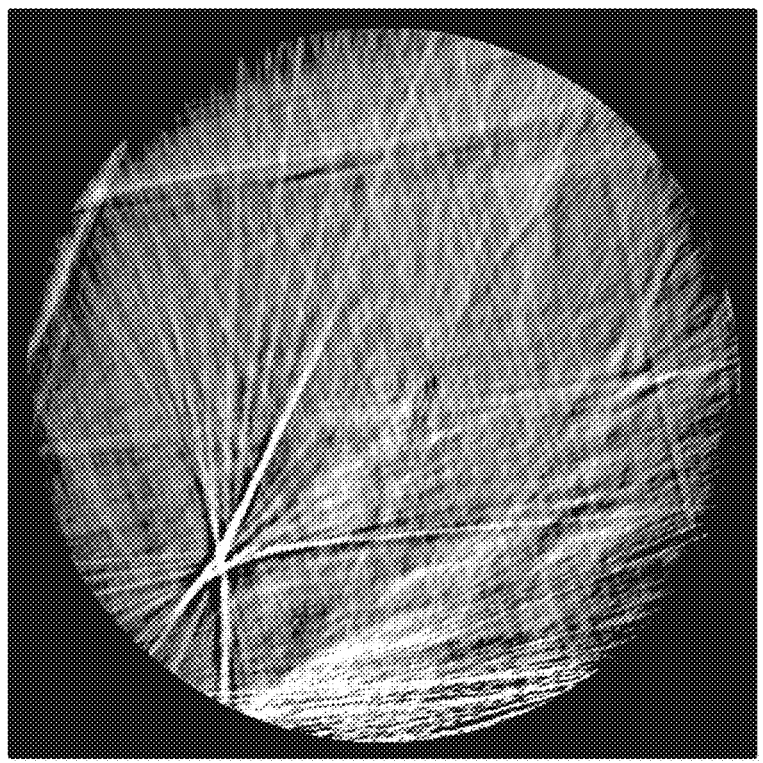
FIG. 27A is a CBCT image of a lung generated by a manually-operated imaging apparatus without calibration or shim stabilization.
Figure 27B:
FIG. 27B is a CBCT image of a lung generated by a manually-operated imaging apparatus with calibration and shim stabilization, in accordance with embodiments of the present technology.

FIGS. 27A and 27B are representative CBCT images of a lung generated using a manually-rotated mobile C-arm apparatus. The images were acquired using a GE Healthcare OEC 9900 C-arm apparatus with an image intensifier and a rotation angle of approximately 180°, and show a live porcine chest with an implanted pulmonary nodule 2702. The image in FIG. 27A was generated without using calibration or shim stabilization, while the image in FIG. 27B was generated with calibration and shim stabilization, in accordance with embodiments of the present technology. As shown in FIG. 27A, without calibration and shim stabilization, the anatomic structures are not visible in the resulting image. As shown in FIG. 27B, with calibration and shim stabilization, the resulting image has sufficiently high spatial resolution and contrast-to-noise ratio to clearly depict the anatomic structures within and near the lung, such as the nodule 2702 blood vessel 2704, bronchi 2706, and rib 2708.

Figure 27C:
FIG. 27C is a CBCT image of a lung generated with a robotically-operated CBCT imaging system.

FIG. 27C is a CBCT image generated using a robotically-rotated CBCT imaging system. Specifically, the image was acquired using a Siemens Artis Zeego CBCT system, a stationary system with a motorized imaging arm, with a rotation angle of approximately 220°. The image shows the same porcine chest as the images of FIGS. 27A and 27B. As can be seen by comparing FIGS. 27B and 27C, the imaging techniques described herein can produce image reconstructions using a manually-operated C-arm apparatus that are comparable in quality to image reconstructions produced by high-end, specialized CBCT systems.

EXAMPLES

The following examples are included to further describe some aspects of the present technology, and should not be used to limit the scope of the technology.

1. A method for imaging an anatomic region, the method comprising:
receiving, from a detector carried by an imaging arm of an x-ray imaging apparatus, a plurality of two-dimensional (2D) images of the anatomic region, wherein the 2D images are obtained during manual rotation of the imaging arm, and wherein the imaging arm is stabilized by a shim structure during the manual rotation;
receiving, from at least one sensor coupled to the imaging arm, sensor data indicative of a plurality of poses of the imaging arm during the manual rotation; and
generating, based on the 2D images and the sensor data, a 3D representation of the anatomic region.
2. The method of Example 1, wherein the x-ray imaging apparatus comprises a mobile C-arm apparatus.
3. The method of Example 1 or 2, wherein the detector comprises an image intensifier.
4. The method of any one of Examples 1 to 3, wherein the x-ray imaging apparatus comprises a support arm slidably coupled to the imaging arm, and the shim structure is positioned at an interface between the imaging arm and the support arm.
5. The method of Example 4, wherein the shim structure is configured to reduce movement of the imaging arm relative to the support arm.
6. The method of Example 4 or 5, wherein the support arm is rotatably coupled to a movable base, and the support arm and the imaging arm are manually rotated relative to the movable base to obtain the 2D images.
7. The method of Example 6, wherein the manual rotation is actuated by a force applied at or near an interface between the support arm and the movable base.
8. The method of Example 7, wherein the force is applied to a lever structure coupled at or near the interface between the support arm and the movable base.
9. The method of any one of Examples 4 to 8, wherein the shim structure comprises at least one elongate member configured to fit at least partially in the interface between the imaging arm and the support arm.
10. The method of Example 9, wherein the shim structure includes:
a set of elongate members positioned at two sides of the interface between the imaging arm and the support arm, and a bridge region connecting the set of elongate members.
11. The method of any one of Examples 1 to 10, wherein the manual rotation comprises a propeller rotation.
12. The method of any one of Examples 1 to 11, wherein the manual rotation comprises a rotation of at least 90 degrees.
13. The method of Example 12, wherein the manual rotation comprises a rotation of at least 180 degrees.
14. The method of any one of Examples 1 to 13, wherein the at least one sensor comprises a motion sensor and the sensor data comprises motion data of the imaging arm.
15. The method of Example 14, wherein the motion sensor comprises an inertial measurement unit (IMU).
16. The method of Example 14 or 15, further comprising determining the plurality of poses of the imaging arm based on the motion data.
17. The method of any one of Examples 1 to 16, wherein the at least one sensor includes a sensor coupled to the detector.
18. The method of any one of Examples 1 to 17, wherein generating the 3D representation comprises associating each 2D image with a corresponding pose of the imaging arm.
19. The method of Example 18, wherein associating each 2D image with the corresponding pose comprises identifying a pose of the imaging arm when the 2D image was obtained.
20 The method of any one of Examples 1 to 19, further comprising applying one or more distortion correction parameters to at least some of the 2D images before generating the 3D representation.
21. The method of any one of Examples 1 to 20, further comprising applying one or more geometric calibration parameters to at least some of the 2D images before generating the 3D representation.
22. The method of any one of Examples 1 to 21, further comprising outputting real-time feedback to an operator during the manual rotation for adjusting a rotation speed of the imaging arm.
23 The method of any one of Examples 1 to 22, further comprising outputting the 3D representation on a graphical user interface during a medical procedure performed in the anatomic region.
24. A system for imaging an anatomic region, the system comprising:
a shim structure configured to stabilize manual rotation of an imaging arm of an x-ray imaging apparatus;
at least one sensor configured to generate sensor data indicative of a pose of the imaging arm;
one or more processors operably coupled to the x-ray imaging apparatus and the at least one sensor; and
a memory operably coupled to the one or more processors and storing instructions that, when executed by the one or more processors, cause the system to perform operations comprising:
receiving, from the x-ray imaging apparatus, a sequence of two-dimensional (2D) images of the anatomic region obtained during the manual rotation of the imaging arm;
determining, based on the sensor data, pose information of the imaging arm during the manual rotation of the imaging arm; and
generating, based on the 2D images and the pose information, a 3D reconstruction of the anatomic region.
25. The system of Example 24, wherein the x-ray imaging apparatus comprises a mobile C-arm apparatus.
26. The system of Example 24 or 25, wherein the x-ray imaging apparatus comprises a support arm slidably coupled to the imaging arm, and the shim structure is configured to be positioned at an interface between the imaging arm and the support arm.
27. The system of Example 26, wherein the shim structure is configured to reduce movement of the imaging arm relative to the support arm.
28. The system of Example 27, wherein the shim structure inhibits orbital rotation of the imaging arm.
29 The system of any one of Examples 26 to 28, wherein the support arm is rotatably coupled to a movable base, and the support arm and the imaging arm are manually rotated relative to the movable base to obtain the 2D images.

30. The system of Example 29, further comprising a lever structure coupled at or near an interface between the support arm and the movable base, wherein the lever structure is configured to facilitate the manual rotation of the imaging arm.

31. The system of any one of Examples 26 to 30, wherein the shim structure comprises at least one elongate member configured to fit at least partially in the interface between the imaging arm and the support arm.

32 The system of Example 31, wherein the shim structure includes a pair of arm regions positioned at two sides of the interface between the imaging arm and the support arm.

33 The system of Example 32, wherein the shim structure includes a bridge region connecting the pair of arm regions.

34 The system of any one of Examples 24 to 33, wherein the manual rotation comprises an angular rotation.

35. The system of any one of Examples 24 to 34, wherein the manual rotation comprises a rotation of at least 90 degrees.

36. The system of any one of Examples 24 to 35, wherein the at least one sensor comprises a motion sensor and the sensor data comprises motion data of the imaging arm.

37. The system of Example 36, wherein the motion sensor comprises an inertial measurement unit (IMU).

38. The system of Example 36 or 37, wherein the motion sensor is coupled to the detector.

39 The system of Example 38, wherein the motion sensor is coupled to the detector via an attachment device.

40. The system of Example 39, wherein the attachment device comprises a clip, bracket, frame, or container.

41 The system of any one of Examples 24 to 40, further comprising a controller operably coupled to the at least one sensor, wherein the controller is configured to temporally synchronize the 2D images to the sensor data generated by the at least one sensor.

42. The system of any one of Examples 24 to 41, further comprising a radiation sensor configured to generate a signal in response to detected radiation, wherein the signal is transmitted to the controller to temporally synchronize the 2D images to the sensor data.

43. The system of any one of Examples 24 to 42, further comprising a display configured to output a graphical representation of the 3D reconstruction.

44. A non-transitory computer-readable medium comprising instructions that, when executed by one or more processors of a computing system, cause the computing system to perform operations comprising:

receiving, from a detector carried by an imaging arm of a mobile C-arm apparatus, a plurality of projection images of an anatomic target, wherein the projection images are obtained during manual rotation of the imaging arm, and wherein the imaging arm is stabilized by a shim structure during the manual rotation;

receiving, from at least one sensor coupled to the imaging arm, pose data of the imaging arm during the manual rotation; and generating, based on the projection images and the pose data, a 3D reconstruction of the anatomic target.

45. A method for imaging an anatomic region, the method comprising:

receiving, from a detector carried by an imaging arm of an x-ray imaging apparatus, a plurality of two-dimensional (2D) images of the anatomic region, wherein the 2D images are obtained during manual rotation of the imaging arm, and wherein the imaging arm is stabilized by a shim structure during the manual rotation;

receiving pose data of the imaging arm during the manual rotation; and generating, based on the 2D images and the pose data, a 3D representation of the anatomic region.

46 The method of Example 45, wherein the pose data is generated from images of a fiducial marker board positioned near the anatomic target.

47. The method of Example 46, wherein the fiducial marker board includes a plurality of fiducial markers and at least some of the fiducial markers are located in different planes.

48. The method of Example 46 or 47, wherein the fiducial marker board includes a base region and at least one sidewall extending upward from the base region.

49 The method of any one of Examples 45 to 48, wherein the pose data is generated by at least one sensor coupled to the imaging arm.

50. A method for operating an imaging apparatus, the method comprising:

receiving, from a detector carried by an imaging arm of the imaging apparatus, a plurality of first images of a set of first fiducial markers, wherein the first images are obtained during manual rotation of the imaging arm;

determining a set of distortion correction parameters for the imaging apparatus based on the first images;

receiving, from the detector, a plurality of second images of a set of second fiducial markers, wherein the second images are obtained during manual rotation of the imaging arm; and determining a set of geometric calibration parameters for the imaging apparatus based on the second images.

51. The method of Example 50, wherein the imaging apparatus is a mobile C-arm apparatus.

52. The method of Example 50 or 51, wherein the first and second images are each obtained during a propeller rotation of the imaging arm.

53 The method of any one of Examples 50 to 52, wherein the detector comprises an image intensifier.

54. The method of any one of Examples 50 to 53, wherein the first fiducial markers are arranged in a grid.

55. The method of any one of Examples 50 to 54, further comprising determining, using at least one sensor carried by the imaging arm, pose data of the imaging arm associated with the first images, wherein the distortion correction parameters are determined based on the pose data.

56. The method of any one of Examples 50 to 55, wherein the second fiducial markers are disposed within a phantom.

57. The method of any one of Examples 50 to 56, further comprising adjusting at least some of the second images using the set of distortion correction parameters.

58. The method of any one of Examples 50 to 57, further comprising determining, using at least one sensor carried by the imaging arm, pose data of the imaging arm associated with the second images, wherein the geometric calibration parameters are determined based on the pose data.

59. The method of Example 58, further comprising processing the second images to determine one or more of the following: piercing point, skewness, pitch, roll, tilt, or source-to-detector distance of the imaging apparatus.

60. The method of Example 58 or 59, further comprising:
receiving, from at least one sensor coupled to the imaging arm, second pose data of the imaging arm during a pre-acquisition manual rotation;
comparing the second pose data to the pose data associated with the second images; and
outputting feedback to a user based on the comparison.

61. The method of Example 60, wherein the feedback comprises feedback regarding one or more of the following: rotation trajectory, rotation speed, orientation of the imaging arm, position of the imaging arm, or stability of the imaging arm.

62. The method of any one of Examples 50 to 61, further comprising:
receiving, from the detector, a plurality of third images of an anatomic region of a patient, wherein the third images are obtained during manual rotation of the imaging arm, and wherein the imaging arm is stabilized by a shim structure during the manual rotation;
receiving, from at least one sensor coupled to the imaging arm, pose data of the imaging arm associated with the third images; and
generating a volumetric reconstruction of the anatomic region based on the third images and the pose data.

63. The method of Example 62, further comprising:
applying the distortion correction parameters to the third images; and
applying the geometric calibration parameters to the third images.

64 The method of Example 63, further comprising updating one or more of the distortion correction parameters or the geometric calibration parameters based on data from the at least one sensor, before generating the volumetric reconstruction.

65. A system for imaging an anatomic region, the system comprising:
one or more processors; and
a memory operably coupled to the one or more processors and storing instructions that, when executed by the one or more processors, cause the system to perform operations comprising:
receiving, from a detector carried by an imaging arm of an x-ray imaging apparatus, a plurality of first images of a fiducial marker grid, wherein the first images are obtained during manual rotation of the imaging arm;
determining a set of distortion correction parameters for the imaging apparatus based on the first images;
receiving, from the detector, a plurality of second images of a fiducial marker phantom, wherein the second images are obtained during manual rotation of the imaging arm; and
determining a set of geometric calibration parameters for the imaging apparatus based on the second images.

66. The system of Example 65, wherein the x-ray imaging apparatus is a mobile C-arm apparatus.

67. The system of Example 65 or 66, wherein the first and second images are each obtained during a propeller rotation of the imaging arm.

68. The system of any one of Examples 65 to 67, wherein the detector comprises an image intensifier.

69. The system of any one of Examples 65 to 68, further comprising the fiducial marker grid.

70. The system of Example 69, wherein the fiducial marker grid includes a central portion and a peripheral portion, the central portion having a different pattern than the peripheral portion.

71. The system of any one of Examples 65 to 70, further comprising an attachment device for mounting the fiducial marker grid to the detector.

72. The system of Example 71, further comprising a motion sensor, wherein the attachment device is configured to couple the motion sensor to the detector.

73 The system of any one of Examples 65 to 72, wherein the operations further comprise determining, using the motion sensor, pose data of the imaging arm associated with the first images, wherein the distortion correction parameters are determined based on the pose data.

74. The system of any one of Examples 65 to 73, further comprising the fiducial marker phantom.

75. The system of Example 74, wherein the fiducial marker phantom includes at least one second fiducial marker at a central portion of the phantom.

76. The system of Example 74 or 75, wherein the phantom includes:
a first ring at a first end of the phantom; and
a second ring at a second end of the phantom opposite the first end.

77. The system of any one of Examples 65 to 76, wherein the operations further comprise adjusting at least some of the second images using the set of distortion correction parameters.

78. The system of any one of Examples 65 to 77, further comprising a motion sensor coupled to the detector.

79 The system of Example 78, wherein the operations further comprise determining, using the motion sensor, pose data of the imaging arm associated with the second images, wherein the geometric calibration parameters are determined based on the pose data.

80. The system of Example 79, wherein the operations further comprise:
receiving, from the motion sensor, second pose data of the imaging arm during a pre-acquisition manual rotation; and
comparing the second pose data to the pose data associated with the second images.

81. The system of Example 80, further comprising a display configured to output feedback to a user based on the comparison of the second pose data to the pose data, wherein the feedback comprises feedback regarding one or more of the following: rotation trajectory, rotation speed, orientation of the imaging arm, position of the imaging arm, or stability of the imaging arm.

82. The system of any one of Examples 65 to 81, wherein the operations further comprise:
receiving, from the detector, a plurality of third images of an anatomic region of a patient, wherein the third images are obtained during manual rotation of the imaging arm, and wherein the imaging arm is stabilized by a shim structure during the manual rotation;
receiving, from a motion sensor coupled to the detector, pose data of the imaging arm associated with the third images;
adjusting the third images using the distortion correction parameters;
adjusting the third images using the geometric calibration parameters; and
generating a volumetric reconstruction of the anatomic region based on the third images and the pose data.

83. A non-transitory computer-readable medium comprising instructions that, when executed by one or more processors of a computing system, cause the computing system to perform operations comprising:

receiving, from a detector carried by an imaging arm of an imaging apparatus, a plurality of first images of a set of first fiducial markers, wherein the first images are obtained during manual rotation of the imaging arm;

determining a set of distortion correction parameters for the imaging apparatus based on the first images;

receiving, from the detector, a plurality of second images of a set of second fiducial markers, wherein the second images are obtained during manual rotation of the imaging arm; and determining a set of geometric calibration parameters for the imaging apparatus based on the second images.

84. A method for imaging an anatomic region, the method comprising:

receiving, from a detector carried by an imaging arm of a mobile C-arm apparatus, a plurality of 2D images of the anatomic region, wherein the 2D images are obtained during manual rotation of the imaging arm, and wherein the imaging arm is stabilized by a shim structure during the manual rotation;

receiving data indicative of a plurality of poses of the imaging arm during the manual rotation; and generating, based on the 2D images and the data, a 3D reconstruction of the anatomic region.

85. The method of Example 84, wherein the mobile C-arm apparatus comprises a support arm slidably coupled to the imaging arm, and the shim structure is positioned at an interface between the imaging arm and the support arm.

86. The method of Example 85, wherein the shim structure is configured to reduce movement of the imaging arm relative to the support arm.

87. The method of Example 84 or Example 85, wherein the shim structure is configured to fit at least partially in the interface between the imaging arm and the support arm.

88. The method of Example 87, wherein the shim structure includes:

a pair of arm regions configured to be positioned at two sides of the interface between the imaging arm and the support arm, and a bridge region connecting the set of elongate members.

89. The method of Example 85, wherein the support arm is rotatably coupled to a movable base, and the support arm and the imaging arm are manually rotated relative to the movable base to obtain the 2D images.

90. The method of Example 89, wherein the manual rotation is actuated by a force applied to a lever structure coupled at or near an interface between the support arm and the movable base.

91. The method of any one of Examples 84 to 90, wherein the manual rotation comprises a propeller rotation.

92. The method of any one of Examples 84 to 91, wherein the manual rotation comprises a rotation of at least 90 degrees.

93. The method of any one of Examples 84 to 91, wherein the data indicative of the plurality of poses of the imaging arm are received from a motion sensor coupled to the imaging arm.

94. The method of Example 93, wherein the motion sensor comprises an inertial measurement unit.

95 The method of any one of Examples 84 to 94, wherein the plurality of 2D images includes a fiducial board, and wherein the data indicative of the plurality of poses of the imaging arm are generated from the 2D images.

96. The method of any one of Examples 84 to 95, further comprising associating each 2D image with a corresponding pose of the imaging arm at a time when the 2D image was obtained.

97. The method of any one of Examples 84 to 96, wherein the 3D reconstruction comprises a cone-beam computed tomography reconstruction.

98 The method of any one of Examples 84 to 97, further comprising applying one or more distortion correction parameters to at least some of the 2D images before generating the 3D reconstruction.

99 The method of any one of Examples 84 to 98, further comprising applying one or more geometric calibration parameters to at least some of the 2D images before generating the 3D reconstruction.

100. The method of any one of Examples 84 to 99, wherein generating the 3D reconstruction is based on pose data previously acquired using the imaging arm.

101. A method for imaging an anatomic region, the method comprising:

receiving, from a detector carried by an imaging arm of an x-ray imaging apparatus, a plurality of 2D images of an anatomic region, wherein the 2D images are obtained during manual rotation of the imaging arm, and wherein the imaging arm is coupled to a shim structure during the manual rotation;

receiving pose data of the imaging arm during the manual rotation; and generating, based on the 2D images and the pose data, a 3D representation of the anatomic region.

102. The method of Example 101, wherein the x-ray imaging apparatus is a mobile C-arm apparatus.

103. The method of Example 101 or Example 102, wherein the manual rotation comprises a propeller rotation of at least 180 degrees.

104. The method of any one of Examples 101 to 103, wherein the shim structure inhibits orbital rotation of the imaging arm.

105. The method of any one of Examples 101 to 104, wherein the x-ray imaging apparatus comprises a support arm coupled to the imaging arm, and the shim structure is configured to inhibit movement of the imaging arm relative to the support arm.

106. The method of Example 105, wherein the shim structure is configured to fill at least one gap in an interface between the support arm and the imaging arm.

107. The method of Example 106, wherein the shim structure comprises at least one elongate member configured to be positioned within the at least one gap.

108. The method of any one of Examples 101 to 107, wherein the pose data is received from at least one sensor associated with the x-ray imaging apparatus, and wherein the at least one sensor comprises a motion sensor coupled to the imaging arm.

109. The method of any one of Examples 101 to 108, further comprising temporally synchronizing the 2D images to the pose data.

110. The method of any one of Examples 101 to 109, wherein temporally synchronizing the 2D images to the pose data comprises identifying a pose of the imaging arm at a time when each 2D image was obtained.

111. The method of Example 110, wherein the pose comprises a rotation angle of the imaging arm.

112. The method of any one of Examples 101 to 111, wherein the pose data is second pose data and generating the 3D reconstruction is based on first pose data previously acquired using the imaging arm.

113. A method for imaging an anatomic region, the method comprising:
- receiving, from a detector carried by an imaging arm of a mobile C-arm apparatus, a plurality of 2D projection images of the anatomic region, wherein the 2D projection images are obtained during manual rotation of the imaging arm, and wherein the imaging arm is mechanically stabilized by a shim structure during the manual rotation;
- determining a plurality of rotation angles of the imaging arm during the manual rotation, wherein each rotation angle is associated with a corresponding 2D projection image;
- generating, based on the 2D projection images and the associated rotation angles, a 3D reconstruction of the anatomic region; and
- outputting the 3D reconstruction on a graphical user interface configured to provide guidance during a medical procedure performed in the anatomic region.

CONCLUSION

Although many of the embodiments are described above with respect to systems, devices, and methods for performing a medical procedure in a patient's lungs, the technology is applicable to other applications and/or other approaches, such as medical procedures performed in other anatomic regions (e.g., the musculoskeletal system). Moreover, other embodiments in addition to those described herein are within the scope of the technology. Additionally, several other embodiments of the technology can have different configurations, components, or procedures than those described herein. A person of ordinary skill in the art, therefore, will accordingly understand that the technology can have other embodiments with additional elements, or the technology can have other embodiments without several of the features shown and described above with reference to FIGS. 1A-27C.

The various processes described herein can be partially or fully implemented using program code including instructions executable by one or more processors of a computing system for implementing specific logical functions or steps in the process. The program code can be stored on any type of computer-readable medium, such as a storage device including a disk or hard drive. Computer-readable media containing code, or portions of code, can include any appropriate media known in the art, such as non-transitory computer-readable storage media. Computer-readable media can include volatile and non-volatile, removable and non-removable media implemented in any method or technology for storage and/or transmission of information, including, but not limited to, random-access memory (RAM), read-only memory (ROM), electrically erasable programmable read-only memory (EEPROM), flash memory, or other memory technology; compact disc read-only memory (CD-ROM), digital video disc (DVD), or other optical storage; magnetic cassettes, magnetic tape, magnetic disk storage, or other magnetic storage devices; solid state drives (SSD) or other solid state storage devices; or any other medium which can be used to store the desired information and which can be accessed by a system device.

The descriptions of embodiments of the technology are not intended to be exhaustive or to limit the technology to the precise form disclosed above. Where the context permits, singular or plural terms may also include the plural or singular term, respectively. Although specific embodiments of, and examples for, the technology are described above for illustrative purposes, various equivalent modifications are possible within the scope of the technology, as those skilled in the relevant art will recognize. For example, while steps are presented in a given order, alternative embodiments may perform steps in a different order. The various embodiments described herein may also be combined to provide further embodiments.

As used herein, the terms "generally," "substantially," "about," and similar terms are used as terms of approximation and not as terms of degree, and are intended to account for the inherent variations in measured or calculated values that would be recognized by those of ordinary skill in the art.

Moreover, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Additionally, the term "comprising" is used throughout to mean including at least the recited feature(s) such that any greater number of the same feature and/or additional types of other features are not precluded. As used herein, the phrase "and/or" as in "A and/or B" refers to A alone, B alone, and A and B.

To the extent any materials incorporated herein by reference conflict with the present disclosure, the present disclosure controls.

It will also be appreciated that specific embodiments have been described herein for purposes of illustration, but that various modifications may be made without deviating from the technology. Further, while advantages associated with certain embodiments of the technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein.

We claim:

1. A method for operating a mobile C-arm apparatus, the method comprising:
- receiving, from a detector carried by an imaging arm of the mobile C-arm apparatus, a plurality of first images of a set of fiducial markers, wherein the first images are obtained during manual rotation of the imaging arm, wherein the mobile C-arm apparatus comprises a support arm movably coupled to the imaging arm, and wherein movement of the imaging arm relative to the support arm is constrained by a stabilization mechanism during the manual rotation; and
- determining a set of geometric calibration parameters for the mobile C-arm apparatus based on the first images, wherein the geometric calibration parameters are configured for generating a 3D reconstruction of an anatomic region of a patient based on a plurality of second images of the anatomic region.

2. The method of claim 1, further comprising:
- before receiving the plurality of first images, receiving a plurality of third images of a set of fiducial markers, wherein the third images are obtained during manual rotation of the imaging arm, and wherein movement of the imaging arm relative to the support arm is constrained by the stabilization mechanism during the obtaining of the third images; and
- determining a set of distortion correction parameters for the mobile C-arm apparatus based on the third images, wherein the distortion correction parameters are configured for generating the 3D reconstruction based on the second images.

3. The method of claim 1, wherein the stabilization mechanism comprises a shim structure.

4. The method of claim 1, wherein the stabilization mechanism comprises:
a pair of arm regions; and
a bridge region connecting the pair of arm regions.

5. The method of claim 1, wherein the stabilization mechanism is configured to fill at least one gap in an interface between the imaging arm and the support arm.

6. The method of claim 1, wherein the first images are obtained during a propeller rotation of the imaging arm.

7. The method of claim 1, further comprising determining, using at least one sensor coupled to the imaging arm, data indicative of a plurality of poses of the imaging arm during the manual rotation, wherein the geometric calibration parameters are determined based on the data.

8. The method of claim 7, further comprising:
receiving, from the at least one sensor coupled to the imaging arm, data indicative of a plurality of second poses of the imaging arm during a pre-acquisition manual rotation;
comparing the data indicative of the plurality of second poses to the data indicative of the plurality of poses; and
outputting feedback to a user based on the comparison.

9. The method of claim 1, wherein the geometric calibration parameters comprise one or more of a piercing point, skewness, pitch, roll, tilt, or source-to-detector distance of the mobile C-arm apparatus.

10. The method of claim 1, wherein the 3D reconstruction comprises a cone-beam computed tomography reconstruction.

11. A system for imaging an anatomic region of a patient, the system comprising:
one or more processors operably coupled to a mobile C-arm apparatus; and
a memory operably coupled to the one or more processors and storing instructions that when executed by the one or more processors, cause the system to perform operations comprising:
receiving, from a detector carried by an imaging arm of the mobile C-arm apparatus, a plurality of first images of a set of fiducial markers, wherein the first images are obtained during manual rotation of the imaging arm, wherein the mobile C-arm apparatus comprises a support arm movably coupled to the imaging arm, and wherein movement of the imaging arm relative to the support arm is constrained by a stabilization mechanism during the manual rotation; and
determining a set of geometric calibration parameters for the mobile C-arm apparatus based on the first images, wherein the geometric calibration parameters are configured for generating a 3D reconstruction of an anatomic region of a patient based on a plurality of second images of the anatomic region.

12. The system of claim 11, wherein the operations further comprise:
before receiving the plurality of first images, receiving a plurality of third images of a set of fiducial markers, wherein the third images are obtained during manual rotation of the imaging arm, and wherein movement of the imaging arm relative to the support arm is constrained by the stabilization mechanism during the obtaining of the third images; and
determining a set of distortion correction parameters for the mobile C-arm apparatus based on the third images, wherein the distortion correction parameters are configured for generating the 3D reconstruction based on the second images.

13. The system of claim 11, further comprising the stabilization mechanism, wherein the stabilization mechanism comprises a shim structure.

14. The system of claim 11, further comprising the stabilization mechanism, wherein the stabilization mechanism comprises:
a pair of arm regions; and
a bridge region connecting the pair of arm regions.

15. The system of claim 11, further comprising the stabilization mechanism, wherein the stabilization mechanism is configured to fill at least one gap in an interface between the imaging arm and the support arm.

16. The system of claim 11, wherein the first images are obtained during a propeller rotation of the imaging arm.

17. The system of claim 11, wherein the operations further comprise determining, using at least one sensor coupled to the imaging arm, data indicative of a plurality of poses of the imaging arm during the manual rotation, wherein the geometric calibration parameters are determined based on the data.

18. The system of claim 17, wherein the operations further comprise:
receiving, from the at least one sensor coupled to the imaging arm, data indicative of a plurality of second poses of the imaging arm during a pre-acquisition manual rotation;
comparing the data indicative of the plurality of second poses to the data indicative of the plurality of poses; and
outputting feedback to a user based on the comparison.

19. The system of claim 11, wherein the geometric calibration parameters comprise one or more of a piercing point, skewness, pitch, roll, tilt, or source-to-detector distance of the mobile C-arm apparatus.

20. The system of claim 11, wherein the 3D reconstruction comprises a cone-beam computed tomography reconstruction.

* * * * *